United States Patent
Chatila et al.

(10) Patent No.: US 10,391,131 B2
(45) Date of Patent: Aug. 27, 2019

(54) THERAPEUTIC MICROBIOTA FOR THE TREATMENT AND/OR PREVENTION OF FOOD ALLERGY

(71) Applicants: THE BRIGHAM AND WOMEN'S HOSPITAL, INC., Boston, MA (US); CHILDREN'S MEDICAL CENTER CORPORATION, Boston, MA (US)

(72) Inventors: Talal A. Chatila, Belmont, MA (US); Lynn Bry, Jamaica Plain, MA (US); Georg Gerber, Boston, MA (US); Azza Abdel-Gadir, Boston, MA (US); Rima Rachid, Belmont, MA (US)

(73) Assignees: THE BRIGHAM AND WOMEN'S HOSPITAL, INC., Boston, MA (US); CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 16/293,046

(22) Filed: Mar. 5, 2019

(65) Prior Publication Data

US 2019/0192582 A1    Jun. 27, 2019

Related U.S. Application Data

(60) Division of application No. 15/801,783, filed on Nov. 2, 2017, now Pat. No. 10,265,349, which is a continuation of application No. PCT/US2016/060353, filed on Nov. 3, 2016.

(60) Provisional application No. 62/250,277, filed on Nov. 3, 2015.

(51) Int. Cl.

| | |
|---|---|
| *A61K 39/02* | (2006.01) |
| *A61K 35/742* | (2015.01) |
| *A61P 37/00* | (2006.01) |
| *A61K 35/744* | (2015.01) |
| *A61K 9/00* | (2006.01) |
| *A61K 35/745* | (2015.01) |
| *A61K 35/741* | (2015.01) |
| *A61K 35/74* | (2015.01) |
| *A61K 45/06* | (2006.01) |
| *A61P 37/08* | (2006.01) |
| *A61K 9/19* | (2006.01) |

(52) U.S. Cl.
CPC .......... *A61K 35/742* (2013.01); *A61K 9/0053* (2013.01); *A61K 35/74* (2013.01); *A61K 35/741* (2013.01); *A61K 35/744* (2013.01); *A61K 35/745* (2013.01); *A61K 45/06* (2013.01); *A61P 37/00* (2018.01); *A61P 37/08* (2018.01); *A61K 9/19* (2013.01); *Y02A 50/473* (2018.01)

(58) Field of Classification Search
None
See application file for complete search history.

(56) References Cited

U.S. PATENT DOCUMENTS

| | | |
|---|---|---|
| 5,225,202 A | 7/1993 | Hodges |
| 5,733,575 A | 3/1998 | Mehra |
| 5,951,977 A | 9/1999 | Nisbet et al. |
| 6,139,875 A | 10/2000 | Adams |
| 6,420,473 B1 | 7/2002 | Chittamuru |
| 6,455,052 B1 | 9/2002 | Marcussen |
| 6,569,457 B2 | 5/2003 | Ullah |
| 8,460,648 B2 | 6/2013 | Borody |
| 8,486,668 B2 | 7/2013 | Ritter |
| 9,011,834 B1 | 4/2015 | McKenzie et al. |
| 9,408,872 B2 | 8/2016 | Borody |
| 9,433,652 B2 | 9/2016 | Honda et al. |
| 9,642,882 B2 | 5/2017 | Honda et al. |
| 9,662,381 B2 | 5/2017 | Honda et al. |
| 10,052,353 B2 | 8/2018 | Honda et al. |
| 2008/0131556 A1 | 6/2008 | De Simone et al. |
| 2014/0341921 A1 | 11/2014 | Honda et al. |
| 2015/0004130 A1 | 1/2015 | Faber |
| 2016/0158294 A1 | 6/2016 | Von Maltzahn et al. |
| 2016/0317653 A1 | 11/2016 | Cook et al. |
| 2017/0165302 A1 | 6/2017 | Henn et al. |

FOREIGN PATENT DOCUMENTS

| | | |
|---|---|---|
| EP | 0514551 A1 | 11/1992 |
| EP | 2027863 A1 | 2/2009 |
| WO | 2001/060378 A2 | 8/2001 |
| WO | 2002/018614 A1 | 3/2002 |
| WO | 2005/039597 A2 | 5/2005 |
| WO | 2010/062369 A2 | 6/2010 |
| WO | 2014/121298 A2 | 8/2014 |
| WO | 2014/121304 A1 | 8/2014 |
| WO | 2015/095241 A2 | 6/2015 |
| WO | 2017079450 A1 | 5/2017 |

OTHER PUBLICATIONS

Benjamini et al., "Controlling the False Discovery Rate: A Practical and Powerful Approach to Multiple Testing", Journal of the Royal Statistical Society Series B, 57(1) 289-300 (1995).

Cole et al., "Ribosomal Database Project: data and tools for high throughput rRNA analysis", Nucleic Acids Res 42 (Database issue) D633-D642 (2014). Published online Nov. 27, 2013.

Falony et al., "Cross-feeding between Bifidobacterium longum BB536 and acetate-converting, butyrate-producing colon bacteria during growth on oligofructose", Appl Environ Microbiol 72(12) 7835-7841 (2006).

(Continued)

*Primary Examiner* — Jennifer E Graser
(74) *Attorney, Agent, or Firm* — Nixon Peabody LLP; David S. Resnick; Mark J. FitzGerald

(57) ABSTRACT

Disclosed are methods and compositions for the prevention and treatment of food allergy. In particular, described herein are microbial consortia, including minimal microbial consortia, that can prevent and/or cure food allergy. In certain embodiments, the consortia comprise certain members of the taxa Clostridiales and/or Bacteroidetes.

10 Claims, 52 Drawing Sheets

(56) References Cited

OTHER PUBLICATIONS

Gerritsen et al., "Intestinal microbiota in human health and disease: the impact of probiotics", Genes Nutr 6(3) 209-240 (2011).
Helm et al., "A neonatal swine model for peanut allergy", J Allergy Clin Immunol 109(1) 136-142 (2002).
Kozich et al., "Development of a dual-index sequencing strategy and curation pipeline for analyzing amplicon sequence data on the MiSeq Illumina sequencing platform", Appl Environ Microbiol 79(17) 5112-5120 (2013).
Lara-Villoslada et al., "Short-chain fructooligosaccharides, in spite of being fermented in the upper part of the large intestine, have anti-inflammatory activity in the TNBS model of colitis", European Journal of Nutrition 45(7) 418-425 (2006).
Mathias et al., "IgE-mediated systemic anaphylaxis and impaired tolerance to food antigens in mice with enhanced IL-4 receptor signaling", J Allergy Clin Immunol 127(3) 795-805 (2011).
Matsen et al., "pplacer: linear time maximum-likelihood and Bayesian phylogenetic placement of sequences onto a fixed reference tree", BMC Bioinformatics 11:538 (2010).
McMurdie et al., "phyloseq: an R package for reproducible interactive analysis and graphics of microbiome census data", PLoS One 8(4) e61217 (2013).
"Medical Physiology/Gastrointestinal Physiology/Secretions", available at: en.wikibooks.org/wiki/Medical_Physiology/Gastrointestinal_Physiology/Secretions (Printed Feb. 8, 2018).
Noval Rivas et al., "A microbiota signature associated with experimental food allergy promotes allergic sensitization and anaphylaxis", J Allergy Clin Immunol 131(1) 201-212 (2013).
Noval Rivas et al., "Regulatory T Cell Reprogramming toward a Th2-Cell-like Lineage Impairs Oral Tolerance and Promotes Food Allergy", Immunity 42(3) 512-523 (2015).
Open Biome FMT capsules F30 and G3: available on the web at openbiome.org/fmtcapsules/.
Petrof et al., "Stool substitute transplant therapy for the eradication of Clostridium difficile infection: 'RePOOPulating' the gut", Microbiome 1(1) 3 (2013).
Schloss et al., "Introducing mothur: open-source, platform-independent, community-supported software for describing and comparing microbial communities", Appl Environ Microbiol 75(23) 7537-7541 (2009).
Smith et al., "The microbial metabolites, short-chain fatty acids, regulate colonic Treg cell homeostasis", Science 341 (6145) 569-573 (2013).
Yamashita et al., "Production of alpha-linked galactooligosaccharide (alpha-GOS) by alpha-galactosidase from Aspergillus niger APC-9319 and its physical and physiological properties", Journal of Applied Glycoscience 51 (2):115-121 (2004). English Abstract Only.
Faith et al., "Identifying Gut Microbe-Host Phenotype Relationships Using Combinatorial Communities in Gnotobiotic Mice",Sci. Transl. Med. 6(220):220ra11 (2014).
Kailasapathy et al., "Survival and therapeutic potential of probiotic organisms with reference to Lactobacillus acidophilus and *Bifidobacterium* spp", Immunology and Cell Biology 78:80-88 (2000).
Prakash et al., "Gut microbiota: next frontier in understanding human health and development of biotherapeutics", Biologics: Targets and Therapy 5:71-86 (2011).
Song et al. ""*Bacteroides goldsteinii* sp. nov." isolated from clinical specimens of human intestinal origin.", Journal of Clinical Microbiology 43(9): 4522-4527 (2005).
Hopkins et al. "Changes in predominant bacterial populations in human faeces with age and with Clostridium difficile infection", Journal of Medical Microbiology 51(4): 448-452 (2002).
Stefka et al., "Commensal bacteria protect against food allergen sensitization", Proceedings of the National Academy of Sciences of the USA, 111:36 13145-13150 (2014).

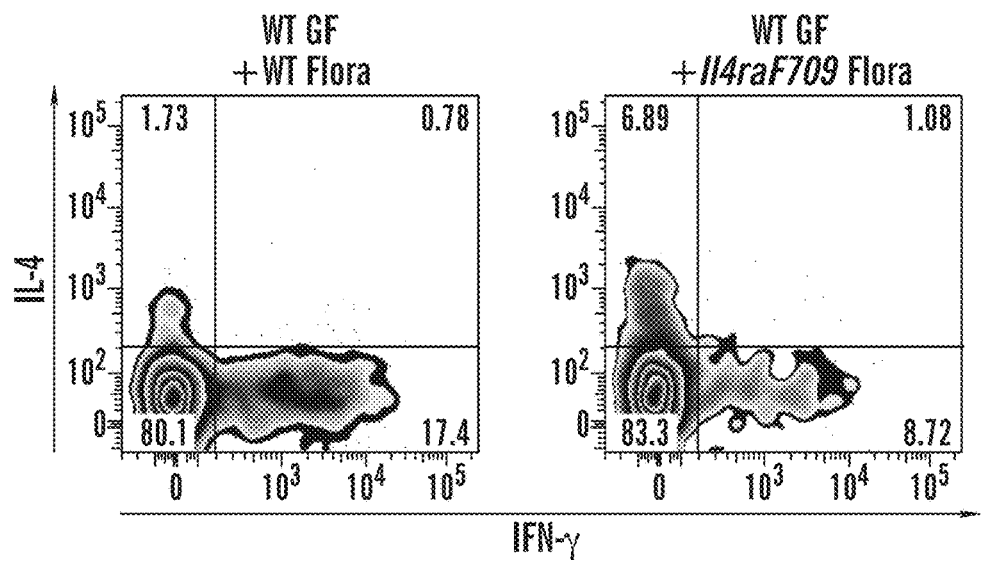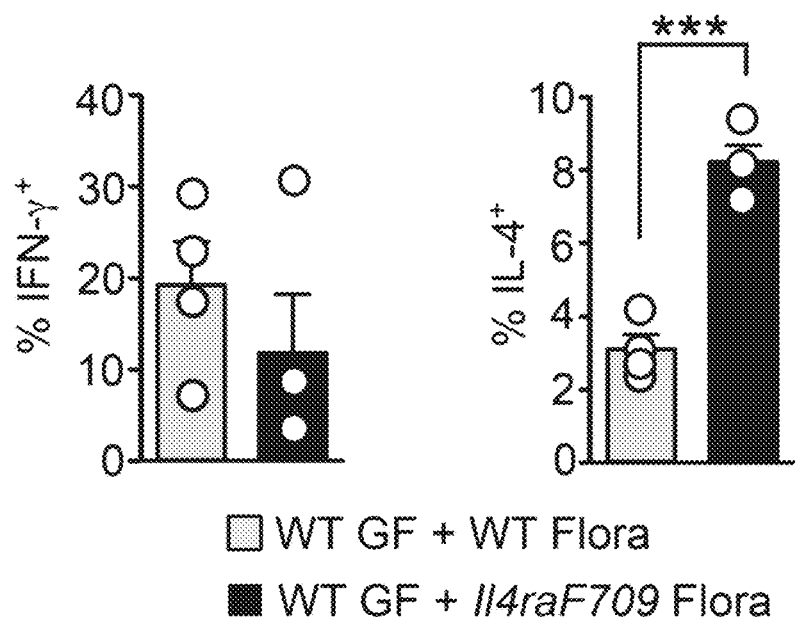
*FIG. 9*

FIG. 14

| Groups | OTU ID | q-Value | WT | F709 | Taxa Lineage |
|---|---|---|---|---|---|
| OVA,Duodenum | Otu00085 | 0.0161 | 0.004071 | 1.00E-04 | Bacteria.Bacteroidetes.Bacteroidia.Bacteroidales.Porphyromonadaceae.unclassified |
| OVA,Jejunum | Otu00085 | 0.0038 | 0.002801 | 1.60E-05 | Bacteria.Bacteroidetes.Bacteroidia.Bacteroidales.Porphyromonadaceae.unclassified |
| OVA,Jejunum | Otu00105 | 0.0108 | 0.003898 | 0.000534 | Bacteria.Firmicutes.Clostridia.Clostridiales.Lachnospiraceae.unclassified |
| OVA,Jejunum | Otu00001 | 0.0907 | 0.054525 | 0.015739 | Bacteria.Firmicutes.Clostridia.Clostridiales.Lachnospiraceae.unclassified |
| OVA,Jejunum | Otu00120 | 0.0907 | 0.006877 | 0.001008 | Bacteria.Firmicutes.Clostridia.Clostridiales.Lachnospiraceae.unclassified |
| OVA,Jejunum | Otu00185 | 0.0919 | 0.003569 | 1.30E-05 | Bacteria.Firmicutes.Clostridia.Clostridiales.Lachnospiraceae.unclassified |
| OVA,Jejunum | Otu00459 | 0.0919 | 2.80E-05 | 5.00E-06 | Bacteria.Firmicutes.Clostridia.Clostridiales.Lachnospiraceae.unclassified |
| OVA,Jejunum | Otu00041 | 0.0919 | 0.004207 | 0.000545 | Bacteria.Firmicutes.Clostridia.Clostridiales.Ruminococcaceae.Oscillibacter |
| OVA,Ileum | Otu00042 | 0.0602 | 0.009597 | 1.80E-05 | Bacteria.Bacteroidetes.Bacteroidia.Bacteroidales.Porphyromonadaceae.unclassified |
| OVA,Ileum | Otu00057 | 0.0602 | 0.01515 | 0.000218 | Bacteria.Bacteroidetes.Bacteroidia.Bacteroidales.Porphyromonadaceae.unclassified |
| OVA,Ileum | Otu00107 | 0.0602 | 0.004906 | 0.000155 | Bacteria.Bacteroidetes.Bacteroidia.Bacteroidales.Porphyromonadaceae.unclassified |
| OVA,Ileum | Otu00063 | 0.0602 | 0.019059 | 0.000216 | Bacteria.Bacteroidetes.unclassified.unclassified.unclassified.unclassified |

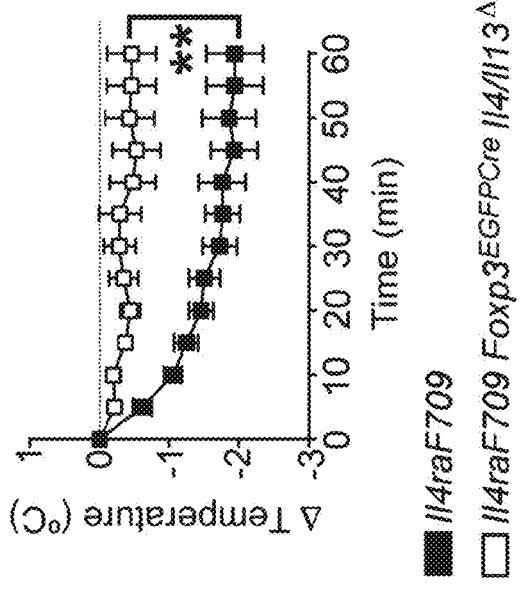
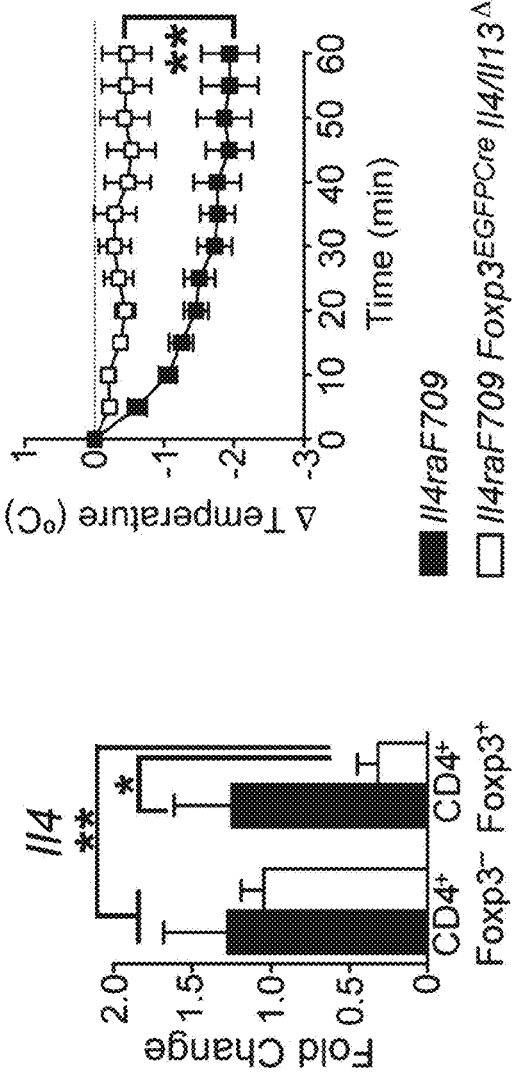
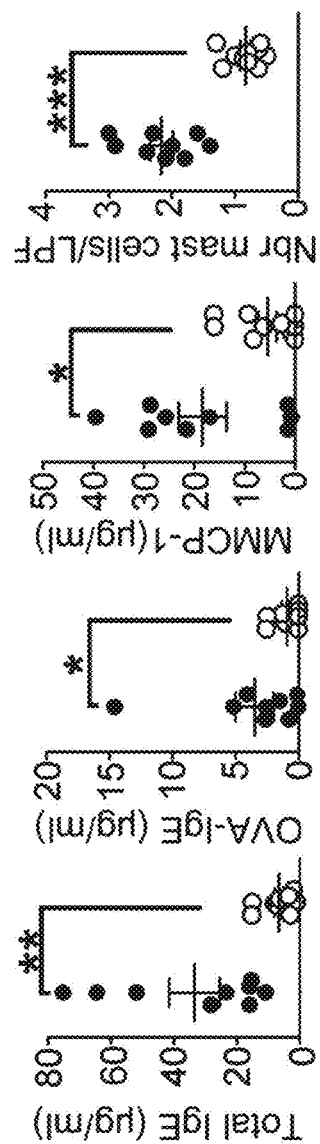
FIG. 18A
FIG. 18B
FIG. 18C

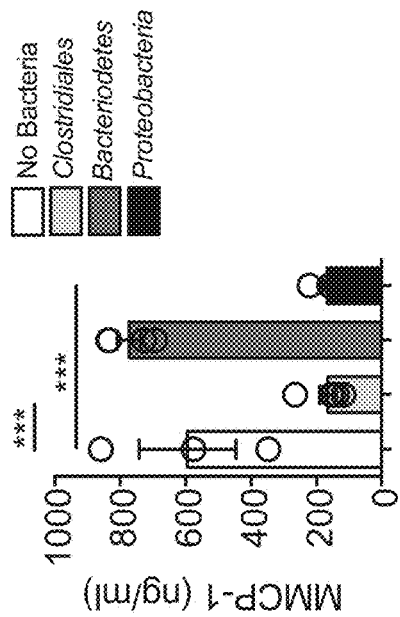
FIG. 21C
FIG. 21D
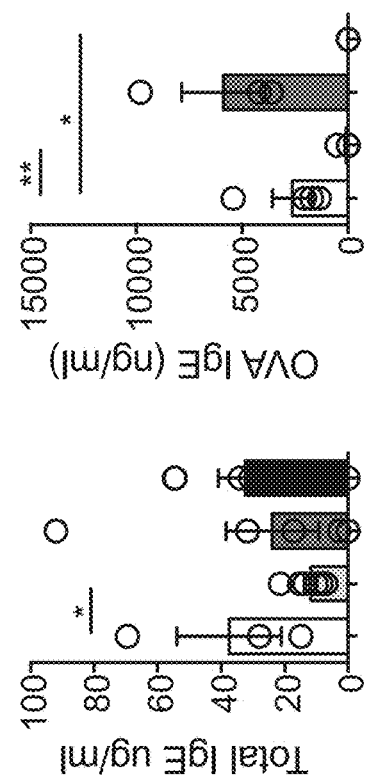
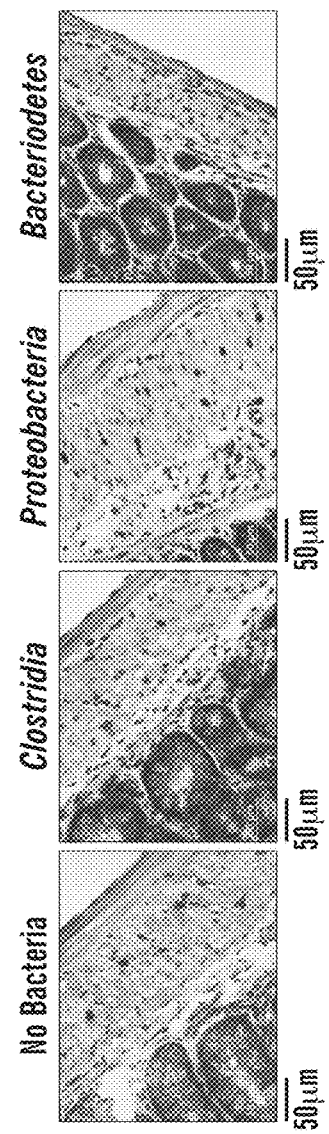
FIG. 21E

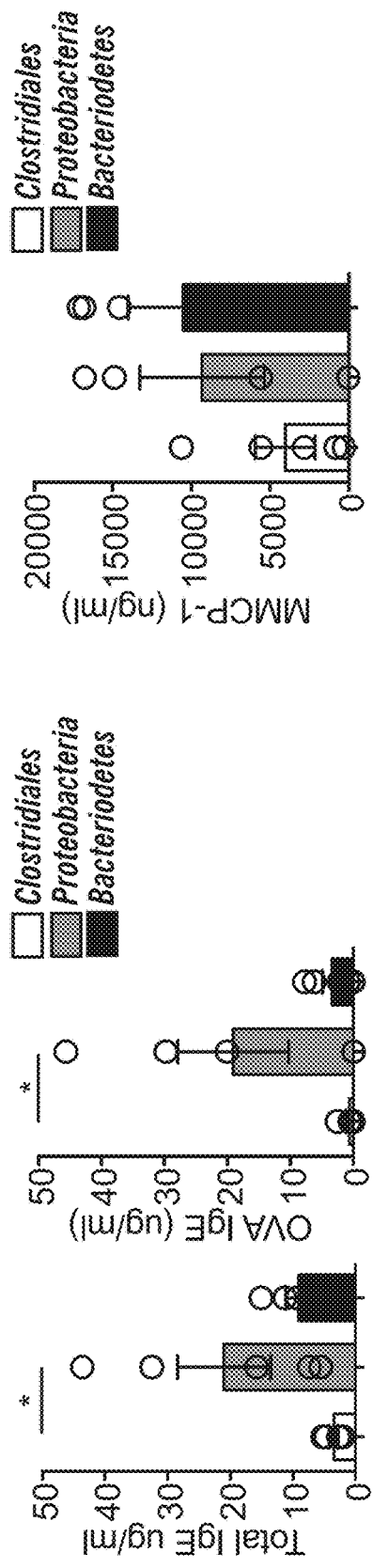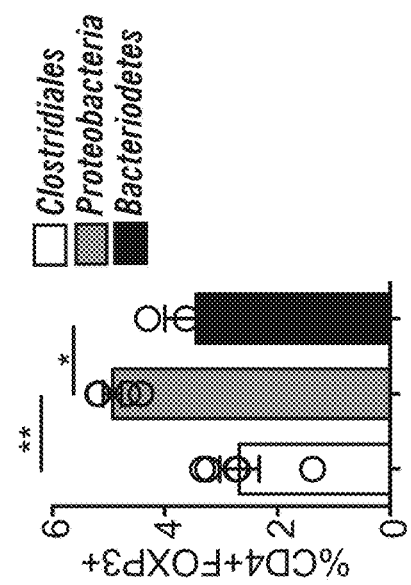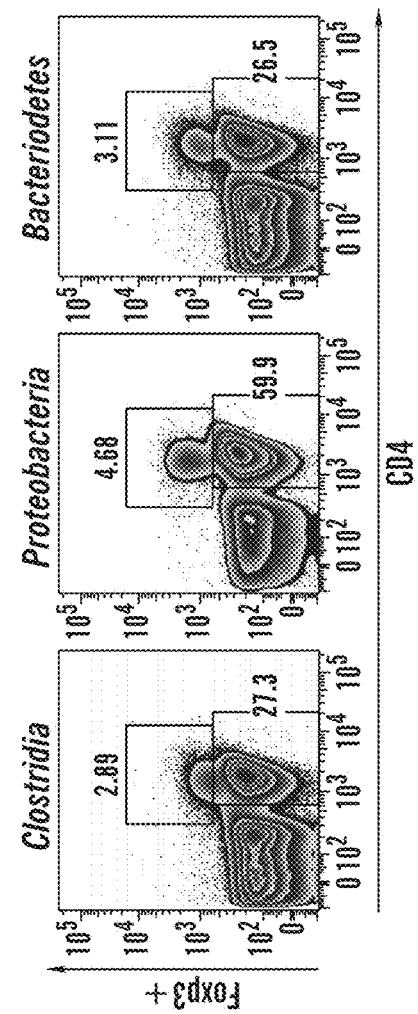
FIG. 23C
FIG. 23D
FIG. 23E
FIG. 23F

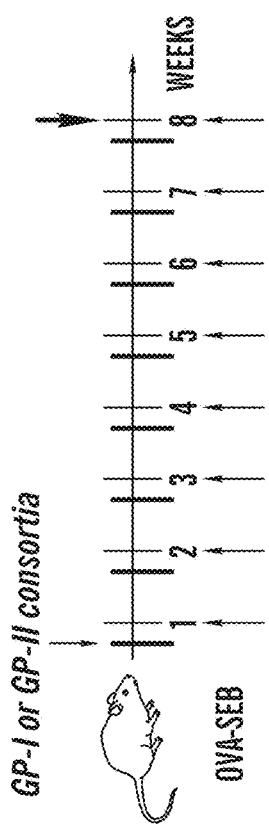
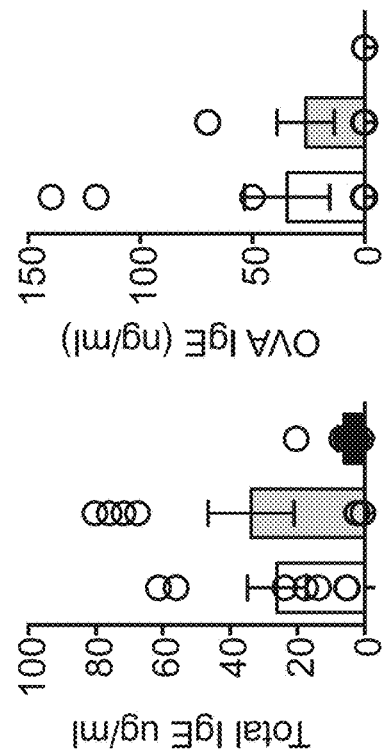
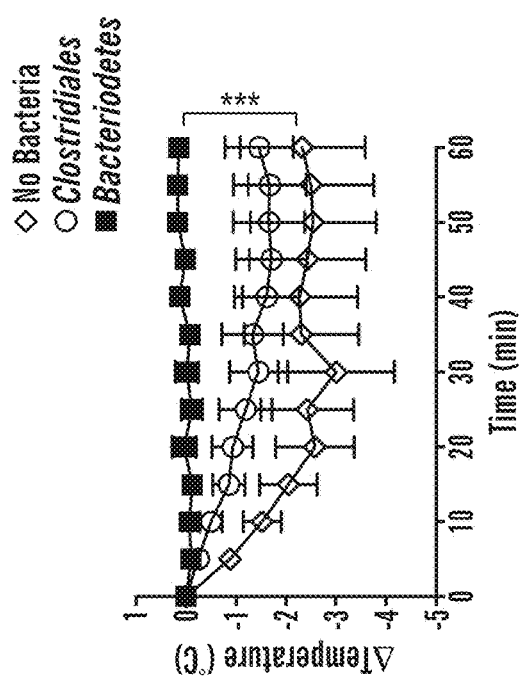
FIG. 24A
FIG. 24B
FIG. 24C

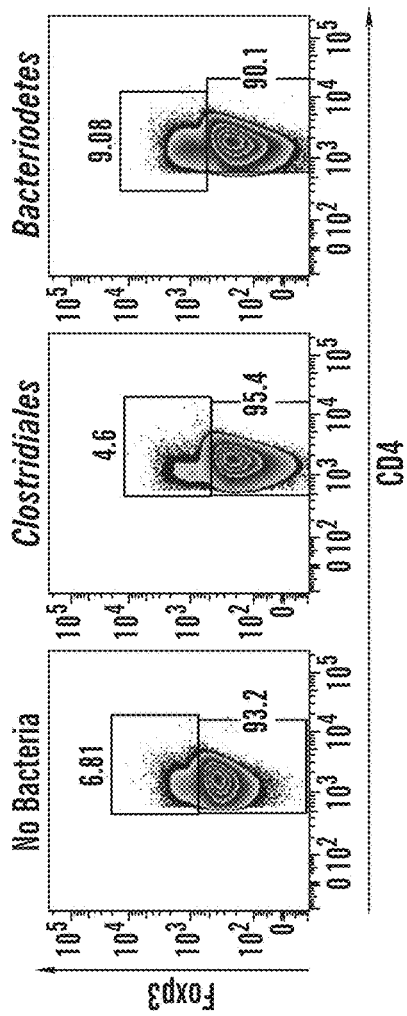
FIG. 24D
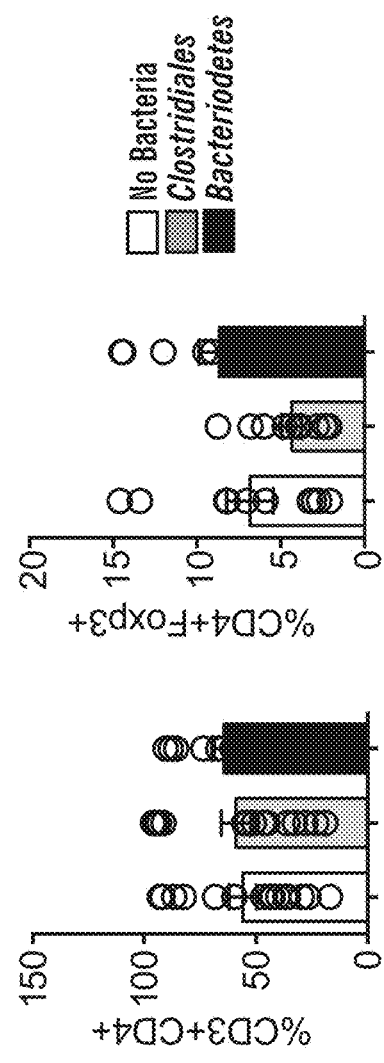
FIG. 24F
FIG. 24E

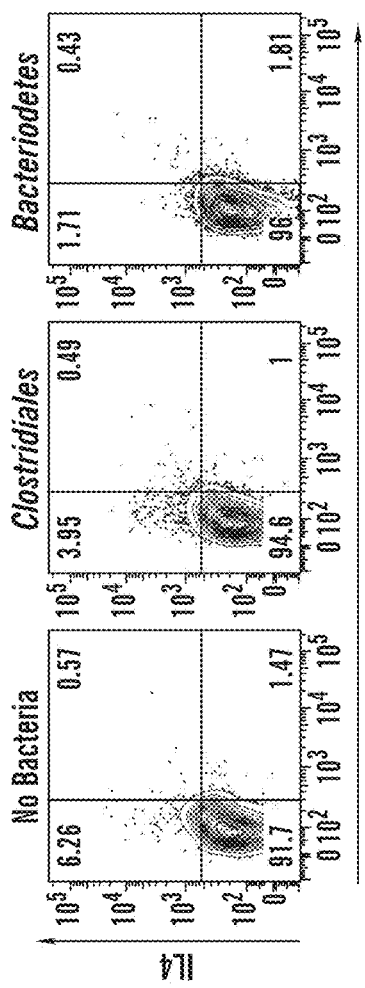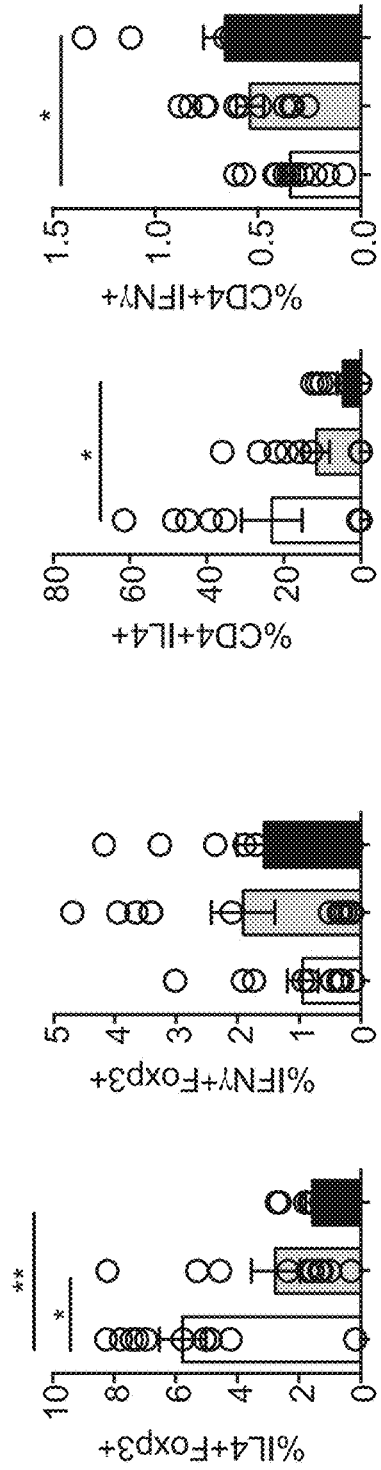
FIG. 24G
FIG. 24H
FIG. 24I
FIG. 24J

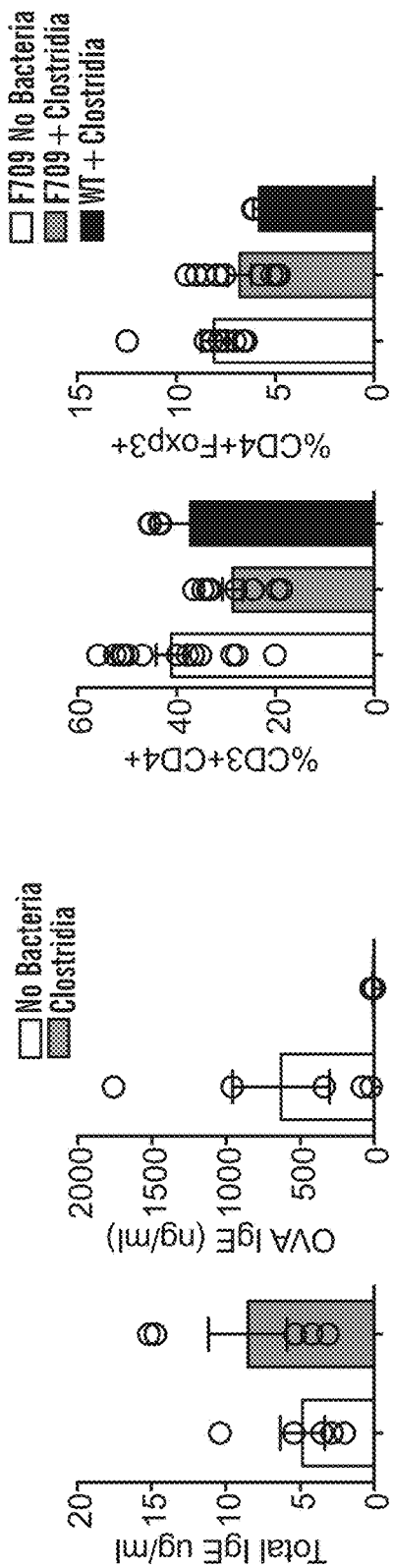
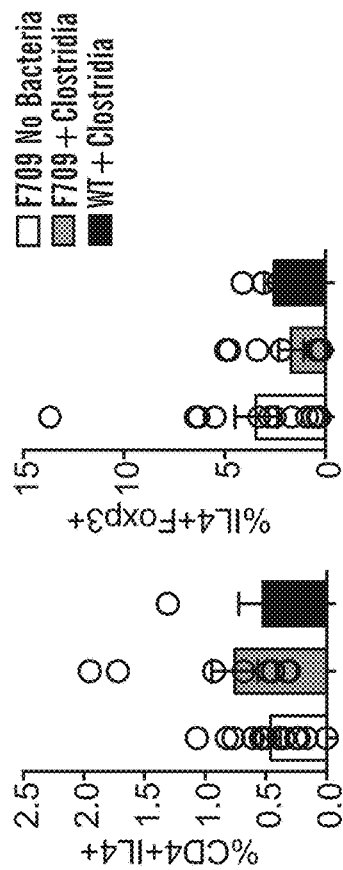
FIG. 25C
FIG. 25D
FIG. 25E

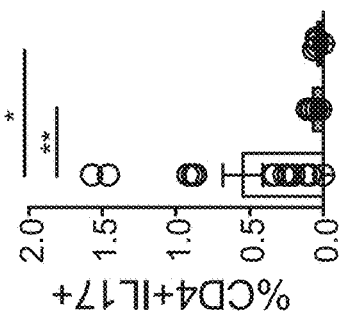
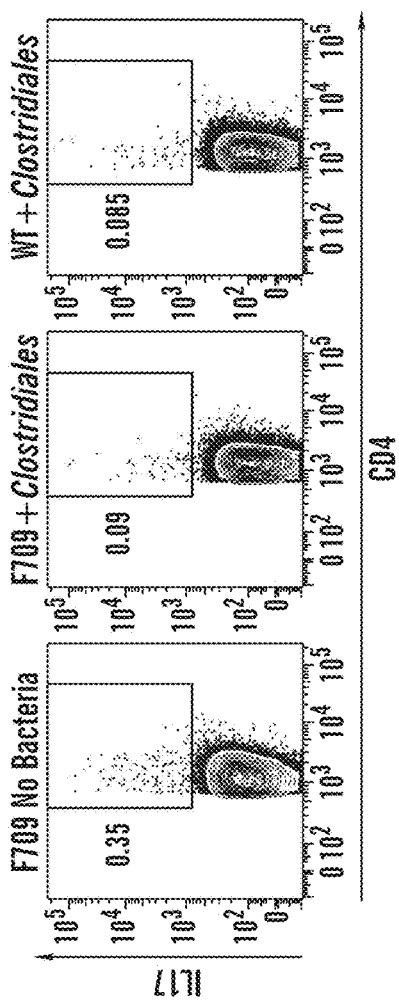
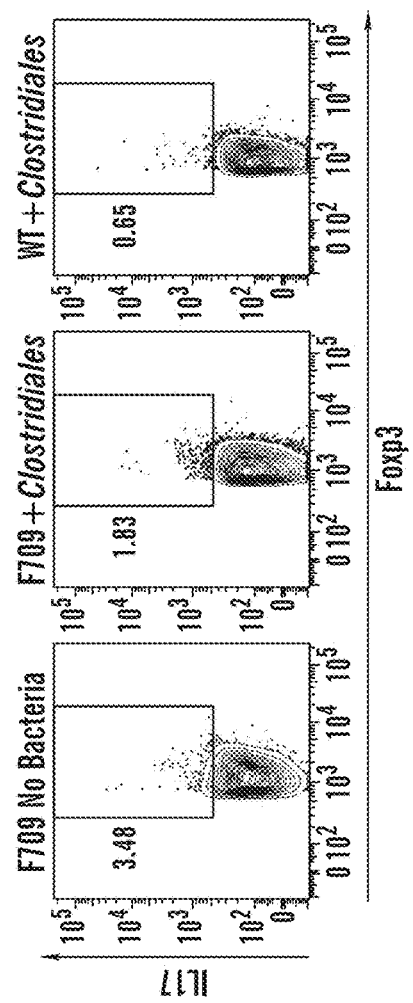
FIG. 25F  FIG. 25G  FIG. 25H  FIG. 25I

THERAPEUTIC MICROBIOTA FOR THE TREATMENT AND/OR PREVENTION OF FOOD ALLERGY

CROSS-REFERENCE TO RELATED APPLICATIONS

This Application is a Divisional of U.S. patent application Ser. No. 15/801,783 filed Nov. 2, 2017, which claims benefit under 35 U.S.C. § 120 and is a Continuation Application of International Application No. PCT/US2016/060353 filed Nov. 3, 2016, which designates the U.S. and which claims benefit under 35 U.S.C. § 119(e) of the U.S. Provisional Application No. 62/250,277 filed Nov. 3, 2015, the contents of each of which are incorporated herein by reference in their entireties.

GOVERNMENT SUPPORT

This invention was made with Government Support under Grant Nos. 1R56AI11798-01 and P30 DK056338 awarded by the National Institutes of Health. The Government has certain rights in the invention.

FIELD OF THE DISCLOSURE

The present disclosure relates to the treatment and/or prevention of food allergy.

BACKGROUND

Food allergies are a growing public health problem in both developed and rapidly developing countries and affects large numbers of children and adults. The incidence of food allergy has increased dramatically in the last few decades. This increase can be associated with sensitization to multiple foods in up to 50% of subjects. Growing evidence indicates that the microbial flora is a key environmental influence in programming oral tolerance.

SUMMARY

Provided herein are methods and compositions for the treatment and/or prevention of food allergy, based in part, on the discovery that altered intestinal microbiota (e.g., from antibiotic treatments, C-section births, diet etc.) can promote food allergy while some combinations of microbes can prevent and/or cure food allergies.

Accordingly, provided herein in one aspect is a pharmaceutical composition comprising: (i) a preparation comprising a minimal microbial consortium consisting essentially of four to eleven strains of viable gut bacteria, in an amount sufficient to treat or prevent a food allergy when administered to an individual in need thereof, and (ii) a pharmaceutically acceptable carrier.

Another aspect provided herein relates to a pharmaceutical composition comprising a minimal microbial consortium of culturable species, and a pharmaceutically acceptable carrier, wherein the consortium is comprised in at least four of the preparations selected from the group consisting of: (i) a preparation of a viable, culturable, anaerobic gut bacterial strain(s) that expresses exopolysaccharide, lipoteichoic acid (LTA), lipopolysaccharide (LPS) or other microbial adjuvant molecules that promote the development of regulatory T cells (Treg); (ii) a preparation of a viable, culturable, anaerobic gut bacterial strain(s) that produces butyrate and/or propionate fermentation products via fermentation of carbohydrates and other carbon sources in the gut lumen; (iii) a preparation of one or more viable, culturable, anaerobic gut bacterial strains that alone or in combination performs the full complement of bile acid transformations; (iv) a preparation of a viable, culturable, anaerobic gut bacterial strain that produces compounds capable of stimulating the aryl hydrocarbon receptor (AhR) receptor pathway in gut epithelial cells, antigen presenting cells and/or T cells to stimulate development of regulatory T cell responses; (v) a preparation of a viable, culturable, anaerobic gut bacterial strain(s) that produces compounds capable of stimulating the pregnane X receptor with beneficial effects upon gut barrier function and/or development of regulatory T cell responses; (vi) a preparation of a viable, culturable, anaerobic gut bacterial strain(s) that produces compounds capable of stimulating the RORgamma (RAR-related orphan receptor gamma) pathways to stimulate development of regulatory T cell responses via direct stimulation or RORgamma-activated pathways in gut antigen presenting cells and/or epithelial cells that then stimulate regulatory T cell responses; (vii) a preparation of viable, culturable, anaerobic gut bacterial strain(s) that stimulates host production of mucins and complex glycoconjugates that improve gut barrier function and colonization by protective commensal species; (viii) a preparation of a viable, culturable, anaerobic gut bacterial strain(s) that alters the gut luminal environment to reduce the deleterious activities of dysbiotic species promoting development of unhealthy allergic T cell responses to food antigens; (ix) a preparation of a viable, culturable, anaerobic gut bacterial strain(s) that alters the gut luminal environment to promote improved colonization by other members of the administered consortium for any of the above stated effects, and/or colonization by existing beneficial species in the patients underlying microbiota; (x) a preparation of a viable, culturable, anaerobic gut bacterial strain(s) that promotes the colonization or growth of a bacterial strain in a preparation of (i)-(ix) above, in vivo.

In one embodiment of this aspect and all other aspects described herein, the viable, culturable, anaerobic gut bacterial strain(s) that expresses exopolysaccharide that promotes the development of regulatory T cells (Treg) is selected from the group consisting of: *Eubacterium rectale, Clostridium ramosum, Butyrovibrio crossatus, Roseburia intestinalis, Clostridium scindens, Clostridium hylemonae, Hungatella hathawayi, Clostridium symbiosum, Faecalibacterium prausnitzii, Subdoligranulum variabile, Bacteroides thetaiotaomicron, Bacteroides fragilis, Bacteroides ovatus, Parabacetroides goldsteinii, Parabacteroides merdae, Parabacteroides distasonis*, and *Prevotella tannerae*.

In another embodiment of this aspect and all other aspects provided herein, the viable, culturable, anaerobic gut bacterial strain(s) that produces butyrate, propionate and/or succinate fermentation products via fermentation of carbohydrates in the gut lumen is selected from the group consisting of: *Bacteroides fragilis, Bacteroides thetaiotaomicron, Bacteroides ovatus, Clostridium sardiniensis, Clostridium hiranonsis, Facealibacterium prausnitzii, Butyrovibrio* spp., *Eubacterium rectale* and *Roseburia intestinalis*

In another embodiment of this aspect and all other aspects provided herein, the one or more viable, culturable, anaerobic gut bacterial strains that alone or in combination performs the full complement of bile acid transformations is *Clostridium scindens, Clostridium hiranonsis, Clostridium sardiniensis* and/or *Bacteroides* spp.

In another embodiment of this aspect and all other aspects provided herein, the viable, culturable, anaerobic gut bacterial strain(s) that produces aryl hydrocarbon receptor agonists sufficient to stimulate host aryl hydrocarbon receptor pathways comprises at least one gene associated with the synthesis of tryptophan, tyrosine or the synthesis of quinone molecules.

In another embodiment of this aspect and all other aspects provided herein, the viable, culturable, anaerobic gut bacterial strain(s) that promotes the colonization or growth of a bacterial strain in a preparation is *Bacteroides* thetaiotaomicron, or *Bacteroides fragilis*.

In another embodiment of this aspect and all other aspects provided herein, the viable, culturable, anaerobic gut bacterial strain(s) that produces compounds endogenously or by metabolizing exogenous precursors, that is capable of stimulating the pregnane X receptor with beneficial effects upon gut barrier function and/or development of regulatory T cell responses is a strain that expresses desmolase and/or hydroxysteroid dehydrogenase. In this context, exogenous precursors include not just dietary compounds or factors, but also factors produced by the host and excreted into the gut which are then acted upon by one or more members of a microbial consortium as described herein.

In another embodiment of this aspect and all other aspects provided herein, the viable, culturable, anaerobic gut bacterial strain(s) that produces compounds endogenously or by metabolizing exogenous precursors, that is capable of stimulating the RORgamma (RAR-related orphan receptor gamma) pathways to stimulate development of regulatory T cell responses is a strain that expresses at least one cholesterol reductase or another enzyme capable of metabolizing sterol compounds.

In another embodiment of this aspect and all other aspects provided herein, the viable, culturable, anaerobic gut bacterial strain(s) that is capable of stimulating host mucins and complex glycoconjugates that improve gut barrier function and colonization by protective commensal species is *Bacteroides* thetaiotaomicron or *Bacteroides fragilis*.

In another embodiment of this aspect and all other aspects provided herein, the viable, culturable, anaerobic gut bacterial strain(s) that alter the gut luminal environment to reduce the deleterious activities of dysbiotic species that contribute to development of pathogenic allergic T cell responses to food antigens is *Bacteroides* thetaiotaomicron, *Bacteroides fragilis* or another *Bacteroides* spp. An examples includes alterations of the gut environment from *Bacteroides* species that reduces the biomass of dysbiotic species in the Enterobacteriaceae or Desulfonovibriaceae and/or prevent full expression of dysbiotic biochemical or microbiologic activities expressed by these species.

In another embodiment of this aspect and all other aspects provided herein, the viable, culturable, anaerobic gut bacterial strain(s) alter the gut luminal environment to promote improved colonization by other members of the administered consortium for any of the above stated effects, and/or colonization by existing beneficial species in the patients underlying microbiota is *Bacteroides* thetaiotaomicron, *Bacteroides fragilis*, or *Bacteroides* spp. In another embodiment of this aspect and all other aspects provided herein, the beneficial species comprises *Clostridium* spp (e.g., *Clostridium ramosum, Clostridium scindens, Clostridium hiranonsis, Clostridium bifermentans, Clostridium leptum, Clostridium sardiniensis, Clostridium hathewayi, Clostridium nexile, Clostridium hylemonae, Clostridium glycyrrhizinilyticum, Clostridium lavalense, Clostridium fimetarium, Clostridium symbiosum, Clostridium sporosphaeroides* etc.) or another non-pathogenic commensal strain.

In another embodiment of this aspect and all other aspects provided herein, the pharmaceutically acceptable carrier comprises an enteric coating composition that encapsulates the minimal microbial consortium.

In another embodiment of this aspect and all other aspects provided herein, the pharmaceutical composition is formulated to deliver the viable bacteria to the small intestine.

In another embodiment of this aspect and all other aspects provided herein, the enteric-coating composition is in the form of a capsule, gel, pastille, tablet or pill.

In another embodiment of this aspect and all other aspects provided herein, the strains of viable, culturable, anaerobic gut bacteria are human gut bacteria.

In another embodiment of this aspect and all other aspects provided herein, the strains of viable, culturable, anaerobic gut bacteria are selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile*, and *Veilonella ratti*.

In another embodiment of this aspect and all other aspects provided herein, the strains of viable, culturable, anaerobic gut bacteria are selected from the group consisting of: *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii,* and *Prevotella tannerae*.

In another embodiment of this aspect and all other aspects provided herein, the strains of viable, culturable, anaerobic gut bacteria are selected from the group consisting of: (i) *Clostridium ramosum, C. scindens, C. hiranonsis, C. bifermentans, C. leptum*, and *C. sardiniensis*, or (ii) *Bacteroides fragilis, B. thetaiotaomicron, B. ovatus, Parabacteroides goldsteinii,* and *Prevotella tannerae*.

In another embodiment of this aspect and all other aspects provided herein, the strains of viable, culturable, anaerobic gut bacteria are present in substantially equal biomass.

In another embodiment of this aspect and all other aspects provided herein, the composition is formulated to deliver a dose of at least $1 \times 10^9$ colony forming units (CFUs).

In another embodiment of this aspect and all other aspects provided herein, the composition is formulated to deliver at least $1 \times 10^9$ CFUs in less than 30 capsules per one time dose.

In another embodiment of this aspect and all other aspects provided herein, the composition is frozen for storage.

In another embodiment of this aspect and all other aspects provided herein, the strain(s) of viable culturable, anaerobic gut bacteria are encapsulated under anaerobic conditions.

In another embodiment of this aspect and all other aspects provided herein, the strain(s) of viable culturable, anaerobic gut bacteria are lyophilized under anaerobic conditions.

In another embodiment of this aspect and all other aspects provided herein, anaerobic conditions comprise one or more of the following: (i) oxygen impermeable capsules, (ii) addition of reducing agents including N-acetylcysteine, cysteine, or methylene blue to the composition, and (iii) use of spores for organisms that sporulate.

In another embodiment of this aspect and all other aspects provided herein, the consortium comprises at least one bacterial strain comprising a 16S rDNA sequence at least 97% identical to a 16S rDNA sequence present in a reference strain operational taxonomic unit, the reference strain selected from the group consisting of: *Clostridium ramosum, C. scindens, C. hiranonsis, C. bifermentans, C. leptum*, and *C. sardiniensis*, or wherein the consortium comprises at least one bacterial strain comprising a 16S rDNA sequence at least 97% identical to a 16S rDNA sequence present in a reference strain operational taxonomic unit, the reference strain selected from the group consisting of: *Bacteroides fragilis, B. thetaiotaomicron, B. ovatus, Parabacteroides goldsteinii*, and *Prevotella tannerae*.

In another embodiment of this aspect and all other aspects provided herein, the consortium does not comprise any of the Species *Escherichia coli, Klebsiella pneumoniae, Proteus mirabilis, Enterobacter cloacae, Bilophila wadsworthia, Alistipes onderdonkii, Desulfovibrio* species, *Lactobacillus johnsoni, Parasutterella excrementihominis*.

In another embodiment of this aspect and all other aspects provided herein, the consortium does not comprise bacteria of the Genera *Bilophila, Enterobacter, Escherichia, Klebsiella, Proteus, Alistipes, Blautia, Desulfovibrio*, or *Parasutterella*.

In another embodiment of this aspect and all other aspects provided herein, the consortium does not comprise bacteria of the Families Desulfovibrionaceae, Enterobacteriaceae, Rikenellaceae, and Sutterellaceae.

In another embodiment of this aspect and all other aspects provided herein, the consortium does not comprise bacteria of the Families Lactobacillaceae, or Enterbacteriaceae.

In another embodiment of this aspect and all other aspects provided herein, the consortium does not comprise bacteria of the Order Burkholdales, Desulfovibrionales, or Enterobacteriales.

In another embodiment of this aspect and all other aspects provided herein, the composition comprises at least five strains of viable non-pathogenic gut bacteria.

In another embodiment of this aspect and all other aspects provided herein, the composition comprises up to eleven strains of viable non-pathogenic gut bacteria.

In another embodiment of this aspect and all other aspects provided herein, the composition comprises *Clostridium ramosum, C. scindens, C. hiranonsis, C. bifermentans, C. leptum*, and *C. sardiniensis*.

In another embodiment of this aspect and all other aspects provided herein, the composition comprises *Bacteroides fragilis, B. thetaiotaomicron, B. ovatus, Parabacteroides goldsteinii*, and *Prevotella tannerae*.

In another embodiment of this aspect and all other aspects provided herein, the composition comprises: *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii*, and *Prevotella tannerae*.

In another embodiment of this aspect and all other aspects provided herein, the bacterial strains in the composition consists essentially of *Clostridium ramosum, C. scindens, C. hiranonsis, C. bifermentans, C. leptum*, and *C. sardiniensis*.

In another embodiment of this aspect and all other aspects provided herein, the microbial consortium consists essentially of *Bacteroides fragilis, B. thetaiotaomicron, B. ovatus, Parabacteroides goldsteinii*, and *Prevotella tannerae*.

In another embodiment of this aspect and all other aspects provided herein, the microbial consortium consists essentially of: *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii*, and *Prevotella tannerae*.

In another embodiment of this aspect and all other aspects provided herein, the enteric-coating comprises a polymer, nanoparticle, fatty acid, shellac, or a plant fiber.

In another embodiment of this aspect and all other aspects provided herein, the composition further comprises a prebiotic composition.

In another embodiment of this aspect and all other aspects provided herein, the composition is encapsulated, a reconstituted lyophilisate, a food item, or is formulated as a liquid, gel, fluid-gel, or nanoparticles in a liquid.

Another aspect provided herein relates to a pharmaceutical composition comprising: (i) a preparation comprising at least four strains of viable, anaerobic, culturable gut bacteria selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile*, and *Veilonella ratti.*, in an amount sufficient to treat or prevent a food allergy when administered to an individual in need thereof, and (ii) a pharmaceutically acceptable carrier.

In one embodiment of this aspect and all other aspects provided herein, the composition comprises not more than forty strains of viable, anaerobic, culturable gut bacteria.

In another embodiment of this aspect and all other aspects provided herein, the composition comprises not more than thirty strains of viable, anaerobic, culturable gut bacteria.

In another embodiment of this aspect and all other aspects provided herein, the composition comprises not more than twenty strains of viable, anaerobic, culturable gut bacteria.

In another embodiment of this aspect and all other aspects provided herein, the composition comprises not more than fifteen strains of viable, anaerobic, culturable gut bacteria.

In another embodiment of this aspect and all other aspects provided herein, the composition comprises not more than eleven strains of viable, anaerobic, culturable gut bacteria.

In another embodiment of this aspect and all other aspects provided herein, the composition comprises at least five strains of viable, anaerobic, culturable gut bacteria selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile*, and *Veilonella ratti*.

In another embodiment of this aspect and all other aspects provided herein, the composition comprises at least six strains of viable, anaerobic, culturable gut bacteria selected from the group consisting of: *Clostridium ramosum,*

*Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile,* and *Veilonella ratti.*

In another embodiment of this aspect and all other aspects provided herein, the composition comprises at least seven strains of viable, anaerobic, culturable gut bacteria selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile,* and *Veilonella ratti.*

In another embodiment of this aspect and all other aspects provided herein, the composition comprises at least eight strains of viable, anaerobic, culturable gut bacteria selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile,* and *Veilonella ratti.*

In another embodiment of this aspect and all other aspects provided herein, the composition comprises at least nine strains of viable, anaerobic, culturable gut bacteria selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile,* and *Veilonella ratti.*

In another embodiment of this aspect and all other aspects provided herein, the composition comprises at least ten strains of viable, anaerobic, culturable gut bacteria selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile,* and *Veilonella ratti.*

In other embodiments of this aspect and all other aspects provided herein, the composition comprises a range of 4-28, 4-35, 4-30, 4-25, 4-20, 4-15, 4-12, 4-11, 4-10, 4-9, 4-8, 4-6, 35-40, 30-40, 25-40, 20-40, 15-40, 12-40, 11-40, 10-40, 6-40, 5-40, 10-20, 10-30, 10-25, 15-40, 15-35, 15-30, 15-25, 15-20, 20-35, 20-30, 20-25, 30-35 strains of viable, anaerobic, culturable gut bacteria.

In another embodiment of this aspect and all other aspects provided herein, the strains of viable, anaerobic, culturable gut bacteria are selected from the group consisting of: (i) *Clostridium ramosum, C. scindens, C. hiranonsis, C. bifermentans, C. leptum,* and *C. sardiniensis,* or (ii) *Bacteroides fragilis, B. thetaiotaomicron, B. ovatus, Parabacteroides goldsteinii,* and *Prevotella tannerae.*

In another embodiment of this aspect and all other aspects provided herein, the composition comprises viable, anaerobic, culturable gut bacteria including each of *Clostridium ramosum, C. scindens, C. hiranonsis, C. bifermentans, C. leptum* and *C. sardiniensis.*

In another embodiment of this aspect and all other aspects provided herein, the composition comprises viable, anaerobic, culturable gut bacteria including each of, *Bacteroides fragilis, B. thetaiotaomicron, B. ovatus, Parabacteroides goldsteinii,* and *Prevotella tannerae.*

In another embodiment of this aspect and all other aspects provided herein, the composition comprises viable, anaerobic, culturable gut bacteria including each of *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii,* and *Prevotella tannerae.*

Another aspect described herein relates to a pharmaceutical composition comprising: at least four strains of viable, anaerobic, culturable gut bacteria comprising: at least one bacterial strain comprising a 16S rDNA sequence at least 97% identical to a 16S rDNA sequence present in a reference strain operational taxonomic unit, the reference strain selected from the group consisting of: *Clostridium ramosum, C. scindens, C. hiranonsis, C. bifermentans, C. leptum,* and *C. sardiniensis;* or at least one bacterial strain comprising a 16S rDNA sequence at least 97% identical to a 16S rDNA sequence present in a reference strain operational taxonomic unit, the reference strain selected from the group consisting of: *Bacteroides fragilis, B. thetaiotaomicron, B. ovatus, Parabacteroides goldsteinii,* and *Prevotella tannerae;* wherein the at least four strains of viable, anaerobic, culturable gut bacteria are present in an amount sufficient to treat or prevent a food allergy when administered to an individual in need thereof; and a pharmaceutically acceptable carrier.

In another embodiment of this aspect and all other aspects provided herein, the composition comprises not more than forty strains of viable, anaerobic, culturable gut bacteria.

In another embodiment of this aspect and all other aspects provided herein, the composition comprises not more than thirty strains of viable, anaerobic, culturable gut bacteria.

In another embodiment of this aspect and all other aspects provided herein, the composition comprises not more than twenty strains of viable, anaerobic, culturable gut bacteria.

In another embodiment of this aspect and all other aspects provided herein, the composition comprises not more than fifteen strains of viable, anaerobic, culturable gut bacteria.

In another embodiment of this aspect and all other aspects provided herein, the composition comprises not more than eleven strains of viable, anaerobic, culturable gut bacteria.

In another embodiment of this aspect and all other aspects provided herein, the composition comprises at least five strains of viable, anaerobic, culturable gut bacteria.

In another embodiment of this aspect and all other aspects provided herein, the composition comprises at least six strains of viable, anaerobic, culturable gut bacteria.

In another embodiment of this aspect and all other aspects provided herein, the composition comprises at least seven strains of viable, anaerobic, culturable gut bacteria.

In another embodiment of this aspect and all other aspects provided herein, the composition comprises at least eight strains of viable, anaerobic, culturable gut bacteria.

In another embodiment of this aspect and all other aspects provided herein, the composition comprises at least nine strains of viable, anaerobic, culturable gut bacteria.

In another embodiment of this aspect and all other aspects provided herein, the composition comprises at least ten strains of viable, anaerobic, culturable gut bacteria.

In another embodiment of this aspect and all other aspects provided herein, the composition comprises eleven strains of viable, anaerobic, culturable gut bacteria.

In another embodiment of this aspect and all other aspects provided herein, the microbial strains do not comprise any of the Species *Escherichia coli, Klebsiella pneumoniae, Proteus mirabilis, Enterobacter cloacae, Bilophila wadsworthia, Alistipes onderdonkii, Desulfovibrio* species, *Lactobacillus johnsoni*, and *Parasutterella excrementihominis*.

In another embodiment of this aspect and all other aspects provided herein, the microbial strains do not comprise bacteria of the Genera *Bilophila, Enterobacter, Escherichia, Klebsiella, Proteus, Alistipes, Blautia, Desulfovibrio*, or *Parasutterella*.

In another embodiment of this aspect and all other aspects provided herein, the microbial strains do not comprise bacteria of the Families Desulfovibrionaceae, Enterobacteriaceae, Rikenellaceae, and Sutterellaceae.

In another embodiment of this aspect and all other aspects provided herein, the microbial strains do not comprise bacteria of the Families Lactobacillaceae, or Enterbacteriaceae In another embodiment of this aspect and all other aspects provided herein, the microbial strains do not comprise bacteria of the Order Burkholdales, Desulfovibrionales, or Enterobacteriales.

Another aspect provided herein relates to a pharmaceutical composition comprising a microbial consortium of culturable species, and a pharmaceutically acceptable carrier, wherein the composition comprises at least four preparations selected from the group consisting of: (i) a preparation of a viable, culturable, anaerobic gut bacterial strain (or strains) that expresses exopolysaccharide, lipoteichoic acid (LTA), lipopolysaccharide (LPS) or other microbial adjuvant molecules that promote the development of regulatory T cells (Treg); (ii) a preparation of a viable, culturable, anaerobic gut bacterial strain (or strains) that produces butyrate and/or propionate fermentation products via fermentation of carbohydrates and other carbon sources in the gut lumen; (iii) a preparation of one or more viable, culturable, anaerobic gut bacterial strains that alone or in combination performs the full complement of bile acid transformations; (iv) a preparation of a viable, culturable, anaerobic gut bacterial strain (or strains) that produces compounds capable of stimulating the aryl hydrocarbon receptor (AhR) receptor pathway in gut epithelial cells, antigen presenting cells and/or T cells to stimulate development of regulatory T cell responses; (v) a preparation of a viable, culturable, anaerobic gut bacterial strain (or strains) that produces compounds capable of stimulating the pregnane X receptor with beneficial effects upon gut barrier function and/or development of regulatory T cell responses; (vi) a preparation of a viable, culturable, anaerobic gut bacterial strain (or strains) that produces compounds capable of stimulating the ROR-gamma (RAR-related orphan receptor gamma) pathways to stimulate development of regulatory T cell responses via direct stimulation or RORgamma-activated pathways in gut antigen presenting cells and/or epithelial cells that then stimulate regulatory T cell responses; (vii) a preparation of a viable, culturable, anaerobic gut bacterial strain (or strains) that stimulates host production of mucins and complex glycoconjugates that improve gut barrier function and colonization by protective commensal species; (viii) a preparation of a viable, culturable, anaerobic gut bacterial strain (or strains) that alters the gut luminal environment to reduce the deleterious activities of dysbiotic species promoting development of unhealthy allergic T cell responses to food antigens; (ix) a preparation of a viable, culturable, anaerobic gut bacterial strain (or strains) that alters the gut luminal environment to promote improved colonization by other members of the administered consortium for any of the above stated effects, and/or colonization by existing beneficial species in the patients underlying microbiota; and (x) a preparation of a viable, culturable, anaerobic gut bacterial strain (or strains) that promotes the colonization or growth of a bacterial strain in a preparation of (i)-(ix) above, in vivo; and wherein the composition comprises no more than forty microbial species.

In one embodiment of this aspect and all other aspects provided herein, the composition comprises no more than thirty microbial species.

In another embodiment of this aspect and all other aspects provided herein, the composition comprises no more than twenty microbial species.

In another embodiment of this aspect and all other aspects provided herein, the composition comprises no more than fifteen microbial species.

In another embodiment of this aspect and all other aspects provided herein, the composition comprises no more than eleven microbial species.

In another embodiment of this aspect and all other aspects provided herein, the composition comprises at least five of the preparations (i)-(x).

In another embodiment of this aspect and all other aspects provided herein, the composition comprises at least six of the preparations (i)-(x).

In another embodiment of this aspect and all other aspects provided herein, the composition comprises at least seven of the preparations (i)-(x).

In another embodiment of this aspect and all other aspects provided herein, the composition comprises at least eight of the preparations (i)-(x).

In another embodiment of this aspect and all other aspects provided herein, the composition comprises at least nine of the preparations (i)-(x).

In another embodiment of this aspect and all other aspects provided herein, the composition comprises each of the preparations (i)-(x).

In another embodiment of this aspect and all other aspects provided herein, the anaerobic gut bacterial strain that expresses exopolysaccharide that promotes the development of regulatory T cells (Treg) is selected from the group consisting of: *Eubacterium rectale, Clostridium ramosum, Butyrovibrio crossatus, Roseburia intestinalis, Clostridium scindens, Clostridium hylemonae, Hungatella hathawayi, Clostridium symbiosum, Faecalibacterium prausnitzii, Subdoligranulum variabile, Bacteroides thetaiotaomicron, Bacteroides fragilis, Bacteroides ovatus, Parabacetroides goldsteinii, Parabacteroides merdae, Parabacteroides distasonis,* and *Prevotella tannerae.*

In another embodiment of this aspect and all other aspects provided herein, the anaerobic gut bacterial strain that strain that produces butyrate, propionate and/or succinate fermentation products via fermentation of carbohydrates in the gut lumen is selected from the group consisting of: *Bacteroides fragilis, Bacteroides thetaiotaomicron, Bacteroides ovatus, Clostridium sardiniensis, Clostridium hiranonsis, Faecalibacterium prausnitzii, Butyrovibrio* spp., *Eubacterium rectale,* and *Roseburia intestinalis.*

In another embodiment of this aspect and all other aspects provided herein, the anaerobic gut bacterial strain that alone or in combination performs the full complement of bile acid transformations lumen is selected from the group consisting of: *Bacteroides fragilis, Bacteroides thetaiotaomicron, Bacteroides ovatus, Clostridium sardiniensis, Clostridium hiranonsis, Facealibacterium prausnitzii, Butyrovibrio* spp., *Eubacterium rectale,* and *Roseburia intestinalis.*

In another embodiment of this aspect and all other aspects provided herein, the anaerobic gut bacterial strain that produces aryl hydrocarbon receptor agonists sufficient to stimulate host aryl hydrocarbon receptor pathways comprises at least one gene associated with the synthesis of tryptophan, tyrosine or the synthesis of quinone molecules In another embodiment of this aspect and all other aspects provided herein, the anaerobic gut bacterial strain that promotes the colonization or growth of a bacterial strain in a preparation recited in claim 2 is *Bacteroides* thetaiotaomicron, or *Bacteroides fragilis.*

In another embodiment of this aspect and all other aspects provided herein, the anaerobic gut bacterial strain that produces compounds endogenously or by metabolizing ingested precursors, that is capable of stimulating the pregnane X receptor with beneficial effects upon gut barrier function and/or development of regulatory T cell responses is a strain that expresses desmolase and/or hydroxysteroid dehydrogenase.

In another embodiment of this aspect and all other aspects provided herein, the anaerobic gut bacterial strain that produces compounds endogenously or by metabolizing ingested precursors, that is capable of stimulating the ROR-gamma (RAR-related orphan receptor gamma) pathways to stimulate development of regulatory T cell responses is a strain that expresses at least one cholesterol reductase or another enzyme(s) capable of metabolizing sterol compounds.

In another embodiment of this aspect and all other aspects provided herein, the anaerobic gut bacterial strain that is capable of stimulating host mucins and complex glycoconjugates that improve gut barrier function and colonization by protective commensal species is *Bacteroides thetaiotaomicron* or *Bacteroides fragilis.*

In another embodiment of this aspect and all other aspects provided herein, the anaerobic gut bacterial strains that alter the gut luminal environment to reduce the deleterious activities of dysbiotic species that contribute to development of pathogenic allergic T cell responses to food antigens is *Bacteroides thetaiotaomicron, Bacteroides fragilis,* or *Bacteroides* spp. In another embodiment of this aspect and all other aspects provided herein, the dysbiotic species comprises a species in the Families Enterobacteriaceae or Desulfonovibriacaea.

In another embodiment of this aspect and all other aspects provided herein, the anaerobic gut bacterial strains alter the gut luminal environment to promote improved colonization by other members of the administered consortium for any of the above stated effects, and/or colonization by existing beneficial species in the patients underlying microbiota is *Bacteroides thetaiotaomicron, Bacteroides fragilis,* or *Bacteroides* spp. In another embodiment of this aspect and all other aspects provided herein, the beneficial species comprises non-pathogenic *Clostridia* spp. and other non-pathogenic commensal strains.

In another embodiment of this aspect and all other aspects provided herein, the pharmaceutically acceptable carrier comprises an enteric coating composition that encapsulates the anaerobic gut bacterial strains.

In another embodiment of this aspect and all other aspects provided herein, the composition is formulated to deliver the viable bacteria to the small intestine.

In another embodiment of this aspect and all other aspects provided herein, wherein the enteric-coating composition is in the form of a capsule, gel, pastille, tablet or pill.

In another embodiment of this aspect and all other aspects provided herein, the strains of viable, anaerobic gut bacteria are human anaerobic gut bacteria.

In another embodiment of this aspect and all other aspects provided herein, the strains of viable anaerobic gut bacteria are selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile,* and *Veilonella ratti.*

In another embodiment of this aspect and all other aspects provided herein, the strains of viable anaerobic gut bacteria are selected from the group consisting of: *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii,* and *Prevotella tannerae.*

In another embodiment of this aspect and all other aspects provided herein, the strains of viable anaerobic gut bacteria are selected from the group consisting of: (i) *Clostridium ramosum, C. scindens, C. hiranonsis, C. bifermentans, C. leptum,* and *C. sardiniensis,* or (ii) *Bacteroides fragilis, B. thetaiotaomicron, B. ovatus, Parabacteroides goldsteinii,* and *Prevotella tannerae.*

In another embodiment of this aspect and all other aspects provided herein, the strains of viable anaerobic gut bacteria consist essentially of *Clostridium ramosum, C. scindens, C. hiranonsis, C. bifermentans, C. leptum,* and *C. sardiniensis.*

In another embodiment of this aspect and all other aspects provided herein, the strains of viable anaerobic gut bacteria consist essentially of *Bacteroides fragilis*, *B. thetaiotaomicron*, *B. ovatus*, *Parabacteroides goldsteinii*, and *Prevotella tannerae*.

In another embodiment of this aspect and all other aspects provided herein, the strains of viable anaerobic gut bacteria consist essentially of *Clostridium ramosum*, *C. scindens*, *C. hiranonsis*, *C. bifermentans*, *C. leptum*, *C. sardiniensis*, *Bacteroides fragilis*, *B. thetaiotaomicron*, *B. ovatus*, *Parabacteroides goldsteinii*, and *Prevotella tannerae*.

In another embodiment of this aspect and all other aspects provided herein, the strains of viable anaerobic gut bacteria are present in substantially equal biomass.

In another embodiment of this aspect and all other aspects provided herein, the composition is formulated to deliver a dose of at least $1 \times 10^9$ colony forming units (CFUs).

In another embodiment of this aspect and all other aspects provided herein, the composition is formulated to deliver at least $1 \times 10^9$ CFUs in less than 30 capsules per one time dose.

In another embodiment of this aspect and all other aspects provided herein, the composition is frozen for storage.

In another embodiment of this aspect and all other aspects provided herein, the strains of viable anaerobic gut bacteria are encapsulated under anaerobic conditions. In another embodiment of this aspect and all other aspects provided herein, the strains of viable anaerobic gut bacteria are lyophilized under anaerobic conditions.

In another embodiment of this aspect and all other aspects provided herein, wherein anaerobic conditions comprise one or more of the following: (i) oxygen impermeable capsules, (ii) addition of N-acetylcysteine, cysteine or methylene blue to the composition, (iii) use of spores for organisms that sporulate, and (iv) addition of a reducing factor to the composition.

In another embodiment of this aspect and all other aspects provided herein, the enteric-coating comprises a polymer, nanoparticle, fatty acid, shellac, or a plant fiber.

In another embodiment of this aspect and all other aspects provided herein, the composition further comprises a pre-biotic composition.

In another embodiment of this aspect and all other aspects provided herein, the composition is encapsulated, a reconstituted lyophilisate, a food item, or is formulated as a liquid, gel, fluid-gel, or nanoparticles in a liquid.

Another aspect described herein relates to a method for preventing the onset of a food allergy in a subject, the method comprising: administering to a subject a composition as described herein, thereby preventing the onset of a food allergy in the subject.

In one embodiment of this aspect and all other aspects provided herein, the at least 4 strains of gut bacteria administered are selected from the group consisting of: *Clostridium ramosum*, *Clostridium scindens*, *Clostridium hiranonsis*, *Clostridium bifermentans*, *Clostridium leptum*, *Clostridium sardiniensis*, *Bacteroides fragilis*, *Bacteroides thetaiotaomicron*, *Bacteroides ovatus*, *Parabacteroides goldsteinii*, *Prevotella tannerae*, *Clostridum hathewayi*, *Clostridum nexile*, *Clostridium hylemonae*, *Clostridium glycyrrhizinilyticum*, *Clostridium scindens*, *Clostridium lavalense*, *Clostridum fimetarium*, *Clostridium symbiosum*, *Clostridium sporosphaeroides*, *Dialister proprionicfaceins*, *Dialister succinatiphilus*, *Parabacteroides distasonis*, *Parabacteroides goldsteinii*, *Parabacteroides merdae*, *Peptostreptococcus anaerobius*, *Subdoligranulum variabile*, and *Veilonella ratti*.

In another embodiment of this aspect and all other aspects provided herein, the strains of gut bacteria administered are selected from the group consisting of: *Clostridium ramosum*, *C. scindens*, *C. hiranonsis*, *C. bifermentans*, *C. leptum*, *C. sardiniensis*, *Bacteroides fragilis*, *B. thetaiotaomicron*, *B. ovatus*, *Parabacteroides goldsteinii*, and *Prevotella tannerae*.

In another embodiment of this aspect and all other aspects provided herein, the strains of gut bacteria administered are selected from the group consisting of: (i) *Clostridium ramosum*, *C. scindens*, *C. hiranonsis*, *C. bifermentans*, *C. leptum*, and *C. sardiniensis*, or (ii) *Bacteroides fragilis*, *B. thetaiotaomicron*, *B. ovatus*, *Parabacteroides goldsteinii*, and *Prevotella tannerae*.

In another embodiment of this aspect and all other aspects provided herein, the composition is administered by oral administration, enema, suppository, or orogastric tube.

In another embodiment of this aspect and all other aspects provided herein, the minimal microbial consortium or viable, culturable, anaerobic gut bacterial strain(s) is/are isolated and/or purified from a subject known to be tolerant to a selected food allergen.

In another embodiment of this aspect and all other aspects provided herein, the strains of gut bacteria are cultured under anaerobic conditions.

In another embodiment of this aspect and all other aspects provided herein, the anaerobic conditions comprise one or more of the following: (i) oxygen impermeable capsules, (ii) addition of N-acetylcysteine, cysteine, methylene blue, or a reducing factor to the composition, or (iii) use of spores for organisms that sporulate.

In another embodiment of this aspect and all other aspects provided herein, the composition administered further comprises a pre-biotic composition.

In another embodiment of this aspect and all other aspects provided herein, the composition is enteric-coated.

In another embodiment of this aspect and all other aspects provided herein, the treatment administered prevents and/or reverses TH2 programming of Tregs and other mucosal T cell populations.

In another embodiment of this aspect and all other aspects provided herein, the subject is a human subject.

In another embodiment of this aspect and all other aspects provided herein, the method further comprises a step of diagnosing the subject as likely to develop a food allergy.

In another embodiment of this aspect and all other aspects provided herein, the method further comprising a step of testing a fecal sample from the subject for the presence and/or levels of the bacteria in the minimal microbial consortium or the viable, culturable, anaerobic gut bacterial strain(s).

In another embodiment of this aspect and all other aspects provided herein, the food allergy comprises allergy to soy, wheat, eggs, dairy, peanuts, tree nuts, shellfish, fish, mushrooms, stone fruits and other fruits.

In another embodiment of this aspect and all other aspects provided herein, the composition is administered before the first exposure to a potential food allergen.

In another embodiment of this aspect and all other aspects provided herein, the composition is administered upon clinical signs of atopic symptoms.

In another embodiment of this aspect and all other aspects provided herein, the composition is administered to individuals with diagnosed food allergy In another embodiment of this aspect and all other aspects provided herein, the subject is pretreated with an antibiotic.

In another embodiment of this aspect and all other aspects provided herein, the subject is not pretreated with an antibiotic.

Another aspect described herein relates to a method for reducing or eliminating a subject's immune reaction to a food antigen, the method comprising: administering to a subject a composition as described herein, thereby reducing or eliminating a subject's immune reaction to a food allergen.

In one embodiment of this aspect and all other aspects provided herein, the strains of bacteria administered are selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile,* and *Veilonella ratti*.

In another embodiment of this aspect and all other aspects provided herein, the strains of viable gut bacteria are selected from the group consisting of: *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii,* and *Prevotella tannerae*.

In another embodiment of this aspect and all other aspects provided herein, the strains of viable gut bacteria are selected from the group consisting of: (i) *Clostridium ramosum, C. scindens, C. hiranonsis, C. bifermentans, C. leptum,* and *C. sardiniensis,* or (ii) *Bacteroides fragilis, B. thetaiotaomicron, B. ovatus, Parabacteroides goldsteinii,* and *Prevotella tannerae*.

In another embodiment of this aspect and all other aspects provided herein, the composition is administered by oral administration, enema, suppository, or orogastric tube.

In another embodiment of this aspect and all other aspects provided herein, the minimal microbial consortium or the viable, culturable, anaerobic gut bacterial strain(s) is/are isolated and/or purified from a subject known to be tolerant to a selected food allergen.

In another embodiment of this aspect and all other aspects provided herein, the strains of bacteria or minimal microbial consortium is cultured and/or maintained under anaerobic conditions.

In another embodiment of this aspect and all other aspects provided herein, anaerobic conditions comprise one or more of the following: (i) oxygen impermeable capsules, (ii) addition of N-acetylcysteine, cysteine, methylene blue or a reducing factor to the composition, or (iii) use of spores for organisms that sporulate.

In another embodiment of this aspect and all other aspects provided herein, the composition administered further comprises a pre-biotic composition.

In another embodiment of this aspect and all other aspects provided herein, the composition is enteric-coated.

In another embodiment of this aspect and all other aspects provided herein, the treatment prevents and/or reverses TH2 programming of Tregs.

In another embodiment of this aspect and all other aspects provided herein, the subject is a human subject.

In another embodiment of this aspect and all other aspects provided herein, the method further comprises a step of diagnosing the subject as having an IgE-mediated food allergy.

In another embodiment of this aspect and all other aspects provided herein, the method further comprises a step of testing a fecal sample from the subject for the presence and/or levels of the bacteria in the minimal microbial consortium or viable, culturable, anaerobic gut bacterial strain(s).

In another embodiment of this aspect and all other aspects provided herein, the food allergy comprises allergy to soy, wheat, eggs, dairy, peanuts, tree nuts, shellfish, fish, mushrooms, stone fruits or other fruits.

In another embodiment of this aspect and all other aspects provided herein, the composition is administered after an initial exposure and/or reaction to a potential food allergen.

In another embodiment of this aspect and all other aspects provided herein, the biomass of each of the microbes in the administered compositions is greater than the biomass of each of the microbes relative to a reference.

In another embodiment of this aspect and all other aspects provided herein, the subject is pretreated with an antibiotic.

In another embodiment of this aspect and all other aspects provided herein, the subject is not pretreated with an antibiotic.

In another embodiment of this aspect and all other aspects provided herein, the subject is pretreated with a fasting period not longer than 24 hours.

Another aspect provided herein relates to a method of monitoring a subject's microbiome, the method comprising: determining the presence and/or biomass of at least one member of a minimal microbial consortium in a biological sample obtained from a subject, and wherein if the at least one member is absent or the biomass of the at least one member is low relative to a reference, the subject is treated with the composition as described herein.

In another embodiment of this aspect and all other aspects provided herein, the method further comprises predicting that a subject will have an immune response to a food allergen when the at least one member is absent, the biomass of the at least one member is low relative to a reference, or at least one member of a dysbiotic species is present, or is elevated relative to a reference.

In another embodiment of this aspect and all other aspects provided herein, the method is repeated at least one additional time.

In another embodiment of this aspect and all other aspects provided herein, the biological sample is a fecal sample.

Another aspect described herein relates to a synergistic microbial composition comprising: (a) a first microbial consortium consisting essentially of four to six strains of viable, non-pathogenic gut bacteria, wherein the strains of viable non-pathogenic gut bacteria are selected from the group consisting of: *Clostridium ramosum, C. scindens, C. hiranonsis, C. bifermentans, C. leptum,* and *C. sardiniensis,* and (b) a second microbial consortium consisting essentially of four to five strains of viable, non-pathogenic gut bacteria, wherein the strains of viable non-pathogenic gut bacteria are selected from the group consisting of: *Bacteroides fragilis, B. thetaiotaomicron, B. ovatus, Parabacteroides goldsteinii,* and *Prevotella tannerae,* wherein one or more members of the second microbial consortium increases the colonization and/or persistence of one or more members of the first microbial consortium in a mammalian host.

BRIEF DESCRIPTION OF THE FIGURES

FIG. 9. The microbiota of Il4raF709 mice promotes allergic sensitization and anaphylaxis.

FIG. 14. Selected OTUs showing differences between WT and F709 mice: OVA, duodenum, jejunum, ileum.

FIG. 18A-FIG. 18F. Deletion of Il4/Il13 in $T_R$ cells protects against food allergy.

FIG. 21A-FIG. 21I. Gut protect (GP)-I and GP-II are effective in treat-to-prevent food allergy in conventional wild-type and IL4RA F709 mice. FIG. 21A, Conventional IL4raF709 mice are pre-treated with oral broad-spectrum antibiotics 1 week prior to initiating OVA sensitization. Mice receive weekly doses of 5×10⁸ CFU of the aggregate consortia of either GP-1, GP-II or NCC before oral OVA challenge. Mice receive the final OVA challenge at 8 weeks, after which temperature drop (FIG. 21B), from anaphylaxis, impact to IgE titers (FIG. 21C), mast cell protease-1 (FIG. 21D), mast cell recruitment to the small bowel (FIG. 21E), development of Foxp3+ regulatory T cells (FIG. 21F), and total numbers (FIG. 21G), and interferon gamma vs. IL-4 producing T cells (FIGS. 21H & 21I), are measured.

FIG. 23A-FIG. 23H. GP-I and GP-II consortia cure food allergy in conventional IL4raF709 mice while negative control consortia (NCC) does not. FIG. 23A, Conventional IL4raF709 mice are sensitized to OVA for 8 weeks and then given oral antibiotics prior to challenge over 4 weeks with the GP-I (*Clostridiales*), GP-II (*Bacteroidetes*) or NCC (Proteobacteria) consortia. Afterward, mice receive a final OVA challenge and the following analyses: FIG. 23B, temperature changes after OVA challenge as a clinical marker of anaphylaxis. FIG. 23C, Changes to total and OVA-specific IgE titers.

FIG. 23D, MMCP-1 production (indicative of mast cell degranulation). FIGS. 23E & 23F, Effect of consortia on development of mucosal Foxp3+ CD4+ T cells. FIGS. 23G &23H, Effects on IL-4 and interferon gamma (IFNγ) production in mucosal CD4+ T cells.

FIG. 24A-FIG. 24L. GP-II consortia (Bacteriodetes) protects against food allergy without prior antibiotic knockdown of the flora.

FIG. 25A-FIG. 25I. GP-I consortia (*Clostridiales*) can cure food allergy without the use of antibiotics in conventional mice. FIG. 25A, Conventional wild-type or IL4raF709 mice were challenged weekly with OVA for 8 weeks, after which they received 5×10⁸ CFU of the GP-I consortium 8 times over 4 weeks prior to final OVA challenge. Mice received no prior antibiotic knockdown of the underlying microbiota prior to GP-I administration. FIG. 25B, Temperature changes with final OVA challenge. FIG. 25C, Changes in total and OVA-specific IgE titers. FIG. 25D, Changes in percentages of mucosal T cells, Foxp3 regulatory T cells. FIG. 25E, IL4+ mucosal cells and regulatory T cells.

FIGS. 25F & 25G, Changes in CD4+IL-17 production in wild-type and IL4raF709 mice receiving PBS or GP-I consortia. FIGS. 25H & 25I, Changes in IL-17 production of Foxp3+ regulatory cells.

DETAILED DESCRIPTION

Definitions

Figure 1:
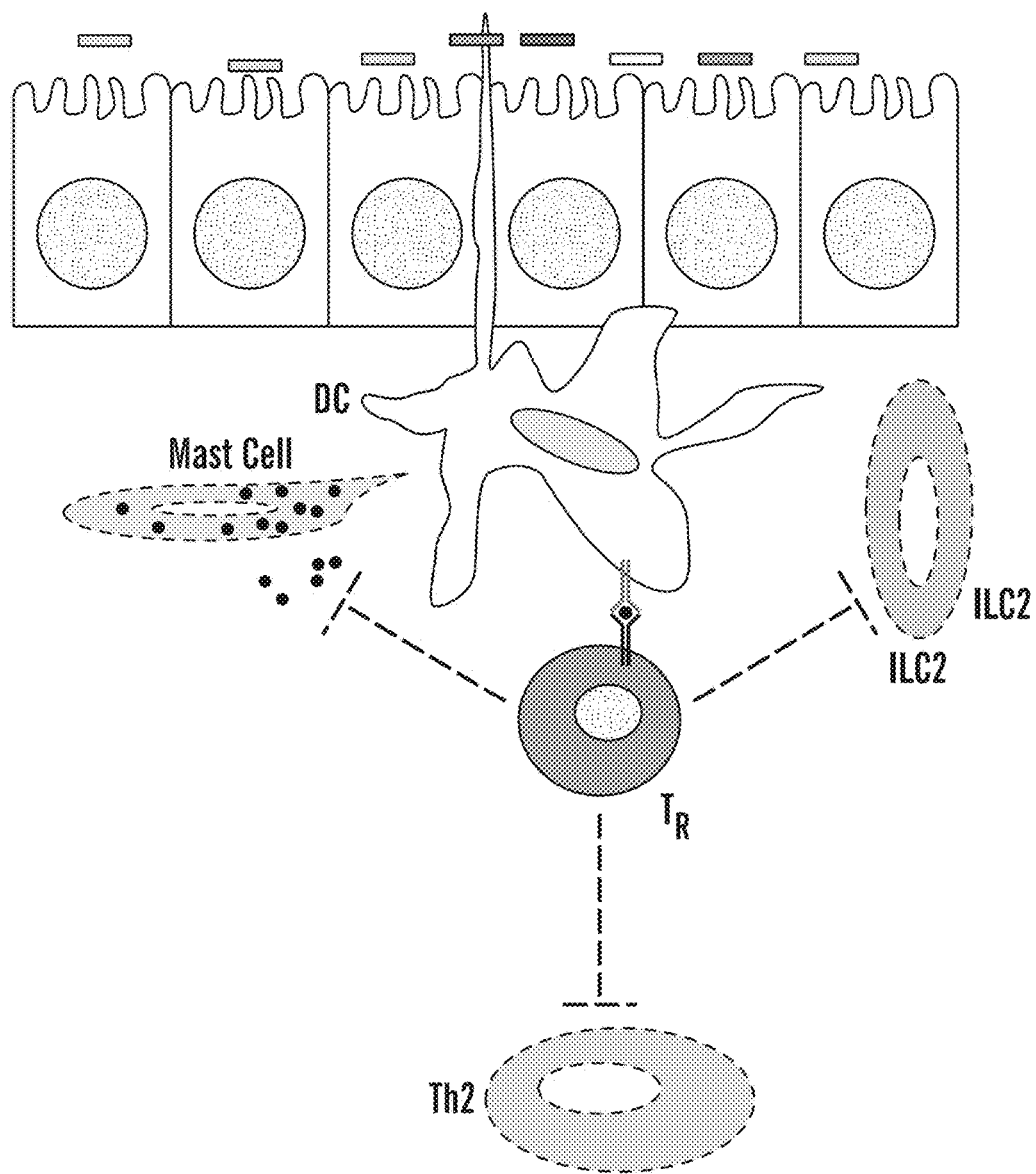
FIG. 1. Tolerance failure in food allergy. Food allergy is a failure of oral tolerance to food antigens associated with Th2 immunity and allergen-specific IgE responses.

As used herein, the term "food allergy" refers to a failure of oral tolerance to food antigens associated with Th2 immunity and allergen-specific IgE responses. That is, an immune response is generated in response to particular food antigens and can lead to hives, gastrointestinal symptoms, abdominal pain, anaphylaxis and even death.

As used herein, the term "microbiota" can refer to the human microbiome, the human microbiota, or the human gut microbiota. The human microbiome (or human microbiota) may be understood as the aggregate of microorganisms that reside on the surface and in deep layers of skin, in the saliva and oral mucosa, in the conjunctiva, and in the genitourinary and gastrointestinal tracts of humans. The human microbiome is comprised of bacteria, fungi, viruses, and archaea. At least some of these organisms perform tasks that are useful for the human host. Under normal circumstances, these microorganisms do not cause acute disease to the human host, but instead cause no harm or participate in maintaining health. Hence, this population of organisms is frequently referred to as the "normal flora." The population of microorganisms living in the human gastrointestinal tract is commonly referred to as "microbial flora", "gut flora", and/or "gut microbiota". The microbial flora of the human gut encompasses a wide variety of microorganisms that aid in digestion, the synthesis of vitamins and other metabolites, and creating enzymes not produced by the human body.

As used herein, the term "minimal microbial consortium" refers to a mixed population of cells comprising at least two species of gut bacteria that do not promote acute disease in a subject. The microbial consortium is "minimal" when an additional bacterial species is added and there is no additional benefit (e.g., less than 5%) in avoiding or mitigating an allergic response. In some embodiments, the minimal microbial consortium comprises at least 3, at least 4, at least 5, at least 6, at least 7, at least 8, at least 9, at least 10, at least 11, or more different species of bacteria. In some embodiments, the minimal microbial consortium comprises at least one species of bacteria from the phyla *Clostridia* and/or *Bacteroidetes*.

"Operational taxonomic unit (OTU, plural OTUs)" refers to a terminal leaf in a phylogenetic tree and is defined by a specific genetic sequence and all sequences that share a specified degree of sequence identity to this sequence at the level of species. A "type" or a plurality of "types" of bacteria includes an OTU or a plurality of different OTUs, and also encompasses a strain, species, genus, family or order of bacteria. The specific genetic sequence may be the 16S rRNA sequence or a portion of the 16S rRNA sequence, or it may be a functionally conserved housekeeping gene found broadly across the eubacterial kingdom. OTUs generally share at least 95%, 96%, 97%, 98%, or 99% sequence identity. OTUs are frequently defined by comparing sequences between organisms. Sequences with less than the specified sequence identity (e.g., less than 97%) are not considered to form part of the same OTU.

"Clade" refers to the set of OTUs or members of a phylogenetic tree downstream of a statistically valid node in a phylogenetic tree. The clade comprises a set of terminal leaves in the phylogenetic tree that is a distinct monophyletic evolutionary unit.

In microbiology, "16S sequencing" or "16S rRNA" or "16S-rRNA" or "16S" refers to sequence derived by characterizing the nucleotides that comprise the 16S ribosomal RNA gene(s). The bacterial 16S rDNA is approximately 1500 nucleotides in length and is used in reconstructing the evolutionary relationships and sequence similarity of one bacterial isolate to a second isolate using phylogenetic approaches. 16S sequences are used for phylogenetic reconstruction as they are in general highly conserved, but contain specific hypervariable regions that harbor sufficient nucleotide diversity to differentiate genera and species of most bacteria, as well as fungi.

The "V1-V9 regions" of the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA by comparing the candidate sequence in question to the reference sequence and identifying the hypervariable regions based on similarity to the reference hypervariable regions.

"Dysbiosis" refers to a state of the microbiota or microbiome of the gut or other body area, including mucosal or skin surfaces in which the normal diversity and/or function of the ecological network is disrupted. Any disruption from the preferred (e.g., ideal) state of the microbiota can be considered a dysbiosis, even if such dysbiosis does not result in a detectable decrease in health. This state of dysbiosis may be unhealthy, it may be unhealthy under only certain conditions, or it may prevent a subject from becoming healthier. Dysbiosis may be due to a decrease in diversity, the overgrowth of one or more pathogens or pathobionts, symbiotic organisms able to cause disease only when certain genetic and/or environmental conditions are present in a patient, or the shift to an ecological network that no longer provides a beneficial function to the host and therefore no longer promotes health.

The terms "patient", "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. In another embodiment, the subject is a domesticated animal including companion animals (e.g., dogs, cats, rats, guinea pigs, hamsters etc.).

As used herein, the term "enteric coated drug delivery device" or "enteric coated composition" refers to any drug delivery method that can be administered orally but is not degraded or activated until the device enters the intestines. Such methods can utilize a coating or encapsulation that is degraded using e.g., pH dependent means, permitting protection of the delivery device and the microbial consortium to be administered or transplanted throughout the upper gastrointestinal tract until the device reaches the alkaline pH of the intestines. In one embodiment, the enteric coated drug delivery device comprises a capsule or a pill. Such drug delivery devices are known to those of skill in the art.

As used herein, a "prebiotic" refers to an ingredient that allows or promotes specific changes, both in the composition and/or activity in the gastrointestinal microbiota that may (or may not) confer benefits upon the host. In some embodiments, a prebiotic can include one or more of the following: fructooligosaccharide, galactooligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carrageenan), oligofructose, oligodextrose, tagatose, resistant maltodextrins (e.g., resistant starch), trans-galactooligosaccharide, pectins (e.g., xylogalactouronan, citrus pectin, apple pectin, and rhamnogalacturonan-I), dietary fibers (e.g., soy fiber, sugarbeet fiber, pea fiber, corn bran, and oat fiber) and xylooligosaccharides.

As used herein, the terms "administering," "introducing" and "transplanting" are used interchangeably in the context of the placement of cells, e.g. a microbial consortium, as described herein into a subject, by a method or route which results in at least partial localization of the introduced cells at a desired site, such as the intestines or a region thereof, such that a desired effect(s) is produced (e.g., tolerance to a food allergen). The cells can be administered by any appropriate route which results in delivery to a desired location in the subject where at least a portion of the delivered cells or components of the cells remain viable. The period of viability of the cells after administration to a subject can be as short as a few hours, e.g., twenty-four hours, to a few days, to as long as several years, i.e., long-term engraftment.

As used herein "preventing" or "prevention" refers to any methodology where the disease state does not occur due to the actions of the methodology (such as, for example, administration of a composition comprising a microbial consortium as described herein). In one aspect, it is understood that prevention can also mean that the disease is not established to the extent that occurs in untreated controls. For example, there can be a 5, 10, 15, 20, 25, 30, 35, 40, 50, 60, 70, 80, 90, or 100% reduction in the establishment of disease frequency relative to untreated controls. Accordingly, prevention of a disease encompasses a reduction in the likelihood that a subject will develop the disease, relative to an untreated subject (e.g. a subject who is not treated with a composition comprising a microbial consortium as described herein).

As used herein, the term "full complement of bile acid transformations" refers to the metabolism of primary bile acids to secondary bile acids. Bile acid transformations performed by gut microbes include deconjugation, deglucuronidation, oxidation of hydroxyl groups, reduction of oxo groups to yield epimeric hydroxyl bile acids, esterification and dehydroxylation. These reactions on bile acids are the full complement of bile acid transformations as the term is used herein.

"Synergy" or "synergistic interactions" refers to the interaction or cooperation of two or more microbes to produce a combined effect greater than the sum of their separate effects. For example, in one embodiment, "synergy" between two or more microbes can result from a first microbe secreting a waste product or metabolite that the second microbe uses to fuel growth or other processes.

As used herein, the term "persistence" refers to the maintenance of one or more members of the microbial consortium in the gastrointestinal tract at a number, biomass or activity that is at or above the threshold for treating and/or preventing food allergy. Persistence can be measured by obtaining a stool sample to determine the number, biomass, and/or activity of one or more members of the microbial consortium. In some embodiments, persistence can be measured by obtaining a ratio of the measured biomass of at least two members of the microbial consortium in the stool sample.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase of a property, level, or other parameter by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" can refer to compounds and compositions which can be administered to a subject (e.g., a mammal or a human) without undue toxicity.

As used herein, the term "pharmaceutically acceptable carrier" can include any material or substance that, when combined with an active ingredient, allows the ingredient to retain biological activity and is non-reactive with the subject's immune system. Examples include, but are not limited to, any of the standard pharmaceutical carriers such as a phosphate buffered saline solution, emulsions such as oil/water emulsion, and various types of wetting agents. The term "pharmaceutically acceptable carriers" excludes tissue culture media.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

It should be understood that this invention is not limited to the particular methodologies, protocols, and reagents, etc., described herein and as such can vary therefrom. The terminology used herein is for the purpose of describing particular embodiments only, and is not intended to limit the scope of the present invention, which is defined solely by the claims.

Microbial Flora

Each individual has a personalized gut microbiota including an estimated 500 to 5000 or more species of bacteria, fungi, viruses, archaea and other microorganisms, up to 100 trillion individual organisms, that reside in the digestive tract, providing a host of useful symbiotic functions, for example, including aiding in digestion, providing nutrition for the colon, producing vitamins, regulating the immune system, assisting in defense against exogenous bacteria, modulating energy metabolism, and the production of short chain fatty acids (SCFAs), e.g., via dietary carbohydrates, including resistant starches and dietary fiber, which are substrates for fermentation that produce SCFAs, primarily acetate, propionate, succinate, butyrate, 1,2 propanediol or 1,3 propanediol as end products.

An imbalance in the microbial flora found in and on the human body is known to be associated with a variety of disease states. For example, obesity in both humans and experimental mouse models is associated with alterations in the intestinal microbiota that appear to be pathogenic. In settings of 'dysbiosis' or disrupted symbiosis, microbiota functions that can be lost or deranged, resulting in increased susceptibility to pathogens, include altered metabolic profiles, or induction of proinflammatory signals that can result in local or systemic inflammation or autoimmunity. In addition, in asthmatic subjects, both the bacterial burden and bacterial diversity were significantly higher as compared to control subjects, which were also correlated with bronchial hyper-responsiveness. Thus, the intestinal microbiota plays a significant role in the pathogenesis of many diseases and disorders, including a variety of pathogenic infections of the gut. For instance, patients become more susceptible to pathogenic infections when the normal intestinal microbiota has been disturbed due to use of broad-spectrum antibiotics. Many of these diseases and disorders are chronic conditions that significantly decrease a patient's quality of life and can be ultimately fatal.

Microbial Consortia

In some embodiments, a microbial consortium comprises at least 4, at least 5, at least 6, at least 7, at least 8, at least 9, at least 10, at least 11, at least 12 or more different viable, bacterial species, e.g., 15 or more, 20 or more, 25 or more, 30 or more, or even 40 or more. In one embodiment, a microbial consortium comprises fewer than 40 species, e.g., 30 or fewer species, 25 or fewer species, 20 or fewer species, or 15 or fewer species. In another embodiment, a minimal microbial consortium comprises 12 or less, 11 or less, 10 or less, 9 or less, 8 or less, 7 or less, 6 or less, 5 or less, or 4 or less different viable bacterial species. In one embodiment, at least one (e.g., at least 2, at least 3, at least 4, at least 5, at least 6, at least 7, at least 8, 8 or fewer, 7 or fewer, 6 or fewer, 5 or fewer, 4 or fewer, 3 or fewer, 2 or fewer) of the bacterial constituents is a non-pathogenic bacterial strain. Also contemplated are consortia of 4 to 40 species, 4 to 30 species, 4 to 25 species, 4 to 20 species, 4 to 15 species, 4 to 11 species, 5 to 40 species, 5 to 30 species, 5 to 25 species, 5 to 20 species, 5 to 15 species, 5 to 11 species, 6 to 40 species, 6 to 30 species, 6 to 25 species, 6 to 20 species, 6 to 15 species, 6 to 11 species, 7 to 40 species, 7 to 30 species, 7 to 25 species, 7 to 20 species, 7 to 15 species, 7 to 11 species, 8 to 40 species, 8 to 30 species, 8 to 25 species, 8 to 20 species, 8 to 15 species, 8 to 11 species, 9 to 40 species, 9 to 30 species, 9 to 25 species, 9 to 20 species, 9 to 15 species, 9 to 11 species, 10 to 40 species, 10 to 30 species, 10 to 25 species, 10 to 20 species, 10 to 15 species, or 10 to 11 species.

In one embodiment, the at least 1 bacterial constituent of a microbial consortium is a bacterial strain(s) of viable gut bacteria selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succi-* *natiphilus, Parabacteroides distasonis, Parabacteroides goldsteinii, Parabacteroides merdae, Peptostreptococcus anaerobius, Subdoligranulum variabile,* and *Veilonella ratti.*

In another embodiment, the strains of viable gut bacteria are selected from the group consisting of: *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii,* and *Prevotella tannerae.*

In another embodiment, the strains of viable gut bacteria are selected from the group consisting of: (i) *Clostridium ramosum, C. scindens, C. hiranonsis, C. bifermentans, C. leptum,* and *C. sardiniensis,* or (ii) *Bacteroides fragilis, B. thetaiotaomicron, B. ovatus, Parabacteroides goldsteinii,* and *Prevotella tannerae.*

In one embodiment, the strains of viable gut bacteria do not include *Escherichia coli, Klebsiella pneumoniae, Proteus mirabilis, Enterobacter cloacae, Bilophila wadsworthia, Alistipes onderdonkii, Desulfovibrio* species, *Lactobacillus johnsoni,* and *Parasutterella excrementihominis.*

In another embodiment, the consortium does not comprise bacteria of the Genera *Bilophila, Enterobacter, Escherichia, Klebsiella, Proteus, Alistipes, Desulfovibrio, Blautia,* or *Parasutterella.*

In another embodiment, the consortium does not comprise bacteria of the Families Desulfovibrionaceae, Enterobacteriaceae, Rikenellaceae, and Sutterellaceae.

In another embodiment, the consortium does not comprise bacteria of the Families Lactobacillaceae or Enterbacteriaceae.

In another embodiment, the consortium does not comprise bacteria of the Order Burkholdales, Desulfovibrionates, or Enterobacteriales.

Metabolic Features:

Various features of gut microbes are beneficial for protection from or therapy for allergy, including food allergy. In the following, features and corresponding functions contemplated to render particular species or taxa of gut microbes well-suited for a protective or therapeutic microbial consortium as described herein are described. In practice, a consortium comprising four or more, e.g., five or more, six or more, seven or more, eight or more, nine or more or ten or more of these features and corresponding functions is considered a likely candidate for protection or therapy for food allergy.

In some embodiments, the microbial consortium comprises one or more types of microbes capable of producing butyrate in a mammalian subject. Butyrate-producing microbes can be identified experimentally, e.g., by NMR or gas chromatography analyses of microbial products or colorimetric assays (Rose I A. 1955. *Methods Enzymol.* 1: 591-5). Butyrate-producing microbes can also be identified computationally, e.g., by the identification of one or more enzymes involved in butyrate synthesis. Non-limiting examples of enzymes found in butyrate-producing microbes include butyrate kinase, phosphotransbutyrylase, and butyryl CoA:acetate CoA transferase (Louis P., et al. 2004. *J Bact.* 186(7): 2099-2106). Butyrate-producing strains include, but are not limited to, *Clostridium sardiniensis, Clostridium hiranonsis, Facealibacterium prausnitzii, Butyrovibrio* spp., *Eubacterium rectale,* and *Roseburia intestinalis.*

In some embodiments, a pharmaceutical composition comprises two or more types of microbes or bacterial strains, wherein the at least two types of microbes are capable of producing butyrate in a mammalian subject. In other embodiments, the composition comprises two or more types of microbes, wherein two or more types of microbe cooperate (i.e., cross-feed) to produce an immunomodulatory short chain fatty acid (SCFA) (e.g., butyrate) in a mammalian subject. In one embodiment, the composition comprises at least one type of microbe (e.g., *Bifidobacterium* spp., *Bacteroides thetaiotaomicron, Bacteroides fragilis* or *Clostridium ramosum*) is capable of metabolizing a prebiotic, including but not limited to, inulin, inulin-type fructans, fucose-containing glycoconjugates including the H1, H2, Lewis A, B, X, or Y antigens, or oligofructose, such that the resulting metabolic product can be converted by a second type of microbe (e.g., a butyrate-producing microbe such as *Roseburia* spp.) to an immunomodulatory SCFA such as butyrate (Falony G., ET al. 2006 Appl. Environ. Microbiol. 72(12): 7835-7841). In other aspects, the composition comprises at least one acetate-consuming, butyrate-producing microbe (e.g., *Faecalibacterium prausnitzii* or *Roseburia intestinalis*).

In some embodiments, the composition comprises one or more types of microbe capable of producing propionate and/or succinate in a mammalian subject, optionally further comprising a prebiotic or substrate appropriate for propionate and/or succinate biosynthesis. Examples of prebiotics or substrates used for the production of propionate include, but are not limited to, L-rhamnose, D-tagalose, resistant starch, inulin, polydextrose, arabinoxylans, arabinoxylan oligosaccharides, mannooligosaccharides, and laminarans (Hosseini E., et al. 2011. *Nutrition Reviews*. 69(5): 245-258). Propionate-producing microbes can be identified experimentally, such as by NMR or gas chromatography analyses of microbial products or colorimetric assays (Rose I A. 1955. *Methods Enzymol.* 1: 591-5). Propionate-producing microbes can also be identified computationally, such as by the identification of one or more enzymes involved in propionate synthesis. Non-limiting examples of enzymes found in propionate-producing microbes include enzymes of the succinate pathway, including but not limited to phosphoenylpyruvate carboxykinase, pyruvate kinase, pyruvate carboxylase, malate dehydrogenase, fumarate hydratase, succinate dehydrogenase, succinyl CoA synthetase, methylmalonyl Coa decarboxylase, and propionate CoA transferase, as well as enzymes of the acrylate pathway, including but not limited to L-lactate dehydrogenase, propionate CoA transferase, lactoyl CoA dehydratase, acyl CoA dehydrogenase, phosphate acetyltransferase, and propionate kinase. For example, microbes that utilize the succinate pathway include certain species of the *Bacteroides* genus, such as *Bacteroides fragilis, Clostridium sardiniensis* and *Clostridum hiranonsis*. In one embodiment, the propionate-producing species is *Bacteroides fragilis, Bacteroides thetaiotaomicron*, or *Bacteroides ovatus*. In one embodiment, the succinate-producing species is *Bacteroides fragilis, Bacteroides thetaiotaomicron*, or *Bacteroides ovatus*.

Functional methods to define species that produce butyrate, propionate and/or succinate includes analysis of short-chain fatty acid (SCFA) production using gas-chromatography/liquid chromatography (GC/LC) to identify propionate, butyrate, and/or succinate or mass spectroscopy based methods to detect these SCFA, as well as 1,2-propanediol, and 1,3-propanediol. Studies can be performed in cultured supernatants from colonized gnotobiotic mice and from conventional patients and/or animal samples.

Additional methods for identifying species that produce butyrate comprise those species expressing butyryl-CoA: acetate CoA transferases (But genes) or butyrate kinases (Buk genes) for production of butyrate from anaerobic fermentation of sugars. In another embodiment, organisms producing butyrate (from amino acids such as lysine, glutarate or 4-aminobutyrate pathways) express enzymes including e.g., L2Hgdh, 2-hydroxyglutarate dehydrogenase; Gct, glutaconate CoA transferase ($\alpha$, $\beta$ subunits); HgCoAd, 2-hydroxy-glutaryl-CoA dehydrogenase ($\alpha$, $\beta$, $\gamma$ subunits); Gcd, glutaconyl-CoA decarboxylase ($\alpha$, $\beta$ subunits); Th1, thiolase; hbd, $\beta$-hydroxybutyryl-CoA dehydrogenase; Cro, crotonase; Bcd, butyryl-CoA dehydrogenase (including electron transfer protein $\alpha$, $\beta$ subunits); KamA, lysine-2,3-aminomutase; KamD,E, $\beta$-lysine-5,6-aminomutase ($\alpha$, $\beta$ subunits); Kdd, 3,5-diaminohexanoate dehydrogenase; Kce, 3-keto-5-aminohexanoate cleavage enzyme; Kal, 3-aminobutyryl-CoA ammonia lyase; AbfH, 4-hydroxybutyrate dehydrogenase; AbfD, 4-hydroxybutyryl-CoA dehydratase; Isom, vinylacetyl-CoA 3,2-isomerase (same protein as AbfD): 4Hbt, butyryl-CoA:4-hydroxybutyrate CoA transferase; But, butyryl-CoA:acetate CoA transferase; Ato, butyryl-CoA:acetoacetate CoA transferase ($\alpha$, $\beta$ subunits); Ptb, phosphate butyryltransferase; Buk, and butyrate kinase (see e.g., Vital et al. mBIO 5(2):e00889-14).

In some embodiments, a microbial consortium comprises at least one bacterial species that produces compounds capable of stimulating the aryl hydrocarbon (AhR) receptor in gut epithelial cells, antigen-presenting cells and/or T cells. Without wishing to be bound by theory, stimulation of the AhR receptor can aid in the development of regulatory T cell processes that can prevent and/or treat food allergy. Some non-limiting examples of compounds that stimulate host aryl hydrocarbon receptor pathways include (i) indole, (ii) intermediates from microbial synthesis of indole, tryptophan, tyrosine and histidine, (iii) microbial synthesis of flavonoids, phenazines and/or quinones or (iv) compounds or intermediates of metabolism of host ingested flavonoids, phenazines and/or quinones. In one example, a viable, culturable, anaerobic gut bacterial strain produces aryl hydrocarbon receptor agonists sufficient to stimulate host aryl hydrocarbon receptor pathways comprises at least one gene associated with the synthesis of tryptophan or the synthesis of quinone molecules. In an additional example, a viable, culturable, anaerobic gut bacterial strain that produces aryl hydrocarbon receptor agonists sufficient to stimulate host aryl hydrocarbon receptor pathways by microbial synthesis of flavonoids, phenazines, and/or quinones. Thus microbes that express or encode biosynthetic enzymes that participate in the synthesis of flavonoids, phenazines and/or quinones are identified as microbes that produce host aryl hydrocarbon receptor agonists. In one embodiment, the biosynthetic enzymes include the last enzyme in the pathway that catalyzes the final biosynthetic reaction producing e.g., flavonoids, phenazine or quinone compounds.

In some embodiments, a microbial consortium comprises at least one bacterial species that produces compounds capable of stimulating the pregnane X receptor that e.g., has beneficial effects on gut barrier function and/or the development of regulatory T cell processes. Non-limiting examples of compounds that stimulate the pregnane X receptor include (i) desmolase, (ii) compounds or intermediates of hydroxysteroid dehydrogenase activity, or (iii) compounds or intermediates derived from flavonoid metabolism enzymes. Thus, bacteria that encode and express steroid desmolase and/or hydroxysteroid dehydrogenase enzymes are expected to produce compounds that stimulate the pregnane X receptor. *Clostridium sardiniensis* and *Clostridium scindens* are non-limiting examples of bacterial species that produce compounds capable of stimulating the pregnane X receptor.

In some embodiments, the microbial consortium comprises at least one bacterial species that produces compounds capable of stimulating the RAR-related orphan receptor gamma (RORgamma) pathways, for example, to stimulate development of regulatory T cell responses via direct stimulation of RORgamma-activated pathways in gut antigen presenting cells and/or epithelial cells that then stimulate regulatory T cell responses. In one embodiment, the viable, culturable, anaerobic gut bacterial strain that produces compounds endogenously or by metabolizing ingested precursors, that is capable of stimulating the RORgamma (RAR-related orphan receptor gamma) pathways to stimulate development of regulatory T cell responses is a strain that expresses at least one cholesterol reductase and other enzymes capable of metabolizing sterol compounds. Non-limiting examples of microbes that produce compounds that stimulate the RORgamma pathway include *Clostridium scindens, Clostridia hiranonsis,* and *Clostridium sardiniensis*. In one instance, those species express bile acid transforming enzymes that can also produce RORgamma pathway agonists.

In some embodiments, a microbial consortium described herein improves gut function, for example, by stimulating host mucins and complex glycoconjugates and improving colonization by protective commensal strains. In one embodiment, the microbial consortium comprises at least one bacterial strain, such as *Bacteroides thetaiotaomicron*, that stimulates production of mucins and complex glycoconjugates by the host.

Immunomodulation:

Other exemplary compositions useful for treatment of food allergy contain bacterial strains capable of altering the proportion of immune subpopulations, e.g., T cell subpopulations, e.g., Tregs in the subject.

For example, immunomodulatory bacteria can increase or decrease the proportion of Treg cells, Th17 cells, Th1 cells, or Th2 cells in a subject. The increase or decrease in the proportion of immune cell subpopulations can be systemic, or it can be localized to a site of action of the colonized consortium, e.g., in the gastrointestinal tract or at the site of a distal dysbiosis. In some embodiments, a microbial consortium comprising immunomodulatory bacteria is used for treatment of food allergy based on the desired effect of the probiotic composition on the differentiation and/or expansion of subpopulations of immune cells in the subject.

In one embodiment, the microbial consortium contains immunomodulatory bacteria that increase the proportion of Treg cells in a subject or in a particular location in a subject, e.g., the gut tissues. In one embodiment, a microbial consortium contains immunomodulatory bacteria that increase the proportion of Th17 cells in a subject. In another embodiment, a microbial consortium contains immunomodulatory bacteria that decrease the proportion of Th17 cells in a subject. In one embodiment, a microbial consortium contains immunomodulatory bacteria that increase the proportion of Th1 cells in a subject. In another embodiment, a microbial consortium contains immunomodulatory bacteria that decrease the proportion of Th1 cells in a subject. In one embodiment, a microbial consortium contains immunomodulatory bacteria that increase the proportion of Th2 cells in a subject. In another embodiment, a microbial consortium contains immunomodulatory bacteria that decrease the proportion of Th2 cells in a subject.

In one embodiment, a microbial consortium contains immunomodulatory bacteria capable of modulating the proportion of one or more of Treg cells, Th17 cells, Th1 cells, Th2 cells, and combinations thereof in a subject. Certain immune cell profiles can be particularly desirable to treat or prevent inflammatory disorders, such as food allergies. For example, in some embodiments, treatment or prevention of e.g., food allergy can be promoted by increasing numbers of Treg cells and Th2 cells, and decreasing numbers of Th17 cells and Th1 cells. Accordingly, a microbial consortium for the treatment or prevention of food allergy can contain a microbial consortium capable of promoting Treg cells and Th2 cells, and reducing Th17 and Th1 cells.

In one embodiment, the anaerobic gut bacterial strain in the methods and compositions described herein express agonists capable of binding to and modulating responses mediated by Toll-like receptors (TLR), CD14 and/or lipid binding proteins in antigen presenting cells, gut epithelial cells and/or T cells to promote the development of regulatory T cells. Non-limiting examples of TLR agonists include lipopolysaccharide (LPS), exopolysaccharides (PSA), peptidoglycan or CpG motifs produced by commensal members of *Bacteroides*, or lipoteichoic acids (LTA) produced by members of *Clostridium*. In one embodiment, an anaerobic gut bacterial strain that acts as a TLR agonist is selected from the following Table.

| Family | Genus | Species |
| --- | --- | --- |
| Clostridieaceae | *Clostridium, Hungatella* | *Hungatella hathawayi* |
| Eubacteriaceae | *Eubacterium* | *Eubacterium rectale* |
| Erysipelotrichaceae | *Erysipelatoclostridium* (formerly species in genus *Clostridium*) | *Erysipelatoclostridium ramosum* (*Clostridium ramosum*) |
| Lachnospiraceae | *Blautia, Butyrovibrio, Cellulosyliticum, Clostridium* cluster XIVa species, *Coprococcus, Dorea, Lachnospira, Robinsonella, Roseburia,* | *Butyrovibrio crossatus, Roseburia intestinalis, Clostridium scindens, Clostridium hylemonae, Clostridium symbiosum* |
| Ruminococcaceae | *Faecalobacterium, Ruminococcus, Subdoligranulum, Clostridium* cluster XIVa species | *Faecalibacterium prausnitzii, Subdoligranulum variabile* |
| Bacteroidaceae | *Bacteroides* | *Bacteroides thetaiotaomicron, Bacteroides fragilis, Bacteroides ovatus* |
| Prophyromonadaceae | *Parabacteroides, Porphyromonas, Tannerella* | *Parabacteroides goldsteinii, Parabacteroides merdae, Parabacteroides distasonis* |
| Prevotellaceae | *Prevotella* | *Prevotella tannerae* |

Bile Acid Transformation:

Primary bile acids (e.g., cholic and chenodeoxycholic acids in humans) are generated in the liver of mammals, including humans, mainly by conjugation with the amino acids taurine or glycine, and are secreted in bile. In the intestinal tract, primary bile acids are metabolized by microbes that transform the primary bile acids to secondary bile acids. Intestinal microbial transformation of primary bile acids can include deconjugation, deglucuronidation, oxidation of hydroxyl groups, reduction of oxo groups to yield epimeric hydroxyl bile acids, esterification, and dehydroxylation. Non-limiting examples of bacteria that perform deconjugation of primary bile acids include *Bacteroides, Bifidobacterium, Clostridium,* and *Lactobacillus*. Non-limiting examples of bacteria that perform oxidation and epimerization of primary bile acids include *Bacteroides,*

*Clostridium, Egghertella, Eubacterium, Peptostreptococcus*, and *Ruminococcus*. Non-limiting examples of bacteria that perform 7-dehydroxylation of primary bile acids include *Clostridium*, and *Eubacterium*. Non-limiting examples of bacteria that perform esterification of primary bile acids include *Bacteroides, Eubacterium*, and *Lactobacillus*.

In one embodiment, a microbial consortium as described herein comprises at least one bacterial constituent that transforms bile acids by deconjugation. In another embodiment, a microbial consortium as described herein comprises at least one bacterial constituent that transforms bile acids by 7-dehydroxylation. In another embodiment, a microbial consortium as described herein comprises at least one bacterial constituent that transforms bile acids by esterification.

In one embodiment, a microbial consortium as described herein comprises at least 2, at least 3, at least 4, at least 5, at least 6, at least 7, at least 8, at least 9, at least 10, at least 11 or more bacterial constituents that perform bile acid transformation.

In one embodiment, a microbial consortium as described herein comprises 11 or fewer, 10 or fewer, 9 or fewer, 8 or fewer, 7 or fewer, 6 or fewer, 5 or fewer, 4 or fewer, 3 or fewer, 2 or fewer 1 or fewer or zero bacterial constituents that perform bile acid transformation, such as deconjugation, esterification or 7-dehydroxylation.

In one embodiment, a microbial consortium comprises at least one anaerobic gut bacterial strain that alone, or in combination, performs the full complement of bile acid transformations.

Engineered Microbes:

In some embodiments, one or more members of the microbial consortium comprises an engineered microbe(s). For example, engineered microbes include microbes harboring i) one or more introduced genetic changes, such change being an insertion, deletion, translocation, or substitution, or any combination thereof, of one or more nucleotides contained on the bacterial chromosome or on an endogenous plasmid, wherein the genetic change can result in the alteration, disruption, removal, or addition of one or more protein coding genes, non-protein-coding genes, gene regulatory regions, or any combination thereof, and wherein such change can be a fusion of two or more separate genomic regions or can be synthetically derived; ii) one or more foreign plasmids containing a mutant copy of an endogenous gene, such mutation being an insertion, deletion, or substitution, or any combination thereof, of one or more nucleotides; and iii) one or more foreign plasmids containing a mutant or non-mutant exogenous gene or a fusion of two or more endogenous, exogenous, or mixed genes. The engineered microbe(s) can be produced using techniques including but not limited to site-directed mutagenesis, transposon mutagenesis, knock-outs, knock-ins, polymerase chain reaction mutagenesis, chemical mutagenesis, ultraviolet light mutagenesis, transformation (chemically or by electroporation), phage transduction, or any combination thereof.

Excluded Bacteria:

In one embodiment, a microbial consortium does not include an organism conventionally classified as a pathogenic or opportunistic organism. It is possible that a function shared by all members of a given taxonomic group could be beneficial, e.g., for providing particular metabolites, yet for other reasons the overall effect of one or more particular members of the group is not beneficial and is, for example, pathogenic. Clearly, members of a given taxonomic group that cause pathogenesis, e.g., acute gastrointestinal pathologies, are to be excluded from the therapeutic or preventive methods and compositions described herein.

In one embodiment, the bacterial composition does not comprise at least one of: *Acidaminococcus intestinalis, Escherichia coli, Lactobacillus casei, Lactobacillus paracasei, Raoultella* sp., and *Streptococcus mitis*.

In another embodiment, the bacterial composition does not comprise at least one of *Barnesiella intestinihominis; Lactobacillus reuteri; Enterococcus hirae, Enterococus faecium*, or *Enterococcus durans; Anaerostipes caccae* or *Clostridium indolis; Staphylococcus wameri* or *Staphylococcus pasteuri*; and *Adlercreutzia equolifaciens*.

In another embodiment, the bacterial composition does not comprise at least one of *Clostridium botulinum, Clostridium cadaveric, Clostridium chauvoei, Clostridium clostridioforme, Clostridium cochlearium, Clostridium difficile, Clostridium haemolyticum, Clostridium hastiforme, Clostridium histolyticum, Clostridium indolis, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium septicum, Clostridium sordellii, Clostridium sphenoides*, and *Clostridium tetani*.

In another embodiment, the bacterial composition does not comprise at least one of *Escherichia coli*, and *Lactobacillus johnsonii*.

In another embodiment, the bacterial composition does not comprise at least one of *Clostridium innocuum, Clostridium butyricum, Escherichia coli*, and *Blautia producta* (previously known as *Peptostreptococcus productus*).

In another embodiment, the bacterial composition does not comprise at least one of *Eubacteria, Fusobacteria, Propionibacteria, Escherichia coli*, and *Gemmiger*.

In another embodiment, the compositions described herein do not comprise pathogenic bacteria such as e.g., *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Chlamydia, Chlamydophila, Campylobacter, Burkholderia, Brucella, Borrelia, Bordetella, Bacillus*, multi-drug resistant bacteria, extended spectrum beta-lactam resistant Enterococci (ESBL), Carbapenem-resistant Enterobacteriaceae (CRE), and vancomycin-resistant Enterococci (VRE).

In other embodiments, the compositions described herein do not comprise pathogenic species or strains, such as *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (such as, but not limited to, LT and/or ST), *Escherichia coli* O157:H7, *Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnificus*, and *Yersinia enterocolitica*.

In one embodiment, the microbial consortia and compositions thereof do not comprise *Escherichia coli, Klebsiella pneumoniae, Proteus mirabilis, Enterobacter cloacae*, and/or *Bilophila wadsworthia*.

Reduction of Pathogenic Organisms:

In some embodiments, compositions comprising a microbial consortium as described herein offer a protective or therapeutic effect against dysbiosis or against infection by one or more GI pathogens of interest. In one embodiment, a microbial consortium as described herein reduces the biomass of one or more dysbiotic or pathogenic bacterial strains.

In one embodiment, a microbial consortium as described herein decreases the biomass of one or more dysbiotic or pathogenic bacterial strains by at least 10% compared to the biomass of the one or more dysbiotic or pathogenic bacterial strains in the absence of treatment with such microbial consortium. In other embodiments the biomass of one or more pathogenic bacterial strains is decreased by at least 20%, at least 30%, at least 40%, at least 50%, at least 60%, at least 70%, at least 80%, at least 90%, at least 95%, at least 99%, or even 100% (i.e., below detectable limits of the assay) as compared to the biomass of the dysbiotic or pathogenic bacterial strains in the gut of the subject prior to treatment with the microbial consortium or compositions thereof.

In some embodiments, a microbial consortium as described herein alters the gut environment such that the number, biomass, or activity of one or more dysbiotic or pathogenic organisms is decreased by at least 10% (e.g., at least 20%, at least 30%, at least 40%, at least 50%, at least 60%, at least 70%, at least 80%, at least 90%, at least 95%, at least 99%, or even 100% (i.e., below detectable limits of the assay)). As but one example, colonization of *Bacteroides* reduces the biomass of dysbiotic species in the Enterobacteriaceae or Desulfonovibriacaea Families.

In some embodiments, the pathogenic bacterium is selected from the group consisting of *Yersinia, Vibrio, Treponema, Streptococcus, Staphylococcus, Escherichia/Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus, Bilophila, Desulfovibrio*, multi-drug resistant bacteria, extended spectrum beta-lactam resistant Enterococci (ESBL), Carbapenem-resistant Enterobacteriaceae (CRE), and vancomycin-resistant Enterococci (VRE).

In some embodiments, these pathogens include, but are not limited to, *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, entero hemorrhagic *Escherichia coli*, enteroinvasive *Escherichia coli*, enterotoxigenic *Escherichia coli* (such as, but not limited to, LT and/or ST), *Escherichia coli* O157:H7, *Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus* spp., *Staphylococcus aureus*, vancomycin-resistant *enterococcus* spp., *Vibrio* spp., *Vibrio cholerae, Vibrio parahaemolyticus, Vibrio vulnificus*, and *Yersinia enterocolitica*.

In one embodiment, the pathogen of interest is at least one pathogen chosen from *Clostridium difficile, Salmonella* spp., pathogenic *Escherichia coli*, vancomycin-resistant *Enterococcus* spp., and extended spectrum beta-lactam resistant Enterococci (ESBL).

Methods for testing the efficacy of the compositions comprising a microbial composition to reduce the number, biomass, or activity of one or more dysbiotic or pathogenic organisms are discussed in the following. While certain of the methods are described in the following in terms of assaying reduced number, biomass or activity of *C. difficile*, one of skill in the art can readily adapt the methods to measure the number, biomass or activity of one or more further microbial strains.

In one embodiment, provided is an In Vitro Assay utilizing competition between the bacterial compositions or subsets thereof and *C. difficile* or other dysbiotic or pathogenic strain. This test in known in the art and as such is not described in detail herein.

In another embodiment, provided is an In Vitro Assay utilizing 10% (wt/vol) Sterile-Filtered Feces. This assay tests for the protective effect of the bacterial compositions and screens in vitro for combinations of microbes that inhibit the growth of a given pathogenic or dysbiotic microbe. The assay can operate in automated high-throughput or manual modes. Under either system, human or animal feces can be re-suspended in an anaerobic buffer solution, such as pre-reduced PBS or other suitable buffer, the particulate removed by centrifugation, and filter sterilized. This 10% sterile-filtered feces material serves as the base media for the in vitro assay. To test a bacterial composition, an investigator can add it to the sterile-filtered feces material for a first incubation period and then can inoculate the incubated microbial solution with a pathogenic or dysbiotic microbe of interest for a second incubation period. The resulting titer of the pathogenic or dysbiotic microbe is quantified by any number of methods such as those described below, and the change in the amount of pathogen is compared to standard controls including the pathogenic or dysbiotic microbe cultivated in the absence of the bacterial composition. The assay is conducted using at least one control. Feces from a healthy subject can be used as a positive control. As a negative control, antibiotic-treated feces or heat-treated feces can be used. Various bacterial compositions can be tested in this material and the bacterial compositions optionally compared to the positive and/or negative controls. The ability to inhibit the growth of a pathogenic or dysbiotic microbe can be measured by plating the incubated material on selective media and counting colonies. After competition between the bacterial composition and the pathogenic or dysbiotic microbe, each well of the in vitro assay plate is serially diluted ten-fold six times, and plated on selective media. For *Clostridium difficile* this would include, for example, cycloserine cefoxitin mannitol agar (CCMA) or cycloserine cefoxitin fructose agar (CCFA), and incubated. Colonies of the pathogenic or dysbiotic microbes are then counted to calculate the concentration of viable cells in each well at the end of the competition.

Alternatively, the ability to inhibit the growth of a pathogenic or dysbiotic species can be measured by quantitative PCR (qPCR). Standard techniques can be followed to generate a standard curve for the pathogenic or dysbiotic strain of interest. Genomic DNA can be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions. The qPCR can be conducted using HotMasterMix (SPRIME, Gaithersburg, Md.) and primers specific for the pathogenic or dysbiotic microbe of interest, and can be conducted on a MicroAmp® Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (BioRad, Hercules, Calif.), with fluorescent readings of the FAM and ROX channels. The Cq value for each well on the FAM channel is determined by the CFX Manager™ software version 2.1. The $\log_{10}$ (cfu/ml) of each experimental sample is calculated by inputting a given sample's Cq value into linear regression model generated from the standard curve comparing the Cq values of the standard curve wells to the known $\log_{10}$ (cfu/ml) of those samples. The skilled artisan can employ alternative qPCR modes.

Also provided are In Vivo Assays establishing the protective effect of bacterial compositions. The assay is described in terms of protective effect against *Clostridium difficile*, but can be adapted by one of skill in the art for other pathogens or dysbiotic species. Provided is an in vivo mouse model to test for the protective effect of the bacterial compositions against *C. difficile*. In this model (based on Chen, et al., Gastroenterology 135(6):1984-1992 (2008)), mice are made susceptible to *C. difficile* by a 7 day treatment (days −12 to −5 of experiment) with 5 to 7 antibiotics (including kanamycin, colistin, gentamycin, metronidazole and vancomycin and optionally including ampicillin and ciprofloxacin) delivered via their drinking water, followed by a single dose with Clindamycin on day −3, then challenged three days later on day 0 with $10^4$ spores of *C. difficile* via oral gavage (i.e., oro-gastric lavage). Bacterial compositions can be given either before (prophylactic treatment) or after (therapeutic treatment) *C. difficile* gavage. Further, bacterial compositions can be given after (optional) vancomycin treatment to assess their ability to prevent recurrence and thus suppress the pathogen in vivo. The outcomes assessed each day from day −1 to day 6 (or beyond, for prevention of recurrence) are weight, clinical signs, mortality and shedding of *C. difficile* in the feces. Weight loss, clinical signs of disease and *C. difficile* shedding are typically observed without treatment. Vancomycin provided by oral gavage on days −1 to 4 protects against these outcomes and serves as a positive control. Clinical signs are subjective, and scored each day by the same experienced observer. Animals that lose greater than or equal to 25% of their body weight are euthanized and counted as infection-related mortalities. Feces are gathered from mouse cages (5 mice per cage) each day, and the shedding of *C. difficile* spores is detected in the feces using a selective plating assay as described for the in vitro assay above, or via qPCR for the toxin gene. The effects of test materials including 10% suspension of human feces (as a positive control), bacterial compositions, or PBS (as a negative vehicle control), are determined by introducing the test article in a 0.2 mL volume into the mice via oral gavage on day −1, one day prior to *C. difficile* challenge, on day 1, 2 and 3 as treatment or post-vancomycin treatment on days 5, 6, 7 and 8. Vancomycin, as discussed above, is given on days 1 to 4 as another positive control. Alternative dosing schedules and routes of administration (e.g. rectal) may be employed, including multiple doses of test article, and $10^3$ to $10^{13}$ of a given organism or composition may be delivered.

Enhancement of Beneficial Organisms:

In some embodiments, compositions comprising a microbial consortium offer a therapeutic effect of enhancing beneficial organisms in the GI tract. In one embodiment, a microbial consortium as described herein increases the biomass of one or more beneficial bacterial strains by at least 10%. In other embodiments the biomass of one or more beneficial bacterial strains is increased by at least 20%, at least 30%, at least 40%, at least 50%, at least 60%, at least 70%, at least 80%, at least 90%, at least 1-fold, at least 2-fold, at least 5-fold, at least 10-fold, at least 50-fold, at least 100-fold, at least 500-fold, at least 1000-fold, at least 5000-fold, at least 10,000-fold, at least 15,000-fold or at least 20,000-fold over the biomass of the beneficial bacterial strains in the gut of the subject prior to treatment with the microbial consortium or compositions thereof. In one embodiment, the beneficial organisms are commensal bacterial strains that currently reside or exist in the gut. In another embodiment, the beneficial organisms are one or more of the bacterial strains in the microbial consortium itself.

In some embodiments, a microbial consortium as described herein alters the gut environment such that the number, biomass, or activity of one or more beneficial organisms is increased by at least 10% (e.g., by at least 20%, at least 30%, at least 40%, at least 50%, at least 60%, at least 70%, at least 80%, at least 90%, at least 1-fold, at least 2-fold, at least 5-fold, at least 10-fold, at least 50-fold, at least 100-fold, at least 500-fold, at least 1000-fold, at least 5000-fold, at least 10,000-fold, at least 15,000-fold or at least 20,000-fold). For example, the microbial consortium stimulates the host's production of mucins and complex glycoconjugates to improve gut barrier function and colonization of beneficial organisms, additional probiotic compositions, or the microbial consortium itself. In some embodiments, the microbial composition for enhancing the biomass and/or activity of beneficial organisms comprises e.g., *Bacteroides thetaiotaomicron*, which enhances colonization by other *Bacteroidetes* and *Clostridiales*. In some embodiments, the microbial consortium influences gut pH, reduction of oxygen tension, secretion of glycosidases, and improving the reduction potential of the gut lumen to improve the colonization of beneficial organisms.

In another embodiment, the beneficial species comprises a *Clostridium* spp, such as *Clostridium ramosum*, *Clostridium scindens*, *Clostridium hiranonsis*, *Clostridium bifermentans*, *Clostridium leptum*, *Clostridium sardiniensis*, *Clostridium hathewayi*, *Clostridium nexile*, *Clostridium hylemonae*, *Clostridium glycyrrhizinilyticum*, *Clostridium lavalense*, *Clostridium fimetarium*, *Clostridium symbiosum*, or *Clostridium sporosphaeroides*.

Characterization of Bacteria and Bacterial Consortia

In certain embodiments, methods are provided for testing certain characteristics of compositions comprising a microbial consortium. For example, the sensitivity of bacterial compositions to certain environmental variables is determined, e.g., in order to select for particular desirable characteristics in a given composition, formulation and/or use. For example, the bacterial constituents of the composition can be tested for pH resistance, bile acid resistance, and/or antibiotic sensitivity, either individually on a constituent-by-constituent basis or collectively as a bacterial composition comprised of multiple bacterial constituents (collectively referred to in this section as a microbial consortium).

pH Sensitivity Testing:

If a pharmaceutical composition will be administered other than to the colon or rectum (i.e., for example, an oral route), optionally testing for pH resistance enhances the selection of microbes or therapeutic compositions that will survive at the highest yield possible through the varying pH environments of the distinct regions of the GI tract or genitourinary tracts. Understanding how the bacterial compositions react to the pH of the GI or genitourinary tracts also assists in formulation, so that the number of microbes in a dosage form can be increased if beneficial and/or so that the composition can be administered in an enteric-coated capsule or tablet or with a buffering or protective composition.

As the pH of the stomach can drop to a pH of 1 to 2 after a high-protein meal for a short time before physiological mechanisms adjust it to a pH of 3 to 4 and often resides at a resting pH of 4 to 5, and as the pH of the small intestine can range from a pH of 6 to 7.4, bacterial compositions can be prepared that survive these varying pH ranges (specifically wherein at least 1%, 5%, 10%, 15%, 20%, 25%, 30%, 40%, 50%, 60%, 70%, 80%, 90%, or as much as 100% of the bacteria can survive gut transit times through various pH ranges). This can be tested by exposing the bacterial composition to varying pH ranges for the expected gut transit times through those pH ranges. Therefore, as a non-limiting example only, 18-hour cultures of compositions comprising one or more bacterial species or strains can be grown in standard media, such as gut microbiota medium ("GMM", see Goodman et al., PNAS 108(15):6252-6257 (2011)) or another animal-products-free medium, with the addition of pH adjusting agents for a pH of 1 to 2 for 30 minutes, a pH of 3 to 4 for 1 hour, a pH of 4 to 5 for 1 to 2 hours, and a pH of 6 to 7.4 for 2.5 to 3 hours. An alternative method for testing stability to acid is described in e.g., U.S. Pat. No. 4,839,281. Survival of bacteria can be determined by culturing the bacteria and counting colonies on appropriate selective or non-selective media.

Bile Acid Sensitivity Testing:

Additionally, in some embodiments, testing for bile-acid resistance enhances the selection of microbes or therapeutic compositions that will survive exposures to bile acid during transit through the GI tract. Bile acids are secreted into the small intestine and can, like pH, affect the survival of bacterial compositions. This can be tested by exposing the compositions to bile acids for the expected gut exposure time to bile acids. For example, bile acid solutions can be prepared at desired concentrations using 0.05 mM Tris at pH 9 as the solvent. After the bile acid is dissolved, the pH of the solution can be adjusted to 7.2 with 10% HCl. Bacterial components of the therapeutic compositions can be cultured in 2.2 ml of a bile acid composition mimicking the concentration and type of bile acids in the patient, 1.0 ml of 10% sterile-filtered feces media and 0.1 ml of an 18-hour culture of the given strain of bacteria. Incubations can be conducted for from 2.5 to 3 hours or longer. An alternative method for testing stability to bile acid is described in e.g., U.S. Pat. No. 4,839,281. Survival of bacteria can be determined by culturing the bacteria and counting colonies on appropriate selective or non-selective media.

Antibiotic Sensitivity Testing:

As a further optional sensitivity test, the bacterial components of the microbial compositions can be tested for sensitivity to antibiotics. In one embodiment, the bacterial components can be chosen so that they are sensitive to antibiotics such that if necessary they can be eliminated or substantially reduced from the patient's gastrointestinal tract by at least one antibiotic targeting the bacterial composition.

Adherence to Gastrointestinal Cells:

The compositions can optionally be tested for the ability to adhere to gastrointestinal cells. A method for testing adherence to gastrointestinal cells is described in e.g., U.S. Pat. No. 4,839,281.

Identification of Immunomodulatory Bacteria: In some embodiments, immunomodulatory bacteria are identified by the presence of nucleic acid sequences that modulate sporulation. In particular, signature sporulation genes are highly conserved across members of distantly related genera including *Clostridium* and *Bacillus*. Traditional approaches of forward genetics have identified many, if not all, genes that are essential for sporulation (spo). The developmental program of sporulation is governed in part by the successive action of four compartment-specific sigma factors (appearing in the order σF, σE, σG and σK), whose activities are confined to the forespore (σF and σG) or the mother cell (σE and σK). In other embodiments, immunomodulatory bacteria are identified by the biochemical activity of DPA producing enzymes or by analyzing DPA content of cultures. As part of the bacterial sporulation, large amounts of DPA are produced, and comprise 5-15% of the mass of a spore. Because not all viable spores germinate and grow under known media conditions, it is difficult to assess a total spore count in a population of bacteria. As such, a measurement of DPA content highly correlates with spore content and is an appropriate measure for characterizing total spore content in a bacterial population.

In other embodiments, immunomodulatory bacteria are identified by screening bacteria to determine whether the bacteria induce secretion of pro-inflammatory or anti-inflammatory cytokines by host cells. For example, human or mammalian cells capable of cytokine secretion, such as immune cells (e.g., PBMCs, macrophages, T cells, etc.) can be exposed to candidate immunomodulatory bacteria, or supernatants obtained from cultures of candidate immunomodulatory bacteria, and changes in cytokine expression or secretion can be measured using standard techniques, such as ELISA, immunoblot, Luminex™, antibody array, quantitative PCR, microarray, etc. Bacteria can be selected for inclusion in a microbial consortium based on the ability to induce a desired cytokine profile in human or mammalian cells. For example, anti-inflammatory bacteria can be selected for inclusion (or alternatively exclusion) in a microbial consortium or composition thereof, based on the ability to induce secretion of one or more anti-inflammatory cytokines, and/or the ability to reduce secretion of one or more pro-inflammatory cytokines. Anti-inflammatory cytokines include, for example, IL-10, IL-13, IL-9, IL-4, IL-5, and combinations thereof. Other inflammatory cytokines include, for example, TGFβ. Pro-inflammatory cytokines include, for example, IFNγ, IL-12p70, IL-1α, IL-6, IL-8, MCP1, MIP1α, MIP1β, TNFα, and combinations thereof. In some embodiments, anti-inflammatory bacteria can be selected for inclusion in a microbial consortium based on the ability to modulate secretion of one or more anti-inflammatory cytokines and/or the ability to reduce secretion of one or more pro-inflammatory cytokines by a host cell induced by a bacteria of a different type (e.g., a bacteria from a different species or from a different strain of the same species).

In other embodiments, immunomodulatory bacteria are identified by screening bacteria to determine whether the bacteria impact the differentiation and/or expansion of particular subpopulations of immune cells. For example, candidate bacteria can be screened for the ability to promote differentiation and/or expansion of Treg cells, Th17 cells, Th1 cells and/or Th2 cells from precursor cells, e.g. naive T cells. By way of example, naïve T cells can be cultured in the presence of candidate bacteria or supernatants obtained from cultures of candidate bacteria, and numbers of Treg cells, Th17 cells, Th1 cells and/or Th2 cells can be determined using standard techniques, such as FACS analysis. Markers indicative of Treg cells include, for example, $CD25^+CD127^{lo}$. Markers indicative of Th17 cells include, for example, $CXCR3^-CCR6^+$. Markers indicative of Th1 cells include, for example, $CD4^+$, $CXCR3^+$, and $CCR6^-$. Markers indicative of Th2 cells include, for example, $CD4^+$, $CCR4^+$, and $CXCR3^-$, $CCR6^-$. Other markers indicative of particular T cells subpopulations are known in the art, and may be used in the assays described herein, e.g., to identify populations of immune cells impacted by candidate immunomodulatory bacteria. Bacteria can be selected for inclusion (or exclusion) in a microbial consortium based on the ability to promote differentiation and/or expansion of a desired immune cell subpopulation.

In other embodiments, immunomodulatory bacteria are identified by screening bacteria to determine whether the bacteria secrete short chain fatty acids (SCFA), such as, for example, butyrate, acetate, propionate, or valerate, or combinations thereof. For example, secretion of short chain fatty acids into bacterial supernatants can be measured using standard techniques. In one embodiment, bacterial supernatants can be screened to measure the level of one or more short chain fatty acids using NMR, mass spectrometry (e.g., GC-MS, tandem mass spectrometry, matrix-assisted laser desorption/ionization, etc.), ELISA, or immunoblot. Expression of bacterial genes responsible for production of short chain fatty acids can also be determined by standard techniques, such as Northern blot, microarray, or quantitative PCR.

Exemplary minimal microbial consortia: Minimal microbial consortia are shown herein in the Examples section and can prevent and/or treat existing symptoms of a food allergy. These exemplary minimal microbial consortia should not be construed as limiting and are intended only for the better understanding of the methods and compositions described herein.

In one embodiment, a minimal microbial consortium consists essentially of: *Clostridum ramosum, C. scindens, C. hiranonsis, C. bifermentans, C. leptum* and *C. sardiniensis.*

In one embodiment, a minimal microbial consortium consisting essentially of: *Clostridum ramosum, C. scindens, C. hiranonsis, C. bifermentans, C. leptum* and *C. sardiniensis* is used in the prevention and/or treatment of existing allergic reactions to food.

In one embodiment, a minimal microbial consortium consists essentially of: *Bacteroides fragilis, B. thetaiotaomicron, B. ovatus, Parabacteroides goldsteinii,* and *Prevotella tannerae.*

In one embodiment, a minimal microbial consortium consisting essentially of: *Bacteroides fragilis, B. thetaiotaomicron, B. ovatus, Parabacteroides goldsteinii,* and *Prevotella tannerae* is used to treat existing allergic reactions to food.

By "consists essentially of" in this context is meant that if the addition of another microbe does not improve the treatment or prevention of allergy as described and defined herein, that microbe is not essential to the protective or therapeutic effect.

Prebiotics

A prebiotic is a selectively fermented ingredient that allows specific changes, both in the composition and/or activity in the gastrointestinal microbiota, that confers neutral or positive benefits upon host well-being and health. Prebiotics can include complex carbohydrates, amino acids, peptides, or other nutritional components useful for the survival, colonization and persistence of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Suitable prebiotics are usually plant-derived complex carbohydrates, oligosaccharides or polysaccharides. Generally, prebiotics are indigestible or poorly digested by humans and serve as a food source for bacteria. Prebiotics, which can be used in the pharmaceutical dosage forms, and pharmaceutical compositions provided herein include, without limitation, galactooligosaccharides (GOS), trans-galactooligosaccharides, fructooligosaccharides or oligofructose (FOS), inulin, oligofructose-enriched inulin, lactulose, arabinoxylan, xylooligosaccharides (XOS), mannooligosaccharides, gum guar, gum Arabic, tagatose, amylose, amylopectin, xylan, pectin, and the like and combinations of thereof. Prebiotics can be found in certain foods, e.g., chicory root, Jerusalem artichoke, Dandelion greens, garlic, leek, onion, asparagus, wheat bran, wheat flour, banana, milk, yogurt, sorghum, burdock, broccoli, Brussels sprouts, cabbage, cauliflower, collard greens, kale, radish and rutabaga, and miso. Alternatively, prebiotics can be purified or chemically or enzymatically synthesized.

In some embodiments, the composition comprises at least one prebiotic. In one embodiment, the prebiotic is a carbohydrate. In some embodiments, the composition comprises a prebiotic mixture, which comprises at least one carbohydrate. A "carbohydrate" refers to a sugar or polymer of sugars. The terms "saccharide," "polysaccharide," "carbohydrate," and "oligosaccharide" can be used interchangeably. Most carbohydrates are aldehydes or ketones with many hydroxyl groups, usually one on each carbon atom of the molecule. Carbohydrates generally have the molecular formula $(CH_2O)n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates can contain modified saccharide units, such as 2'-deoxyribose wherein a hydroxyl group is removed, 2'-fluororibose wherein a hydroxyl group is replaced with a fluorine, or N-acetylglucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers. Carbohydrates can be purified from natural (e.g., plant or microbial) sources (i.e., they are enzymatically synthesized), or they can be chemically synthesized or modified.

Suitable prebiotic carbohydrates can include one or more of a carbohydrate, carbohydrate monomer, carbohydrate oligomer, or carbohydrate polymer. In certain embodiments, the pharmaceutical composition or dosage form comprises at least one type of microbe and at least one type of non-digestible saccharide, which includes non-digestible monosaccharides, non-digestible oligosaccharides, or non-digestible polysaccharides. In one embodiment, the sugar units of an oligosaccharide or polysaccharide can be linked in a single straight chain or can be a chain with one or more side branches. The length of the oligosaccharide or polysaccharide can vary from source to source. In one embodiment, small amounts of glucose can also be contained in the chain. In another embodiment, the prebiotic composition can be partially hydrolyzed or contain individual sugar moieties that are components of the primary oligosaccharide (see e.g., U.S. Pat. No. 8,486,668).

Prebiotic carbohydrates can include, but are not limited to monosaccharides (e.g., trioses, tetroses, pentoses, aldopentoses, ketopentoses, hexoses, cyclic hemiacetals, ketohexoses, heptoses) and multimers thereof, as well as epimers, cyclic isomers, stereoisomers, and anomers thereof. Non-limiting examples of monosaccharides include (in either the L- or D-conformation) glyceraldehyde, threose, ribose, altrose, glucose, mannose, talose, galactose, gulose, idose, lyxose, arabanose, xylose, allose, erythrose, erythrulose, tagalose, sorbose, ribulose, psicose, xylulose, fructose, dihydroxyacetone, and cyclic (alpha or beta) forms thereof. Multimers (disaccharides, trisaccharides, oligosaccharides, polysaccharides) thereof include, but are not limited to, sucrose, lactose, maltose, lactulose, trehalose, cellobiose, kojibiose, nigerose, isomaltose, sophorose, laminaribiose, gentioboise, turanose, maltulose, palatinose, gentiobiulose, mannobiose, melibiulose, rutinose, rutinulose, xylobiose, primeverose, amylose, amylopectin, starch (including resistant starch), chitin, cellulose, agar, agarose, xylan, glycogen, bacterial polysaccharides such as capsular polysaccharides, LPS, and peptidoglycan, and biofilm exopolysaccharide (e.g., alginate, EPS), N-linked glycans, and O-linked glycans. Prebiotic sugars can be modified and carbohydrate derivatives include amino sugars (e.g., sialic acid, N-acetylglucosamine, galactosamine), deoxy sugars (e.g., rhamnose, fucose, deoxyribose), sugar phosphates, glycosylamines, sugar alcohols, and acidic sugars (e.g., glucuronic acid, ascorbic acid).

In one embodiment, the prebiotic carbohydrate component of the pharmaceutical composition consists essentially of one or more non-digestible saccharides.

In one embodiment, the prebiotic carbohydrate component of the pharmaceutical composition allows the commensal colonic microbiota, comprising microorganisms associated with a healthy-state microbiome or presenting a low risk of a patient developing an autoimmune or inflammatory condition, to be regularly maintained. In one embodiment, the prebiotic carbohydrate allows the co-administered or co-formulated microbe or microbes to engraft, grow, and/or be regularly maintained in a mammalian subject. In some embodiments, the mammalian subject is a human subject, for example, a human subject having or suspected of having a food allergy.

In some embodiments, the prebiotic favors the growth of an administered microbe, wherein the growth of the administered microbe and/or the fermentation of the administered prebiotic by the administered microbe slows or reduces the growth of a pathogen or pathobiont. For example, FOS, neosugar, or inulin promotes the growth of acid-forming bacteria in the colon such as bacteria belonging to the genus *Lactobacillus* or *Bifidobacterium* and *Lactobacillus acidophilus* and *Bifidobacterium bifidus* can play a role in reducing the number of pathogenic bacteria in the colon (see e.g., U.S. Pat. No. 8,486,668). Other polymers, such as various galactans, lactulose, and carbohydrate based gums, such as *psyllium*, guar, carrageen, gellan, and konjac, are also known to improve gastrointestinal (GI) health.

In some embodiments, the prebiotic comprises one or more of GOS, lactulose, raffinose, stachyose, lactosucrose, FOS (i.e., oligofructose or oligofructan), inulin, isomalto-oligosaccharide, xylo-oligosaccharide, paratinose oligosaccharide, transgalactosylated oligosaccharides (i.e., transgalacto-oligosaccharides), transgalactosylate disaccharides, soybean oligosaccharides (i.e., soyoligosaccharides), gentiooligosaccharides, glucooligosaccharides, pecticoligosaccharides, palatinose polycondensates, difructose anhydride III, sorbitol, maltitol, lactitol, polyols, polydextrose, reduced paratinose, cellulose, β-glucose, β-galactose, β-fructose, verbascose, galactinol, and β-glucan, guar gum, pectin, high, sodium alginate, and lambda carrageenan, or mixtures thereof. The GOS may be a short-chain GOS, a long-chain GOS, or any combination thereof. The FOS can be a short-chain FOS, a long-chain FOS, or any combination thereof.

In some embodiments, the prebiotic composition comprises two carbohydrate species (non-limiting examples being a GOS and FOS) in a mixture of at least 1:1, at least 2:1, at least 5:1, at least 9:1, at least 10:1, about 20:1, or at least 20:1.

In some embodiments, the prebiotic comprises a mixture of one or more non-digestible oligosaccharides, non-digestible polysaccharides, free monosaccharides, non-digestible saccharides, starch, or non-starch polysaccharides.

Oligosaccharides are generally considered to have a reducing end and a non-reducing end, whether or not the saccharide at the reducing end is in fact a reducing sugar. Most oligosaccharides described herein are described with the name or abbreviation for the non-reducing saccharide (e.g., Gal or D-Gal), preceded or followed by the configuration of the glycosidic bond (a or (3), the ring bond, the ring position of the reducing saccharide involved in the bond, and then the name or abbreviation of the reducing saccharide (e.g., Glc or D-Glc). The linkage (e.g., glycosidic linkage, galactosidic linkage, glucosidic linkage) between two sugar units can be expressed, for example, as 1,4, 1→4, or (1-4).

Both FOS and GOS are non-digestible saccharides. β glycosidic linkages of saccharides, such as those found in, but not limited to, FOS and GOS, make these prebiotics mainly non-digestible and unabsorbable in the stomach and small intestine α-linked GOS (α-GOS) is also not hydrolyzed by human salivary amylase, but can be used by *Bifidobacterium bifidum* and *Clostridium butyricum* (Yamashita A. et al., 2004. J. Appl. Glycosci. 51:115-122). FOS and GOS can pass through the small intestine and into the large intestine (colon) mostly intact, except where commensal microbes and microbes administered as part of a pharmaceutical composition are able to metabolize the oligosaccharides.

GOS (also known as galacto-oligosaccharides, galactooligosaccharides, trans-oligosaccharide (TOS), trans-galactooligosaccharide (TGOS), and trans-galactooligosaccharide) are oligomers or polymers of galactose molecules ending mainly with a glucose or sometimes ending with a galactose molecule and have varying degree of polymerization (generally the DP is between 2-20) and type of linkages. In one embodiment, GOS comprises galactose and glucose molecules. In another embodiment, GOS comprises only galactose molecules. In a further embodiment, GOS are galactose-containing oligosaccharides of the form of [β-D-Gal-(1-6)]$_n$-β-D-Gal-(1-4)-D-Glc wherein n is 2-20. In another embodiment, GOS are galactose-containing oligosaccharides of the form Glc α1-4-[β Gal 1-6)]$_n$ where n=2-20. In another embodiment, GOS are in the form of α-D-Glc (1-4)-[β-D-Gal-(1-6)-]$_n$ where n=2-20. Gal is a galactopyranose unit and Glc (or Glu) is a glucopyranose unit.

In one embodiment, a prebiotic composition comprises a GOS-related compound. A GOS-related compound can have the following properties: a) a "lactose" moiety; e.g., GOS with a gal-glu moiety and any polymerization value or type of linkage; or b) be stimulatory to "lactose fermenting" microbes in the human GI tract; for example, raffinose (gal-fru-glu) is a "related" GOS compound that is stimulatory to both lactobacilli and bifidobacteria.

Linkages between the individual sugar units found in GOS and other oligosaccharides include β-(1-6), β-(1-4), β-(1-3) and β-(1-2) linkages. In one embodiment, the administered oligosaccharides (e.g., GOS) are branched saccharides. In another embodiment, the administered oligosaccharides (e.g., GOS) are linear saccharides.

Alpha-GOS (also called alpha-bond GOS or alpha-linked GOS) are oligosaccharides having an alpha-galactopyranosyl group. Alpha-GOS comprises at least one alpha glycosidic linkage between the saccharide units. Alpha-GOS are generally represented by α-(Gal)$_n$ (n usually represents an integer of 2 to 10) or α-(Gal)$_n$ Glc (n usually represents an integer of 1 to 9). Examples include a mixture of α-galactosylglucose, α-galactobiose, α-galactotriose, α-galactotetraose, and higher oligosaccharides. Additional non-limiting examples include melibiose, manninootriose, raffinose, stachyose, and the like, which can be produced from beat, soybean oligosaccharide, and the like.

Commercially available and enzyme synthesized alpha-GOS products are also useful for the compositions described herein. Synthesis of alpha-GOS with an enzyme is conducted utilizing the dehydration condensation reaction of α-galactosidase with the use of galactose, galactose-containing substance, or glucose as a substrate. The galactose-containing substance includes hydrolysates of galactose-containing substances, for example, a mixture of galactose and glucose obtained by allowing beta-galactosidase to act on lactose, and the like. Glucose can be mixed separately with galactose and be used as a substrate with α-galactosidase (see e.g., WO 02/18614). Methods of preparing alpha-GOS have been described (see e.g., EP 514551 and EP2027863).

In one embodiment, a GOS composition comprises a mixture of saccharides that are alpha-GOS and saccharides that are produced by transgalactosylation using β-galactosidase. In another embodiment, GOS comprises alpha-GOS. In another embodiment, alpha-GOS comprises α-(Gal)$_2$ from 10% to 100% by weight. In one embodiment, GOS comprises only saccharides that are produced by transgalactosylation using β-galactosidase.

In one embodiment, the pharmaceutical composition comprises, in addition to one or more microbes, an oligosaccharide composition that is a mixture of oligosaccharides comprising 1-20% by weight of di-saccharides, 1-20% by weight tri-saccharides, 1-20% by weight tetra-saccharides, and 1-20% by weight penta-saccharides. In another embodiment, an oligosaccharide composition is a mixture of oligosaccharides consisting essentially of 1-20% by weight of di-saccharides, 1-20% by weight tri-saccharides, 1-20% by weight tetra-saccharides, and 1-20% by weight penta-saccharides.

In one embodiment, a prebiotic composition is a mixture of oligosaccharides comprising 1-20% by weight of saccharides with a degree of polymerization (DP) of 1-3, 1-20% by weight of saccharides with DP of 4-6, 1-20% by weight of saccharides with DP of 7-9, and 1-20% by weight of saccharides with DP of 10-12, 1-20% by weight of saccharides with DP of 13-15.

In another embodiment, a prebiotic composition comprises a mixture of oligosaccharides comprising 50-55% by weight of di-saccharides, 20-30% by weight tri-saccharides, 10-20% by weight tetra-saccharide, and 1-10% by weight penta-saccharides. In one embodiment, a GOS composition is a mixture of oligosaccharides comprising 52% by weight of di-saccharides, 26% by weight tri-saccharides, 14% by weight tetra-saccharide, and 5% by weight penta-saccharides. In another embodiment, a prebiotic composition comprises a mixture of oligosaccharides comprising 45-55% by weight tri-saccharides, 15-25% by weight tetra-saccharides, 1-10% by weight penta-saccharides.

In certain embodiments, the composition comprises a mixture of neutral and acid oligosaccharides as disclosed in e.g., WO 2005/039597 (N.V. Nutricia) and US Patent Application 20150004130. In one embodiment, the acid oligosaccharide has a degree of polymerization (DP) between 1 and 5000. In another embodiment, the DP is between 1 and 1000. In another embodiment, the DP is between 2 and 250. If a mixture of acid oligosaccharides with different degrees of polymerization is used, the average DP of the acid oligosaccharide mixture is preferably between 2 and 1000. The acid oligosaccharide can be a homogeneous or heterogeneous carbohydrate. The acid oligosaccharides can be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides can be prepared by the methods described in e.g., WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). In some embodiments, the acid oligosaccharides have a degree of methoxylation above about 10%, above about 20%, above about 50%, above about 70%. In some embodiments, the acid oligosaccharides have a degree of methylation above about 10%, above about 20%, above about 50%, above about 70%.

The term neutral oligosaccharides as used in the present invention refers to saccharides which have a degree of polymerization of monose units exceeding 2, exceeding 3, exceeding 4, or exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term "neutral oligosaccharides", as used herein, refers to saccharides which have a degree of polymerization of the oligosaccharide below 60 monose units. The term "monose units" refers to units having a closed ring structure e.g., the pyranose or furanose forms. In some embodiments, the neutral oligosaccharide comprises at least 90% or at least 95% monose units selected from the group consisting of mannose, arabinose, fructose, fucose, rhamnose, galactose, -D-galactopyranose, ribose, glucose, xylose and derivatives thereof, calculated on the total number of monose units contained therein. Suitable neutral oligosaccharides are preferably fermented by the gut flora. Non-limiting examples of suitable neutral oligosaccharides are cellobiose (4-O-β-D-glucopyranosyl-D-glucose), cellodextrins ((4-O-β-D-glucopyranosyl)n-D-glucose), β-cyclo-dextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructo furanoside), D-agatose, D-lyxo-hexylose, lactosucrose (O-α-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]n-(1-4) α-D glucose), lactulose (4-O-β-D-galactopyranosyl-D-fructose), 4'-galatosyllactose (β-D-galactopyranosyl-(1-4)-O-β-D-glucopyranosyl-(1-4)-D-glucopyranose), synthetic galactooligosaccharide (neogalactobiose, isogalactobiose, galsucrose, isolactose I, II and III), fructans-Levan-type (β-D-(2→6)-fructofuranosyl)n α-D-glucopyranoside), fructans-Inulin-type (β-D-((2→1)-fructofuranosyl)n α-D-glucopyranoside), 1 f-β-fructofuranosylnystose (β-D-((2→1)-fructofuranosyl)n B-D-fructofuranoside), xylooligo-saccharides (B-D-((1→4)-xylose)n, lafinose, lactosucrose and arabinooligosaccharides.

In some embodiments, the neutral oligosaccharide is selected from the group consisting of fructans, fructooligosaccharides, indigestible dextrins galactooligo-saccharides (including transgalactooligosaccharides), xylooligosaccharides, arabinooligo-saccharides, glucooligosaccharides, mannooligosaccharides, fucooligosaccharides and mixtures thereof.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which can be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolyzed by human digestive enzymes. Numerous other commercial sources of indigestible oligosaccharides are readily available and known to skilled persons in the art. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further embodiment, the prebiotic mixture of the pharmaceutical composition described herein comprises an acid oligosaccharide with a DP between 1 and 5000, prepared from pectin, alginate, and mixtures thereof; and a neutral oligosaccharide, selected from the group of fructans, fructooligosaccharides, indigestible dextrins, galactooligosaccharides including transgalacto-oligosaccharides, xylooligosaccharides, arabinooligosaccharides, glucooligosaccharides, manno-oligosaccharides, fucooligosaccharides, and mixtures thereof.

In certain embodiments, the prebiotic mixture comprises xylose. In other embodiments, the prebiotic mixture comprises a xylose polymer (i.e. xylan). In some embodiments, the prebiotic comprises xylose derivatives, such as xylitol, a sugar alcohol generated by reduction of xylose by catalytic hydrogenation of xylose, and also xylose oligomers (e.g., xylooligosaccharide). While xylose can be digested by humans, via xylosyltransferase activity, most xylose ingested by humans is excreted in urine. In contrast, some microorganisms are efficient at xylose metabolism or can be selected for enhanced xylose metabolism. Microbial xylose metabolism can occur by at least four pathways, including the isomerase pathway, the Weimburg pathway, the Dahms pathway, and, for eukaryotic microorganisms, the oxidoreductase pathway.

The xylose isomerase pathway involves the direct conversion of D-xylose into D-xylulose by xylose isomerase, after which D-xylulose is phosphorylated by xylulose kinase to yield D-xylolose-5-phosphate, an intermediate of the pentose phosphate pathway.

In the Weimberg pathway, D-xylose is oxidized to D-xylono-lactone by a D-xylose dehydrogenase. Then D-xylose dehydrogenase is hydrolyzed by a lactonase to yield D-xylonic acid, and xylonate dehydratase activity then yields 2-keto-3-deoxy-xylonate. The final steps of the Weimberg pathway are a dehydratase reaction to form 2-keto glutarate semialdehyde and an oxidizing reaction to form 2-ketoglutarate, an intermediate of the Krebs cycle.

The Dahms pathway follows the same mechanism as the Weimberg pathway but diverges once it has yielded 2-keto-3-deoxy-xylonate. In the Dahms pathway, an aldolase splits 2-keto-3-deoxy-xylonate into pyruvate and glycolaldehyde.

The xylose oxido-reductase pathway, also known as the xylose reductase-xylitol dehydrogenase pathway, begins by the reduction of D-xylose to xylitol by xylose reductase followed by the oxidation of xylitol to D-xylulose by xylitol dehydrogenase. As in the isomerase pathway, the next step in the oxido-reductase pathway is the phosphorylation of D-xylulose by xylulose kinase to yield D-xylolose-5-phosphate.

Xylose is present in foods like fruits and vegetables and other plants such as trees for wood and pulp production. Thus, xylose can be obtained in the extracts of such plants. Xylose can be obtained from various plant sources using known processes including acid hydrolysis followed by various types of chromatography. Examples of such methods to produce xylose include those described in Maurelli, L. et al. (2013), Appl. Biochem. Biotechnol. 170:1104-1118; Hooi H. T et al. (2013), Appl. Biochem. Biotechnol. 170: 1602-1613; Zhang H-J. et al. (2014), Bioprocess Biosyst. Eng. 37:2425-2436.

Culture and Storage of Consortium Constituents

For banking, the strains included in the bacterial composition can be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments using a culturing step, the agar or broth contains nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, and 1 mg/L menadione. A variety of microbiological media and variations are well known in the art (e.g. R. M. Atlas, Handbook of Microbiological Media (2010) CRC Press). Medium can be added to the culture at the start, can be added during the culture, or can be intermittently/continuously flowed through the culture. The strains in the bacterial composition can be cultivated alone, as a subset of the bacterial composition, or as an entire collection comprising the bacterial composition. As an example, a first strain can be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For bacterial compositions for human use this is often at normal body temperature (37° C.), pH, and other parameter with values similar to the normal human niche. The environment can be actively controlled, passively controlled (e.g., via buffers), or allowed to drift. For example, for anaerobic bacterial compositions (e.g., gut microbiota), an anoxic/reducing environment can be employed. This can be accomplished by addition of reducing agents/factors such as cysteine to the broth, and/or stripping it of oxygen. As an example, a culture of a bacterial composition can be grown at 37° C., pH 7, in the medium above, pre-reduced with 1 g/L cysteine.HCl.

When the culture has generated sufficient biomass, it can be preserved for banking or storage. The organisms can be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition can be purified by additional means such as density gradient centrifugation preserved using the techniques described above. Bacterial composition banking can be done by culturing and preserving the strains individually, or by mixing the strains together to create a combined bank. As an example of cryopreservation, a bacterial composition culture can be harvested by centrifugation to pellet the cells from the culture medium, the supernate decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production can be conducted using similar culture steps to banking, including medium composition and culture conditions. It can be conducted at larger scales of operation, especially for clinical development or commercial production. At larger scales, there can be several sub-cultivations of the bacterial composition prior to the final cultivation. At the end of cultivation, the culture is harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition can be cultivated to a concentration of $10^{10}$ CFU/mL, then concentrated 20-fold by tangential flow microfiltration; the spent medium may be exchanged by diafiltering with a preservative medium consisting of 2% gelatin, 100 mM trehalose, and 10 mM sodium phosphate buffer. The suspension can then be freeze-dried to a powder and titrated.

After drying, the powder can be blended to an appropriate potency, and mixed with other cultures and/or a filler such as microcrystalline cellulose for consistency and ease of handling, and the bacterial composition formulated as provided herein.

In one embodiment, a composition comprising a microbial consortium as described herein, is not a fecal transplant. In some embodiments all or essentially all of the bacterial entities present in a purified population are originally obtained from a fecal material and subsequently, e.g., for production of pharmaceutical compositions, are grown in culture as described herein or otherwise known in the art. In one embodiment, the bacterial cells are cultured from a bacterial stock and purified as described herein. In one embodiment, each of the populations of bacterial cells are independently cultured and purified, e.g., each population is cultured separately and subsequently mixed together. In one embodiment, one or more of the populations of bacterial cells in the composition are co-cultured.

Dosage, Administration and Formulations

In some embodiments, cells over a range of, for example, $2$-$5 \times 10^5$, or more, e.g., $1 \times 10^6$, $1 \times 10^7$, $1 \times 10^8$, $5 \times 10^8$, $1 \times 10^9$, $5 \times 10^9$, $1 \times 10^{10}$, $5 \times 10^{10}$ or more can be administered in a composition comprising a microbial consortium. The dosage range for the bacteria depends upon the potency, and include amounts large enough to produce the desired effect, e.g., reduction in at least one symptom of a food allergy in a treated subject. The dosage should not be so large as to cause unacceptable adverse side effects. Generally, the dosage will vary with the type of illness, and with the age, condition, and sex of the patient. The dosage can be determined by one of skill in the art and can also be adjusted by the individual physician in the event of any complication.

For use in the various aspects described herein, an effective amount of cells in a composition as described herein comprises at least $10^2$ bacterial cells, at least $1 \times 10^3$ bacterial cells, at least $1 \times 10^4$ bacterial cells, at least $1 \times 10^5$ bacterial cells, at least $1 \times 10^6$ bacterial cells, at least $1 \times 10^7$ bacterial cells, at least $1 \times 10^8$ bacterial cells, at least $1 \times 10^9$ bacterial cells, at least $1 \times 10^{10}$ bacterial cells, at least $1 \times 10^{11}$ bacterial cells, at least $1 \times 10^{12}$ bacterial cells or more. Where a microbial consortium is isolated and/or purified from a subject that is tolerant to a selected food allergen, the bacterial cells can be derived from one or more donors, or can be obtained from an autologous source. In some embodiments of the aspects described herein, the cells of the microbial consortium are expanded or maintained in culture prior to administration to a subject in need thereof. In one embodiment, the microbial consortium is obtained from a microbe bank. Members of a therapeutic or preventive/prophylactic consortium are generally administered together, e.g., in a single admixture. However, it is specifically contemplated herein that members of a given consortium can be administered as separate dosage forms or sub-mixtures or sub-combinations of the consortium members. Thus, for a consortium of e.g., six members, the consortium can be administered, for example, as a single preparation including all six members (in one or more dosage units, e.g., one or more capsules) or as two or more separate preparations that, in sum, include all members of the given consortium. While administration as a single admixture is preferred, a potential advantage of the use of e.g., individual units for each member of a consortium, is that the actual strains administered to any given subject can be tailored, if necessary, by selecting the appropriate combination of, for example, single species dosage units that together comprise the desired consortium.

Biomass of Administered Species, Per Dose, Vs. Known In Vivo Biomass:

It is contemplated herein that the consortium composition is formulated to deliver a larger biomass than the normal biomass of the commensal organisms in a "healthy" individual. For example, the range of biomasses contemplated for delivery and colonization can be found in Table 1, column 2, as compared to the normal biomass in a healthy individual as shown in Table 1, columns 3 & 4. The table below shows the range of administered biomasses of organisms relative to published data at specific locations. Note, in many cases the bacterial quantitation in Gustafsson, 1982 was to general categories of organisms, such as *Clostridia*, and incorporated multiple species under those headers. Individual species in the consortia would thus likely be less than the actual highest reported biomass at the specific locations; the small and large intestinal biomass data should thus be considered an upper-bound for what might occur in vivo in normal individuals.

| Species | Consortia Biomass | Small Intestinal Biomass | Large Intestinal Biomass | Reference |
|---|---|---|---|---|
| *Bacteroides fragilis* | $1 \times 10^7$-$5 \times 10^8$ CFU/mL | $<10^3$ CFU/g duodenum-jejunum $10^3$-$10^8$ CFU/g in ileum | $10^8$-$10^{11}$ CFU/g | Gustafsson, 1982. [1] |
| *B. thetaiotaomicron* | $1 \times 10^7$-$5 \times 10^8$ CFU/mL | $<10^3$ CFU/g in duodenum-jejunum $10^3$-$10^8$ CFU/g in ileum | $10^8$-$10^{11}$ CFU/g | Gustafsson, 1982. Bry, 1996. [2] |
| *B. ovatus* | $1 \times 10^7$-$5 \times 10^8$ CFU/mL | $<10^3$ CFU/g in duodenum-jejunum $10^3$-$10^8$ CFU/g in ileum | $10^8$-$10^{11}$ CFU/g | Gustafsson, 1982. |
| *C. bifermentans* | $1 \times 10^7$-$5 \times 10^8$ CFU/mL | $<10^3$ CFU/g in duodenum-jejunum $10^2$-$10^4$ CFU/g in ileum | $0$-$10^6$ CFU/g | Gustafsson, 1982. |
| *C. hiranonsis* | $1 \times 10^7$-$5 \times 10^8$ CFU/mL | $<10^3$ CFU/g in duodenum-jejunum $10^2$-$10^4$ CFU/g in ileum | $0$-$10^6$ CFU/g | Gustafsson, 1982. |
| *C. leptum* | $1 \times 10^7$-$5 \times 10^8$ CFU/mL | $<10^3$ CFU/g in duodenum-jejunum $10^2$-$10^4$ CFU/g in ileum | $0$-$10^6$ CFU/g | Gustafsson, 1982. |
| *Clostridium ramosum* | $1 \times 10^7$-$5 \times 10^8$ CFU/mL | $<10^3$ CFU/g in duodenum-jejunum $10^2$-$10^4$ CFU/g in ileum | $0$-$10^6$ CFU/g | Gustafsson, 1982. |
| *C. sardiniensis* | $1 \times 10^7$-$5 \times 10^8$ CFU/mL | $<10^3$ CFU/g in duodenum-jejunum $10^2$-$10^4$ CFU/g in ileum | $0$-$10^6$ CFU/g | Gustafsson, 1982. |
| *C. scindens* | $1 \times 10^7$-$5 \times 10^8$ CFU/mL | $<10^3$ CFU/g in duodenum-jejunum $10^2$-$10^4$ CFU/g in ileum | $0$-$10^6$ CFU/g | Gustafsson, 1982. |
| *Parabacteroides goldsteinii* | $1 \times 10^7$-$5 \times 10^8$ CFU/mL | $<10^3$ CFU/g in duodenum-jejunum $10^3$-$10^8$ CFU/g in ileum | $0$-$10^6$ CFU/g | Gustafsson, 1982. |
| *Prevotella tannerae* | $1 \times 10^7$-$5 \times 10^8$ CFU/mL | $<10^3$ CFU/g in duodenum-jejunum $<10^4$ CFU/g in ileum | $0$-$10^6$ CFU/g | Gustafsson, 1982. |

References:
[1] Gustafsson, BE. The physiological importance of the colonic microflora. *Scand J. Gastroenterol Suppl.* 1982, 77: 117-31.
[2] Bry L, et al. A model of host-microbial interactions in an open mammalian ecosystem. *Science.* 1996, 273(5280): 1380-3.

A pharmaceutical composition comprising a microbial consortium can be administered by any method suitable for depositing in the gastrointestinal tract, preferably the colon, of a subject (e.g., human, mammal, animal, etc.). Examples of routes of administration include rectal administration by colonoscopy, suppository, enema, upper endoscopy, or upper push enteroscopy. Additionally, intubation through the nose or the mouth by nasogastric tube, nasoenteric tube, or nasal jejunal tube can be utilized. Oral administration by a solid such as a pill, tablet, a suspension, a gel, a geltab, a semisolid, a tablet, a sachet, a lozenge or a capsule or microcapsule, or as an enteral formulation, or re-formulated for final delivery as a liquid, a suspension, a gel, a geltab, a semisolid, a tablet, a sachet, a lozenge or a capsule, or as an enteral formulation can be utilized as well. Also contemplated herein are food items that are inoculated with a microbial consortium as described herein. Compositions can also be treated or untreated fecal flora, entire (or substantially entire) microbiota, or partially, substantially or completely isolated or purified fecal flora, and can be lyophilized, freeze-dried or frozen, or processed into a powder.

In some embodiments, the compositions described herein can be administered in a form containing one or more pharmaceutically acceptable carriers. Suitable carriers are well known in the art and vary with the desired form and mode of administration of the composition. For example, pharmaceutically acceptable carriers can include diluents or excipients such as fillers, binders, wetting agents, disintegrators, surface-active agents, glidants, lubricants, and the like. Typically, the carrier may be a solid (including powder), liquid, or combinations thereof. Each carrier is preferably "acceptable" in the sense of being compatible with the other ingredients in the composition and not injurious to the subject. The carrier may be biologically acceptable and inert (e.g., it permits the composition to maintain viability of the biological material until delivered to the appropriate site).

Oral compositions can include an inert diluent or an edible carrier. For the purpose of oral therapeutic administration, the active compound can be incorporated with excipients and used in the form of tablets, lozenges, pastilles, troches, or capsules, e.g., gelatin capsules. Oral compositions can also be prepared by combining a composition of the present disclosure with a food. In one embodiment a food used for administration is chilled, for instance, iced flavored water. In certain embodiments, the food item is not a potentially allergenic food item (e.g., not soy, wheat, peanut, tree nuts, dairy, eggs, shellfish or fish). Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, orange flavoring, or other suitable flavorings. These are for purposes of example only and are not intended to be limiting.

The compositions comprising a microbial consortium can also be prepared in the form of suppositories (e.g., with conventional suppository bases such as cocoa butter and other glycerides) or retention enemas for rectal delivery. The compositions can be prepared with carriers that will protect the consortium against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

In some embodiments, a composition can be encapsulated (e.g., enteric-coated formulations). For instance, when the composition is to be administered orally, the dosage form is formulated so the composition is not exposed to conditions prevalent in the gastrointestinal tract before the small intestine, e.g., high acidity and digestive enzymes present in the stomach. The encapsulation of compositions for therapeutic use is routine in the art. Encapsulation can include hard-shelled capsules, which can be used for dry, powdered ingredients soft-shelled capsules. Capsules can be made from aqueous solutions of gelling agents such as animal protein (e.g., gelatin), plant polysaccharides or derivatives like carrageenans and modified forms of starch and cellulose. Other ingredients can be added to a gelling agent solution such as plasticizers (e.g., glycerin and or sorbitol), coloring agents, preservatives, disintegrants, lubricants and surface treatment.

In one embodiment, a microbial consortium as described herein is formulated with an enteric coating. An enteric coating can control the location of where a microbial consortium is released in the digestive system. Thus, an enteric coating can be used such that a microbial consortium-containing composition does not dissolve and release the microbes in the stomach, which can be a toxic environment for many microbes, but rather travels to the small intestine, where it dissolves and releases the microbes in an environment where they can survive. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade names AQUACOAT, AQUACOAT ECD, SEPIFILM™, KLUCEL™, and METOLOSE™); polyvinylacetate phthalate (trade name SURETERIC™); and methacrylic acid (trade name EUDRAGIT™). In one embodiment, an enteric coated probiotic composition comprising members of a microbial consortium as described herein is administered to a subject. In another embodiment, an enteric coated probiotic and prebiotic composition is administered to a subject.

Formulations suitable for rectal administration include gels, creams, lotions, aqueous or oily suspensions, dispersible powders or granules, emulsions, dissolvable solid materials, douches, and the like. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment agent of the present disclosure can be formulated for colonic or rectal administration.

Formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

In some embodiments, the microbial consortium can be formulated in a food item. Some non-limiting examples of food items to be used with the methods and compositions described herein include: popsicles, cheeses, creams, chocolates, milk, meat, drinks, yogurt, pickled vegetables, kefir, miso, sauerkraut, etc. In other embodiments, the food items can be juices, refreshing beverages, tea beverages, drink preparations, jelly beverages, and functional beverages; alcoholic beverages such as beers; carbohydrate-containing foods such as rice food products, noodles, breads, and pastas; paste products such as fish, hams, sausages, paste products of seafood; retort pouch products such as curries, food dressed with a thick starchy sauce, and Chinese soups; soups; dairy products such as milk, dairy beverages, ice creams, cheeses, and yogurts; fermented products such as fermented soybean pastes, fermented beverages, and pickles; bean products; various confectionery products including biscuits, cookies, and the like, candies, chewing gums, gummies, cold desserts including jellies, cream caramels, and frozen desserts; instant foods such as instant soups and instant soy-bean soups; and the like. It is preferred that food preparations not require cooking after admixture with the microbial consortium to avoid killing the microbes.

Formulations of a microbial consortium can be prepared by any suitable method, typically by uniformly and intimately admixing the consortium with liquids or finely divided solid carriers or both, in the required proportions and then, if necessary, shaping the resulting in mixture into the desired shape. In addition, the microbial consortium can be treated to prolong shelf-life, preferably the shelf-life of the pre-determined gut flora will be extended via freeze drying.

In some embodiments, the microbial consortium as described herein is combined with one or more additional probiotic organisms prior to treatment of a subject. As used herein, the term "probiotic" refers to microorganisms that form at least a part of the transient or endogenous flora or microbial consortium and thereby exhibit a beneficial prophylactic and/or therapeutic effect on the host organism. Probiotics are generally known to be clinically safe (i.e., non-pathogenic) by those individuals skilled in the art. Typical lactic acid-producing bacteria useful as a probiotic of this invention are efficient lactic acid producers which include non-pathogenic members of the *Bacillus* genus which produce bacteriocins or other compounds which inhibit the growth of pathogenic organisms.

Exemplary lactic acid-producing, non-pathogenic *Bacillus* species include, but are not limited to: *Bacillus coagulans*; *Bacillus coagulans* Hammer; and *Bacillus brevis* subspecies *coagulans*.

Exemplary lactic acid-producing *Lactobacillus* species include, but are not limited to: *Lactobacillus acidophilus, Lactobacillus casei, Lactobacillus* DDS-1, *Lactobacillus* GG, *Lactobacillus rhamnosus, Lactobacillus plantarum, Lactobacillus reuteri, Lactobacillus gasserii, Lactobacillus jensenii, Lactobacillus delbruekii, Lactobacillus bulgaricus, Lactobacillus salivarius* and *Lactobacillus sporogenes* (also designated as *Bacillus coagulans*). Exemplary lactic acid-producing *Sporolactobacillus* species include all *Sporolactobacillus* species, for example, *Sporolactobacillus* P44.

Exemplary lactic acid-producing *Bifidobacterium* species include, but are not limited to: *Bifidobacterium adolescentis, Bifidobacterium animalis, Bifidobacterium bifidum, Bifidobacterium bifidus, Bifidobacterium breve, Bifidobacterium infantis, Bifidobacterium infantus, Bifidiobacterium longum*, and any genetic variants thereof.

Examples of suitable non-lactic acid-producing *Bacillus* include, but are not limited to: *Bacillus subtilis, Bacillus uniflagellatus, Bacillus lateropsorus, Bacillus laterosporus* BOD, *Bacillus megaterium, Bacillus polymyxa, Bacillus licheniformis, Bacillus pumilus,* and *Bacillus sterothermophilus*. Other strains that could be employed due to probiotic activity include members of the *Streptococcus (Enterococcus)* genus. For example, *Enterococcus faecium*, is commonly used as a livestock probiotic and, thus, could be utilized as a co-administration agent. Furthermore, it is also intended that any of the acid-producing species of probiotic or nutritional bacteria known in the art can be used in the compositions comprising a microbial consortium as described herein.

A nutrient supplement comprising the microbial consortium as described herein can include any of a variety of nutritional agents, including vitamins, minerals, essential and nonessential amino acids, carbohydrates, lipids, foodstuffs, dietary supplements, short chain fatty acids and the like. Preferred compositions comprise vitamins and/or minerals in any combination. Vitamins for use in a composition as described herein can include vitamins B, C, D, E, folic acid, K, niacin, and like vitamins. The composition can contain any or a variety of vitamins as may be deemed useful for a particularly application, and therefore, the vitamin content is not to be construed as limiting. Typical vitamins are those, for example, recommended for daily consumption and in the recommended daily amount (RDA), although precise amounts can vary. The composition can preferably include a complex of the RDA vitamins, minerals and trace minerals as well as those nutrients that have no established RDA, but have a beneficial role in healthy human or mammal physiology. The preferred mineral format would include those that are in either the gluconate or citrate form because these forms are more readily metabolized by lactic acid bacteria. In a related embodiment, the compositions described herein are contemplated to comprise a microbial consortium in combination with a viable lactic acid bacteria in combination with any material to be adsorbed, including but not limited to nutrient supplements, foodstuffs, vitamins, minerals, medicines, therapeutic compositions, antibiotics, hormones, steroids, and the like compounds where it is desirable to insure efficient and healthy absorption of materials from the gastrointestinal tract into the blood. The amount of material included in the composition can vary widely depending upon the material and the intended purpose for its absorption, such that the composition is not to be considered as limiting.

In some embodiments, the compositions described herein can further include a prebiotic and/or a fiber. Many forms of "fiber" exhibit some level of prebiotic effect. Thus, there is considerable overlap between substances that can be classified as "prebiotics" and those that can be classified as "fibers". Non-limiting examples of prebiotics suitable for use in the compositions and methods include *psyllium*, fructo-oligosaccharides, inulin, oligofructose, galacto-oligosaccharides, isomalto-oligosaccharides xylo-oligosaccharides, soy-oligosaccharides, gluco-oligosaccharides, mannan-oligosaccharides, arabinogalactan, arabinxylan, lactosucrose, gluconannan, lactulose, polydextrose, oligodextran, gentioligosaccharide, pectic oligosaccharide, xanthan gum, gum arabic, hemicellulose, resistant starch and its derivatives, and mixtures and/or combinations thereof. The compositions can comprise from about 100 mg to about 100 g, alternatively from about 500 mg to about 50 g, and alternatively from about 1 g to about 40 g, of prebiotic, per day or on a less than daily schedule.

Aspects of the technology described herein also include short chain fatty acids (SCFAs) and medium chain triglycerides (MCTs). Short chain fatty acids can have immunomodulatory (i.e., immunosuppressive) effects and therefore their production (i.e., biosynthesis or conversion by fermentation) is advantageous for the prevention, control, mitigation, and treatment of autoimmune and/or inflammatory disorders (Lara-Villoslada F. et al., 2006. *Eur J Nutr.* 45(7): 418-425). In germ-free mice and vancomycin-treated conventional mice, administration of SCFA (acetate, propionate, or butyrate) restored normal numbers of Tregs in the large intestine (Smith P M, et al. Science. 2013; 569-573). Short-chain fatty acids (SCFA) are produced by some bacteria as a byproduct of xylose fermentation. SCFA are one of the most abundant metabolites produced by the gut microbiome, particularly the family Clostridiaceae, including members of the genus *Clostridium, Ruminococcus*, or *Blautia*. In some aspects, the pharmaceutical composition, dosage form, or kit comprises at least one type of microbe (e.g., one or more microbial species, such as a bacterial species, or more than one strain of a particular microbial species) and at least one type of prebiotic such that the composition, dosage form, or kit is capable of increasing the level of one or more immunomodulatory SCFA (e.g., acetate, propionate, butyrate, or valerate) in a mammalian subject. Optionally, the pharmaceutical composition, dosage form, or kit further comprises one or more substrates of one or more SCFA-producing fermentation and/or biosynthesis pathways. In certain embodiments, the administration of the composition, dosage form, or kit to a mammalian subject results in the increase of one or more SCFAs in the mammalian subject by approximately 1.5-fold, 2-fold, 5-fold, 10-fold, 20-fold, 50-fold, 100-fold, or greater than 100-fold. In some embodiments, the dysbiosis is caused by a deficiency in microbes that produce short chain fatty acids. Accordingly, in some embodiments, the probiotic composition can contain a species of bacteria that produce short chain fatty acids.

MCTs passively diffuse from the GI tract to the portal system (longer fatty acids are absorbed into the lymphatic system) without requirement for modification like long-chain fatty acids or very-long-chain fatty acids. In addition, MCTs do not require bile salts for digestion. Patients who have malnutrition or malabsorption syndromes are treated with MCTs because they do not require energy for absorption, use, or storage. Medium-chain triglycerides are generally considered a good biologically inert source of energy that the human body finds reasonably easy to metabolize. They have potentially beneficial attributes in protein metabolism, but may be contraindicated in some situations due to their tendency to induce ketogenesis and metabolic acidosis. Due to their ability to be absorbed rapidly by the body, medium-chain triglycerides have found use in the treatment of a variety of malabsorption ailments. MCT supplementation with a low-fat diet has been described as the cornerstone of treatment for primary intestinal lymphangiectasia (Waldmann's disease). MCTs are an ingredient in parenteral nutritional emulsions.

Also contemplated herein are kits comprising, at a minimum, a microbial consortium prep or formulations comprising all of the members of the consortium in an admixture or comprising all of the members of the consortium in sub-combinations or sub-mixtures. In some embodiments, the kit further comprises empty capsules to be filled by the practitioner and/or one or more reagents for enteric coating such capsules. It is also contemplated herein that the microbe preparation is provided in a dried, lyophilized or powdered form. In one embodiment, the kits comprise at least 4 strains selected from the group consisting of: *Clostridium ramosum, Clostridium scindens, Clostridium hiranonsis, Clostridium bifermentans, Clostridium leptum, Clostridium sardiniensis, Bacteroides fragilis, Bacteroides thetaiotaomicron, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile*, and *Veilonella ratti*. In another embodiment, the kits comprise at least four strains selected from the group consisting of: *Clostridium ramosum, C. scindens, C. hiranonsis, C. bifermentans, C. leptum, C. sardiniensis, Bacteroides fragilis, B. thetaiotaomicron, B. ovatus, Parabacteroides goldsteinii*, and *Prevotella tannerae*. In another embodiment, the kits comprise at least four strains selected from the group consisting of: *Clostridium ramosum, C. scindens, C. hiranonsis, C. bifermentans, C. leptum*, and *C. sardiniensis*. In another embodiment, the kits comprise at least four strains selected from the group consisting of: *Bacteroides fragilis, B. thetaiotaomicron, B. ovatus, Parabacteroides goldsteinii*, and *Prevotella tannerae*. In one embodiment, the kits comprise *Bacteroides thetaiotaomicron* or *Bacteroides fragilis* and at least one of a strain selected from the group consisting of: *Clostridium ramosum, Clostridium scindens, Clostridium hiranonsis, Clostridium bifermentans, Clostridium leptum, Clostridium sardiniensis, Bacteroides ovatus, Parabacteroides goldsteinii, Prevotella tannerae, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum, Clostridium sporosphaeroides, Dialister proprionicfaceins, Dialister succinatiphilus, Parabacteroides distasonis, Parabacteroides goldsteinii, Parabacteroides merdae, Peptostreptococcus anaerobius, Subdoligranulum variabile*, and *Veilonella ratti*. In one embodiment, the kits comprise *Bacteroides thetaiotaomicron* or *Bacteroides fragilis* and at least one of a strain selected from the group consisting of: *Clostridium ramosum, Clostridium scindens, Clostridium hiranonsis, Clostridium bifermentans, Clostridium leptum, Clostridium sardiniensis, Clostridum hathewayi, Clostridum nexile, Clostridium hylemonae, Clostridium glycyrrhizinilyticum, Clostridium scindens, Clostridium lavalense, Clostridum fimetarium, Clostridium symbiosum*, and *Clostridium sporosphaeroides*. In another embodiment, the kit comprises at least one reducing agent such as N-acetylcysteine, cysteine, or methylene blue for growing, maintaining and/or encapsulating the microbes under anaerobic conditions. The kits described herein are also contemplated to include cell growth media and supplements necessary for expanding the microbial preparation. The kits described herein are also contemplated to include one or more prebiotics as described herein.

Prior to administration of the bacterial composition, the patient may optionally have a pretreatment protocol to prepare the gastrointestinal tract to receive the bacterial composition. In certain embodiments, the pretreatment protocol is advisable, such as when a patient has an acute infection with a highly resilient pathogen. In other embodiments, the pretreatment protocol is entirely optional, such as when the pathogen causing the infection is not resilient, or the patient has had an acute infection that has been successfully treated but where the physician is concerned that the infection may recur. In these instances, the pretreatment protocol can enhance the ability of the bacterial composition to affect the patient's microbiome. In an alternative embodiment, the subject is not pre-treated with an antibiotic.

As one way of preparing the patient for administration of the microbial ecosystem, at least one antibiotic can be administered to alter the bacteria in the patient. As another way of preparing the patient for administration of the microbial ecosystem, a standard colon-cleansing preparation can be administered to the patient to substantially empty the contents of the colon, such as used to prepare a patient for a colonoscopy. By "substantially emptying the contents of the colon," this application means removing at least 75%, at least 80%, at least 90%, at least 95%, or about 100% of the contents of the ordinary volume of colon contents. Antibiotic treatment can precede the colon-cleansing protocol.

If a patient has received an antibiotic for treatment of an infection, or if a patient has received an antibiotic as part of a specific pretreatment protocol, in one embodiment the antibiotic should be stopped in sufficient time to allow the antibiotic to be substantially reduced in concentration in the gut before the bacterial composition is administered. In one embodiment, the antibiotic may be discontinued 1, 2, or 3 days before the administration of the bacterial composition. In one embodiment, the antibiotic can be discontinued 3, 4, 5, 6, or 7 antibiotic half-lives before administration of the bacterial composition. If the pretreatment protocol is part of treatment of an acute infection, the antibiotic may be chosen so that the infection is sensitive to the antibiotic, but the constituents in the bacterial composition are not sensitive to the antibiotic.

Any of the preparations described herein can be administered once on a single occasion or on multiple occasions, such as once a day for several days or more than once a day on the day of administration (including twice daily, three times daily, or up to five times daily). Or the preparation can be administered intermittently according to a set schedule, e.g., once weekly, once monthly, or when the patient relapses from the primary illness. In another embodiment, the preparation can be administered on a long-term basis to assure the maintenance of a protective or therapeutic effect.

In one embodiment, a first microbial consortium comprising at least one bacterial species known to enhance colonization of beneficial organisms (e.g., *Bacteroides thetaiotaomicron*) is administered to a subject prior to administration of a second microbial consortium.

Another aspect described herein relates to a method for enhancing the colonization and/or persistence of a microbial consortium, the method comprising administering a first microbial consortium comprising at least 4 bacterial strains selected from the group consisting of: *Bacteroides fragilis, B. thetaiotaomicron, B. ovatus, Parabacteroides goldsteinii,* and *Prevotella tannerae*, to a subject prior to administering a second microbial consortium comprising at least 4 bacterial strains selected from the group consisting of: *Clostridium ramosum, C. scindens, C. hiranonsis, C. bifermentans, C. leptum* and *C. sardiniensis*, wherein the first microbial consortium enhances the colonization and/or persistence of the second microbial consortium.

It is also contemplated herein that a first microbial consortium comprising at least 4 bacterial strains selected from the group consisting of: *Clostridium ramosum, C. scindens, C. hiranonsis, C. bifermentans, C. leptum* and *C. sardiniensis*, is administered to a subject prior to administering a second microbial consortium comprising at least 4 bacterial strains selected from the group consisting of: *Bacteroides fragilis, B. thetaiotaomicron, B. ovatus, Parabacteroides goldsteinii,* and *Prevotella tannerae*.

It is also contemplated herein that a first microbial consortium comprising at least 4 bacterial strains selected from the group consisting of: *Clostridium ramosum, C. scindens, C. hiranonsis, C. bifermentans, C. leptum* and *C. sardiniensis*, is administered to a subject in combination with (e.g., simultaneously) a second microbial consortium comprising at least 4 bacterial strains selected from the group consisting of: *Bacteroides fragilis, B. thetaiotaomicron, B. ovatus, Parabacteroides goldsteinii,* and *Prevotella tannerae*.

Efficacy

Typically, a food allergy response can manifest with one of more of the following symptoms or indicators: (i) a marked drop in core body temperature, (ii) an increase in total IgE, (iii) an increase in allergen-specific IgE, (iv) mast cell expansion, (v) release of mast cell granule protease 1 (MMCP-1) and (vi) increase in Th2 cell skewing. Thus, efficacious treatment and/or prevention of food allergy using the methods and compositions described herein can reduce or eliminate at least one of the symptoms or indicators associated with food allergy, as described above. "Reduced" symptoms or indicators mean at least 20% reduced, at least 30% reduced, at least 40% reduced, at least 50% reduced, at least 60% reduced, at least 70% reduced, at least 80% reduced, at least 90% reduced, at least 95% reduced, at least 98% reduced or even at least 99% or further reduction. Methods for the measurement of each of these parameters are known to those of ordinary skill in the art.

The methods and compositions described herein provide treatment or prevention of food allergy involving or provoking anaphylaxis—i.e., IgE-mediated histamine release or direct allergen-mediated degranulation of mast cells and basophils and resulting pathology. Non-limiting examples include allergy or anaphylactic reaction to peanut, tree nuts, and shellfish, among others noted elsewhere herein. Food sensitivity, e.g., lactose intolerance or gluten intolerance involves different mechanisms. While it is contemplated that a microbial consortium as described herein can benefit those with food sensitivities (e.g., by reducing or eliminating a dysbiotic state and thereby reducing gut inflammation), the distinction between food sensitivities and food allergies should be specifically noted. First and foremost, sensitivities do not provoke an anaphylactic response.

Effective prevention of food allergy can be assessed using an accepted animal model, such as that described herein or others known to those of ordinary skill in the art, wherein a regimen that sensitizes the animals to a given food allergen in the absence of microbial consortium treatment fails to provoke a substantial allergic response in animals administered a protective microbial consortium as described herein. As used herein, the term "fails to provoke a substantial allergic response" means that there is less than 20% of the allergic response (as measured by one or more of the criteria (i)-(vi) described above) seen in animals sensitized to the allergen but without administration of a protective or therapeutic microbial consortium as described herein. In human clinical practice, prevention or cure can be evaluated by administration of the given microbial consortium followed by administration of an allergen under controlled circumstances in a doctor's office or hospital setting. For prevention, the microbial consortium can be administered prior to a patient's initial exposure to or consumption of a given food allergen. For therapy for established food allergy, the microbial consortium can be administered as described herein, followed by consumption of the food allergen in a controlled clinical setting. A lack of allergic reaction, or even a reduced allergic reaction relative to the patient's previous allergic responses to the allergen (i.e., at least 20% reduced, at least 30% reduced, at least 40% reduced, at least 50% reduced, at least 60% reduced, at least 70% reduced, at least 80% reduced, at least 90% reduced, at least 95% reduced, at least 98% reduced or even at least 99% or further reduction) is evidence of effective treatment.

Repeated administration of the microbial consortium may be beneficial to maintain a protective or curative effect.

In addition, efficacy of a particular formulation can be determined in vitro or in an in vivo or in situ mouse model as described in herein or as known in the art (e.g., Noval Rivas et al. *J Allergy Clin Immunol* (2013) 131(1):201-212 or Noval Rivas et al., *Immunity* (2015) 42:512-523, the contents of which are each incorporated herein in their entirety).

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

EXAMPLES

The data provided herein, e.g., in the figures and elsewhere, show that a microbial consortium of several species (i.e., 2, 3, 4, 5, or 6 species, for example) can protect against developing food allergy in a mouse model. Treatment with such a consortium of bacteria can reverse TH2 programming of Tregs. Treatment and/or prevention of food allergy using a similar microbial consortium of microbes in humans is specifically indicated.

Further methods for testing or measuring the efficacy of a microbial consortium in a mouse model of food allergy are known in the art and/or can be found in e.g., Noval Rivas et al. *J Allergy Clin Immunol* (2013) 131(1):201-212 or Noval Rivas et al., *Immunity* (2015) 42:512-523, the contents of which are each incorporated herein in their entirety.

Example 1: Therapeutic Microbiota to Treat Food Allergy

Summary

Food allergy is a growing national problem, affecting 6% of children, and 3% of US teens and adults. Unfortunately for these children and their families, the standard of care remains to avoid offending foods and manage symptoms as they occur. Therapies using oral desensitization, alone or with anti-IgE (Omalizumab™), remain experimental with limited success. Needed are therapies that target the aberrant immune responses. As such, this study shows the use of gut microbiota as a therapeutic intervention to promote tolerizing responses that can prevent or mitigate effects of Th2/allergic responses.

Food allergies occur with development of Th2-allergic responses to foodstuffs, in contrast to tolerizing T-regulatory responses that mitigate such responses mucosally. The Th2 responses promote food antigen-specific IgE antibody and recruitment of mucosal mast cells, in contrast to regulatory responses, which inhibit these effects. Once sensitized to one or more food antigens, re-exposure can induce life-threatening anaphylactic responses. Capacity to promote tolerizing responses supports a broad-based therapeutic approach that can act at the earliest stages of exposure as well as in the already-sensitized patient to prevent aberrant allergic responses across a spectrum of foodstuffs.

Leveraging the genetically susceptible IL4RA F709 mouse model [1,2] of food allergy defined human commensal communities that can both prevent and cure food allergies in preclinical models have been developed. These communities leverage a new therapeutic pathway for patients—immunomodulation from the luminal side of the gut, the space in which the gut microbiota resides. Human gut microbiota consists of many hundreds of species that provide critical functions in normal human development and health, from maturing of the immune system, providing essential nutrients such as B vitamins and vitamin K, and assisting in digestion and metabolism of dietary and exogenous compounds, including drugs and ingested foodstuffs.

Background

The therapeutic consortia consist of defined and culturable human commensal strains that stimulate protective regulatory T cell responses in the gut. Two protective communities have been developed, Gut-Protect I (GP-I) and Gut-Protect II (GP-II). All have complete or contig-level genomic sequences, and select members from each group can be genetically manipulated. In addition, a third community has been developed that demonstrates worsened effects (Negative Control Consortium, Neg-CC), which is providing further information on dysbiotic effects in vivo and potential biomarkers to assist in diagnosis and selection of therapy.

(1) Gut-protect I: Community of culturable gut commensals that has demonstrated treat-to-protect and treat-to-cure efficacy in food antigen sensitization of IL4RA F709 mice.

(2) Gut-protect II: Community of culturable gut commensals that has demonstrated robust treat-to-prevent efficacy in animal models and less robust treat-to-cure efficacy than Gut-protect I. However, in standard solutions administered to the host, this community tolerates greater ambient air exposure than the Gut-protect I community.

(3) Negative Control Community: Community of culturable gut commensals that promote food antigen sensitization in treat-to-prevent and treat-to-cure regimens. This community is defining the nature of dysbiosis in food allergy and supporting development of biomarkers that could predict microbiota-derived factors that enhance susceptibility to development of food allergies.

In pre-clinical models of food allergy to egg, leveraging a susceptible mouse model that does not require the use of adjuvants, GP-I and GP-II each demonstrated treat-to-prevent efficacy, when used in a period of sensitization to the allergy-inducing foodstuff. GP-I was also effective in treat-to-cure regimens when used in animals that had already been sensitized to egg protein, to the point that re-exposure would induce life-threatening anaphylactic responses. In contrast, the negative control community worsened effects, and provides further insights as to the underlying dysbiosis that may contribute to development of food allergies, while also providing potential biomarkers to identify individuals at risk, or for whom microbial therapy may be efficacious.

Consortia Development

For pre-clinical studies in mice the component members are grown individually in nutrient-rich media under appropriate anaerobic conditions, quantitated for biomass, and then the consortium is mixed under anaerobic conditions with approximately equal biomass of each component organism to a final concentration ~$5.0 \times 10^8$ colony forming units (CFU)/mL. Input culture volumes for each species have been in the range of 100 mL-1 L. As needed, cultures with a stationary phase biomass <$5 \times 10^8$ CFU/mL are concentrated by centrifugation with re-suspension handled under anaerobic conditions.

When mixed, the total biomass remains approximately $5 \times 10^8$ CFU/mL. 2 mL aliquots are placed in cryovials with an anaerobic/pre-reduced atmosphere, snap frozen on liquid nitrogen and stored at −80° C. until use. Rapid freezing has shown to have <½ log effects on the biomass of the component organisms and no effect on efficacy in animal models. For studies, tubes are thawed and mice administered 200 uL of this solution weekly to twice weekly by oral gavage, resulting in a total introduced biomass of $1 \times 10^8$ CFU/mouse. The measurements of gut contents in adult mice (stomach through anus) range from 4-8 mL of material. The gavaged consortium is thus 2.5-5% of the total volume of contents in the mouse gut and >10% of the volume of contents in the small bowel.

In terms of pre-existing microbial biomass from the conventional microbiota—the mouse small intestine on average has ~$10^4$ CFU/mL in proximal duodenum with increase to $10^8$ CFU/mL in the ileum. Biomass increases to $10^9$-$10^{10}$ CFU/mL in the cecum and colon. From the standpoint of microbial biomass at locations in the mouse small bowel, the primary site of action of the consortia to promote regulatory T cell responses, the consortium is 10,000× the biomass of the duodenal microbiota, and 1-2× the biomass of the jejunal and ileal microbiota.

In comparison, the adult human gut may contain 4.5 L of material, of which 1 L relates to ingested foodstuffs with 3.5 L of secretions including saliva, bile, and other fluids from the pancreas and intestines [3]. These fluids and electrolytes are largely resorbed in the right colon, subsequent to fecal compaction and passage. Within the intestines, the biomass of organisms also varies, with the highest concentration in the cecum and right side of the colon ($10^{10}$-$10^{12}$ CFU/mL). In contrast, in the small intestine—the believed site of action, the biomass also ranges from $10^4$ CFU/mL in the duodenum to $10^8$ CFU/mL in the ileum [4, 5].

Human Dosing

The CFU/dose for humans is based on the following parameters:

(1) Treatment of *C. difficile* with oral capsule formulations of human stool: Data from OpenBiome and other groups have shown successful treatment of *C. difficile* colitis with capsule formulation that administers $3-5\times10^9$ CFU in a range of 12-30 capsules taken per one-time dose [6]. A standard 12-capsule regimen is expected to deliver approximately $4.2\times10^9$ CFU per dose.

(2) Alter the small intestinal microbiota to promote immunomodulation. An encapsulated formulation releasing contents in the proximal small bowel will deliver a dose of $3-5\times10^9$ CFU, exceeding the duodenal biomass by a factor of 10,000, and approaching a 1:1 ratio with communities in the jejunum and ileum.

Other formulations including nanoparticles in liquid, with optional pre-biotic compounds to enhance colonization and viability, or a reconstituted lyophilisate are contemplated, however given the need to prevent exposure to oxygen and for ease of storage and administration, the first formulation uses encapsulated material.

Administration

Given the obligately anaerobic nature of the component species, phase I studies will use encapsulated formulations with the following properties:

Stage I:

Can be swallowed by an adult or child >8 years of age.

Excludes oxygen

Holds a volume so that a person needs to take 15 or less capsules per dose

Can be stored frozen (–20° C. or –80° C.) and thawed prior to administration

Releases contents after passage through the stomach

In one embodiment, the capsules used by OpenBiome™ for oral FMT therapy are used to encapsulate the GP-I and GP-II mixtures [i]. Other options are also available commercially and contemplated herein. In some embodiments, the capsules consist of frozen material (in order to ensure an adequate product) that is thawed prior to administration and is encapsulated, free of oxygen, with material that survives intact into the small intestine.

Scale of Culture

The animal studies used pilot cultures in the range of 100-1000 mL. To generate human doses, the culture is scaled by at least a factor of 10. The following steps are contemplated herein.

(1) Perform growth curves in different media conditions—to optimize growth conditions and correlate an OD600 with plated biomass.

(2) Grow the component members anaerobically in liquid media. Media is pre-reduced and incubated at 37° C. with some level of agitation (e.g., 150 rpm or with stirring/fermenter baffles) to insure a maximal culture density. Depending upon the fermenter system, nitrogen or anaerobic gas mixtures can be sparged to maintain anaerobic conditions. However, none of the component species require $H_2$ or $CO_2$ for growth, beyond maintaining appropriate acid/base balance.

(3) Concentrate select members as needed to obtain desired input density: commonly done by centrifugation at 5-10K RPM with pull-off of supernatant under anaerobic conditions and resuspension in a lesser volume of new culture media or appropriate suspension buffer. The new culture density is confirmed by OD600 reading and viability by plating to solid media.

(4) Aggregate the cultured into the combined consortium: Estimated biomass from the OD600 readings are used to estimate the volume and prepare the aggregate.

(5) Prepare capsules: done under anaerobic conditions to preserve viability.

(6) Store capsules: optimal to store at conditions available clinically, e.g. –20° C.

(7) Quality Control: In addition to QC for prior steps and media, the final community will be evaluated to insure the appropriate species are present and in desired viable biomass. Analyses on materials for pre-clinical studies used 16S rRNA gene phylotyping with culture a qPCR-based methods. Metagenomic approaches may also be used to rule-out contamination with nonbacterial species or viruses.

It is further contemplated herein that growth conditions are optimized for the scaled cultures.

In some embodiments, media formulations are developed such that they lack animal products and/or substrates that might be associated with sensitizing antigens in foodstuffs. In addition, one of skill in the art can assess if additives to the inoculum enhance viability in capsules and once released in vivo. Materials can include preservatives and prebiotic compounds.

Stage II:

It is further contemplated herein that the consortia described herein are formulated as a liquid formulation that can be administered to infants and young children. It is contemplated herein that such formulations comprise mixtures of spores from sporulating species, leveraging non-sporulating obligate anaerobes with limited aerotolerance, and including reducing factors in a liquid formula to buffer against short-term exposure to oxygen in ambient air and upon entry into the digestive tract. Compounds such as the amino acid cysteine or n-acetylcysteine, which have been used therapeutically in infants and have a robust safety profile are contemplated [7,8].

Additional pre-clinical animal models for use in testing formulations include e.g., neonatal swine models of food allergy, including ones for foodstuffs common in the diet of both humans and pigs [9].

REFERENCES

1. Mathias C B, Hobson S A, Garcia-Lloret M, Lawson G, Poddighe D, Freyschmidt E J, Xing W, Gurish M F, Chatila T A, Oettgen H C. IgE-mediated systemic anaphylaxis and impaired tolerance to food antigens in mice with enhanced IL-4 receptor signaling. J Allergy Clin Immunol. 2011 March; 127(3):795-805.e1-6.
2. Noval Rivas M, Burton O T, Wise P, Zhang Y Q, Hobson S A, Garcia Lloret M, Chehoud C, Kuczynski J, DeSantis T, Warrington J, Hyde E R, Petrosino J F, Gerber G K, Bry L, Oettgen H C, Mazmanian S K, Chatila T A. A microbiota signature associated with experimental food allergy promotes allergic sensitization and anaphylaxis. J Allergy Clin Immunol. 2013 January; 131(1):201-12.
3. Secretions in the G I tract—available on the world wide web at: en.wikibooks.org/wiki/Medical_Physiology/Gastrointestinal_Physiology/Secretions
4. Genes Nutr. 2011 August; 6(3): 209-240
5. Stool substitute transplant therapy for the eradication of *Clostridium difficile* infection: 'RePOOPulating' the gut. Microbiome Journal Open Access (2013) DOI: 10.1186/2049-2618-1-3.

6. Open Biome FMTcapsules F30 and G3: available on the world wide web at openbiome.org/fmtcapsules/
7. Zlotkin, S H, et al. Cysteine supplementation to cysteine-free intravenous feeding regimens in newborn infants. Am J Clin Nutr. 1981, 34(5): 914-923.
8. Marzullo, L. An update of N-acetylcysteine treatment for acute acetaminophen toxicity in children. Curr Op Peds. 2005, 17(2): 239-245.
9. Helm, R H et al. A neonatal swine model for peanut allergy. JACI. 2002, 109(1): 136-142.

Example 2: OTU Clustering Method for Data from Human and Animal Studies

DNA extraction and sequencing for 16S rRNA gene phylotyping. A multiplexed amplicon library covering the V4 region of the 16S rDNA gene was generated from DNA extracted from human stool, mouse fecal pellets or segments of snap-frozen gut tissues using MO BIO™ Power-Fecal™ DNA Isolation Kits (MO BIO™ Laboratories) with custom modification to enhance lysis of Gram positive commensals with thick cell walls. The rest of library preparation followed the protocol of [1] with dual-index barcodes. Aggregated libraries are sequenced with paired-end 250 bp reads on the Illumina™ MiSeq platform. The aggregate library pool was size selected from 300-500 bp on a Pippin™ prep 1.5% agarose cassette (Sage Sciences™) according to the manufacturer's instructions. Concentration of the pool is measured by qPCR (Kapa Biosystems™) and loaded onto the MiSeg™ (Illumina™) at 6-9 pM with 20% phiX spike-in to compensate for low base diversity according to Illumina™'s standard loading protocol.

16S rRNA Data Preprocessing.

Sequencing aims to obtain 10-50K usable reads per sample after quality filtering. Raw sequencing reads were processed using the mothur software package (v.1.35.1)[2] and custom Python and R scripts [3], which perform de-noising, quality filtering, alignment against the ARB Silva reference database of 16S rDNA gene sequences, and clustering into Operational Taxonomic Units (OTUs) at 97% identity.

16S rRNA Data Analysis.

To statistically test for differences between control and food allergic subjects in abundances of microbial taxa (OTUs), the DESeq2 software package was employed to support of analyses relative to host co-variates such as age, food allergy status, diet and antibiotic use in human cohort, OTUs showing significant differences were defined by: (1) adjusted p-value <=0.1; (2) relative abundance >=0.01 in either control or food allergic groups; (3) absolute value of log 2 fold changes >=2.

To improve the resolution of taxonomic calls and show phylogenetic relationships, a separate method used the pplacer software package to perform phylogenetic placement of individual OTU [4]. Pplacer uses a likelihood-based methodology to place short sequencing reads of 16S rRNA amplicons on a reference tree, and also generates taxonomic classifications of the short sequencing reads using a least common ancestor-based algorithm. The reference tree required for phylogenetic placement is generated using full-length or near full-length (>1,200 nt) 16S rDNA sequences of type strains from the Ribosomal Database Project (RDP)[5].

For all statistical testing for 16S rDNA data analysis, p-values were adjusted for multiple hypothesis testing using the method of Benjamin and Hochberg (BH) [6]. Heat map plots are generated using custom R scripts [3].

Alpha diversity values (richness of a sample in terms of the diversity of the OTUs observed in it) were calculated using Shannon entropy to measure diversity in each sample. Beta-diversity values (distance between samples based on differences in OTUs present in each sample) were calculated using the unweighted/weighted Unifrac dissimilarity measure, to assess differences in overall microbial community structure.

(3) OTU Mappings of the Defined Species

The following operational taxonomic units map to the defined species, as identified in gnotobiotic mice colonized with these consortia. Fecal pellets were subjected to the above described 16S rRNA gene phylotyping over the V4 variable region.

TABLE 2

Mapping of the defined therapeutic species to OTU based on the 16S rRNA V4 region.

| Species | OTU taxonomic mappings, V4 region - |
|---|---|
| *Bacteroides fragilis* | Bacteria:Bacteroidetes:<br>Bacteroidia:Bacteroidales<br>Bacteria:Bacteroidetes:<br>Bacteroidia:Bacteroidales:<br>Bacteroidaceae<br>Bacteria:Bacteroidetes:<br>Bacteroidia:Bacteroidales:<br>Bacteroidaceae:Bacteroides |
| *Bacteroides thetaiotaomicron* | Bacteria:Bacteroidetes:<br>Bacteroidia:Bacteroidales<br>Bacteria:Bacteroidetes:<br>Bacteroidia:Bacteroidales:<br>Bacteroidaceae<br>Bacteria:Bacteroidetes:<br>Bacteroidia:Bacteroidales:<br>Bacteroidaceae:Bacteroides |
| *Bacteroides ovatus* | Bacteria:Bacteroidetes:<br>Bacteroidia:Bacteroidales<br>Bacteria:Bacteroidetes:<br>Bacteroidia:Bacteroidales:<br>Bacteroidaceae<br>Bacteria:Bacteroidetes:<br>Bacteroidia:Bacteroidales:<br>Bacteroidaceae:Bacteroides |
| *Clostridium bifermentans* | Bacteria:Firmicutes:<br>Clostridia:Clostridiales:<br>Peptostreptococcaceae<br>Bacteria:Firmicutes:<br>Clostridia:Clostridiales:<br>Peptostreptococcaceae:<br>*Clostridium* cluster XI |
| *Clostridium hiranonsis* | Bacteria:Firmicutes:<br>Clostridia:Clostridiales:<br>Peptostreptococcaceae<br>Bacteria:Firmicutes:<br>Clostridia:Clostridiales:<br>Peptostreptococcaceae:<br>*Clostridium* cluster XI |
| *Clostridium leptum* | Bacteria:Firmicutes:<br>Clostridia:Clostridiales:<br>Ruminococcaceae<br>Bacteria:Firmicutes:<br>Clostridia:Clostridiales:<br>Ruminococcaceae:<br>*Clostridium* cluster IV |
| *Clostridium ramosum* | Bacteria:Firmicutes:<br>Erysipelotrichia:<br>Erysipelotrichales:<br>Erysipelotrichaceae<br>Erysipelotrichales:<br>Erysipelotrichaceae:<br>Clostridium cluster XVIII |

TABLE 2-continued

Mapping of the defined therapeutic species to OTU based on the 16S rRNA V4 region.

| Species | OTU taxonomic mappings, V4 region - |
|---|---|
| Clostridium sardiniensis (absonum) | Bacteria:Firmicutes: Clostridia:Clostridiales: Bacteria:Firmicutes: Clostridia:Clostridiales: Clostridiaceae I |
| Clostridium scindens | Bacteria:Firmicutes: Clostridia:Clostridiales: Lachnospiraceae Bacteria:Firmicutes: Clostridia:Clostridiales: Lachnospiraceae: Clostridium cluster XIVa |
| Parabacteroides goldsteinii | Bacteria:Bacteroidetes: Bacteroidia:Bacteroidales: Porphyoromondaceae Bacteria:Bacteroidetes: Bacteroidia:Bacteroidales: Porphyoromondaceae: Parabacteroides |
| Prevotella tannerae | Bacteria:Bacteroidetes: Bacteroidia:Bacteroidales: Bacteria:Bacteroidetes: Bacteroidia:Bacteroidales: Prevotellaceae Bacteria:Bacteroidetes: Bacteroidia:Bacteroidales: Prevotellaceae: Prevotella |

TABLE 3

Mapping of the dysbiotic consortium species to OTU based on the 16S rRNA V4 region

| Species | OTU mapping |
|---|---|
| Bilophila wadsworthia | Bacteria:Proteobacteria: Deltaproteobacteria: Desulfovibrionales Bacteria:Proteobacteria: Deltaproteobacteria: Desulfovibrionales: Desolfovibrionaceae Bacteria:Proteobacteria: Deltaproteobacteria: Desulfovibrionales: Desolfovibrionaceae: Bilophila |
| Enterobacter cloacae | Bacteria:Proteobacteria: Gammaproteobacteria: Enterobacteriales Bacteria:Proteobacteria: Gammaproteobacteria: Enterobacteriales: Enterobacteriaceae Bacteria:Proteobacteria: Gammaproteobacteria: Enterobacteriales:: Enterobacteriaceae Enterbacter |
| Escherichia coli | Bacteria:Proteobacteria: Gammaproteobacteria: Enterobacteriales Bacteria:Proteobacteria: Gammaproteobacteria: Enterobacteriales: Enterobacteriaceae Bacteria:Proteobacteria: Gammaproteobacteria: Enterobacteriales: Enterobacteriaceae: Escherichia |

TABLE 3-continued

Mapping of the dysbiotic consortium species to OTU based on the 16S rRNA V4 region

| Species | OTU mapping |
|---|---|
| Klebsiella pneumonia | Bacteria:Proteobacteria: Gammaproteobacteria: Enterobacteriales Bacteria:Proteobacteria: Gammaproteobacteria: Enterobacteriales: Enterobacteriaceae Bacteria:Proteobacteria: Gammaproteobacteria: Enterobacteriales: Enterobacteriaceae: Klebsiella |
| Proteus mirabilis | Bacteria:Proteobacteria: Gammaproteobacteria: Enterobacteriales Bacteria:Proteobacteria: Gammaproteobacteria: Enterobacteriales: Enterobacteriaceae Bacteria:Proteobacteria: Gammaproteobacteria: Enterobacteriales:: Enterobacteriaceae Proteus |

TABLE 4

Additional "beneficial" OTU identified in the longitudinal pediatric human cohort as associated with protection from development of food allergy.

| OTU taxonomic mappings with sequencing of the V4 region - | Nearest species mapping(s) with pplacer |
|---|---|
| Bacteria:Firmicutes:Clostridia: Clostridiales:Lachnospiraceae | Clostridium hathewayi |
| Bacteria:Firmicutes:Clostridia: Clostridiales:Lachnospiraceae: Clostridium cluster XIVa | |
| Bacteria:Firmicutes:Clostridia: Clostridiales:Lachnospiraceae: Hungatella | |
| Bacteria:Firmicutes:Clostridia: Clostridiales:Lachnospiraceae | Clostridium nexile, |
| Bacteria:Firmicutes:Clostridia: Clostridiales:Lachnospiraceae: Clostridium cluster XIVa | Clostridium hylemonae, Clostridium glycyrrhizinilyticum, Clostridium scindens, Clostridium lavalense, Clostridium fimetarium, Clostridium symbiosum |
| Bacteria:Firmicutes:Clostridia: Clostridiales:Ruminococcaceae | Clostridium sporosphaeroides |
| Bacteria:Firmicutes:Clostridia: Clostridiales:Ruminococcaceae: Clostridium cluster IV | |
| Bacteria:Firmicutes:Negativicutes: Selenomonadales:Veillonellaceae | Dialister proprionicifaciens, |
| Bacteria:Firmicutes:Negativicutes: Selenomonadales:Veillonellaceae: Dialister | Dialister succinatiphilus |
| Bacteria:Bacteroidetes:Bacteroidia: Bacteroidales:Porphyoromondaceae Bacteria:Bacteroidetes:Bacteroidia: Bacteroidales:Porphyoromondaceae: Parabacteroides | Parabacteroides distasonis, Parabacteroides goldsteinii, Parabacteroides merdae |

TABLE 4-continued

Additional "beneficial" OTU identified in the longitudinal pediatric human cohort as associated with protection from development of food allergy.

| OTU taxonomic mappings with sequencing of the V4 region - | Nearest species mapping(s) with pplacer |
|---|---|
| Bacteria:Firmicutes:Clostridia: Clostridiales:Peptostreptococcaceae | *Peptostreptococcus anaerobius* |
| Bacteria:Firmicutes:Clostridia: Clostridiales:Peptostreptococcaceae: *Peptostreptococcus* | |
| Bacteria:Firmicutes:Clostridia: Clostridiales:Ruminococcaceae | *Subdoligranulum variabile* |
| Bacteria:Firmicutes:Clostridia: Clostridiales:Ruminococcaceae: *Subdoligranulum* | *Veilonella ratti* |
| Bacteria:Firmicutes:Negativicutes: Selenomonadales:Veillonellaceae | |
| Bacteria:Firmicutes:Negativicutes: Selenomonadales:Veillonellaceae: *Veillonella* | |

TABLE 5

Additional "dysbiotic" OTU identified in the longitudinal pediatric human cohort as associated with development of food allergy.

| OTU taxonomic mappings with sequencing of the V4 region | Nearest species mapping with pplacer |
|---|---|
| Bacteroidetes:Bacteroidia: Bacteroidales:Rikenellaceae: | *Alistipes onderdonkii* |
| Bacteroidetes:Bacteroidia: Bacteroidales:Rikenellaceae:*Alistipes* | |
| Firmicutes:Clostridia: Clostridiales:Lachnospiraceae | *Blautia wexlerae*, |
| Firmicutes:Clostridia:Clostridiales: Lachnospiraceae:*Blautia* | *Blautia henselae* |
| Bacteria:Proteobacteria: Deltaproteobacteria:Desulfovibrionales | *Bilophila wadsworthia*, |
| Bacteria:Proteobacteria: Deltaproteobacteria:Desulfovibrionales: Desolfovibrionaceae | |
| Bacteria:Proteobacteria: Deltaproteobacteria:Desulfovibrionales: Desolfovibrionaceae:*Bilophila* | *Desulfovibrio species* |
| Bacteria:Proteobacteria: Deltaproteobacteria:Desulfovibrionales: Desolfovibrionaceae: *Bilophila:Desulfovibrio* | |
| Firmicutes:Bacilli:Lactobacillales: Lactobacillaceae:*Lactobacillus* | *Lactobacillus johnsoni* |
| Bacteria:Proteobacteria: Betaproteobacteria:Burkholderales: | *Parasutterella excrementihominis* |
| Bacteria:Proteobacteria: Betaproteobacteria:Burkholderales: Sutterellaceae | |
| Bacteria:Proteobacteria:Betaproteo- bacteria:Burkholderales:Sutterellaceae: *Parasutterella* | |
| Firmicutes:Clostridia:Clostridiales: Lachnospiraceae | *Roseburia inulinivorans* |
| Firmicutes:Clostridia:Clostridiales: Lachnospiraceae:*Roseburia* | |

REFERENCES

1. Kozich, J. J., et al., *Development of a dual-index sequencing strategy and curation pipeline for analyzing amplicon sequence data on the MiSeq Illumina sequencing platform.* Applied and environmental microbiology, 2013. 79(17): p. 5112-5120.
2. Schloss, P. D., et al., *Introducing mothur: open-source, platform-independent, community-supported software for describing and comparing microbial communities.* Appl Environ Microbiol, 2009. 75(23): p. 7537-41.
3. McMurdie, P. and S. Holmes, *phyloseq: An R package for reproducible interactive analysis and graphics of microbiome census data.* PloS ONE, 2013. 8(4): p. e61217.
4. Matsen, F., R. B. Kodner, and E. V. Armbrust, *pplacer: linear time maximum-likelihood and Bayesian phylogenetic placement of sequences onto a fixed reference tree.* BMC bioinformatics, 2010. 11(1): p. 538.
5. Cole, J. R., et al., *Ribosomal Database Project: data and tools for high throughput rRNA analysis.* Nucleic acids research, 2014. 42(D1): p. D633-42.
6. Benjamini, Y. and Y. Hochberg, *Controlling the false discovery rate: a practical and powerful approach to multiple testing.* Journal of the Royal Statistical Society Series B, 1995. 57(1): p. 289-300.

Example 3: Microbiology-Level Activities Used in Selection of Defined Species

The species in the defined consortia were selected per known biochemical, immunologic and microbiologic functions with capacity to affect beneficial immunomodulatory responses in the host. Without wishing to be bound by theory, microbiologic mechanisms of action can include the following.

Adjuvant Effects of Microbial Products to Stimulate the Development of Regulatory T Cells through TLR→MyD88 and other immune cell pathways.

The production of key microbial antigens from commensal anaerobes, including their lipoteichoic acid (LTA), exopolysaccharides (PSA), LPS, bacterial flagellin, and bacterial DNA can act through stimulating toll-like-receptor pathways to skew mucosal T cells to a regulatory vs. allergic phenotype. In contrast, published data have shown that bacterial cell wall fractions from members of the negative control consortium can promote aberrant stimulation of both allergic (Th2) and pro-inflammatory (Th1) responses. The distinct portions of these molecules that skew towards tolerance vs. allergy or inflammation highlight the interplay between mammalian hosts and colonizing microbiota, including the microbial products that signal the host to maintain a healthy homeostasis versus elicit pathogenic immune responses.

Mucosal and Immunoprotective Functions of Microbial End-Products of Metabolism:

Short chain fatty acids (SCFA) are natural end-products of microbial anaerobic fermentation as are additional small molecule metabolites from anaerobic fermentation of different carbon sources. End-products such as butyrate have been shown to provide a primary energy source to the gut epithelium and to contribute to the development of tolerizing responses in mucosal locations. The consortia selected produce a dominance of butyrate and propionate from the fermentation of simple and complex carbohydrates that may be in the gut lumen, per the diet and secretion of host factors. These factors would likely act in combination with other microbial activities to mediate the desired immunomodulatory effects.

Biochemical Activities:

The species selected perform the full complement of bile acid transformations and also transform a variety of other molecules including other cholesterol-derivatives, biogenic amines, lipids and production of aryl hydrocarbons which may serve as microbial siderophores, quorum sensing molecules and other metabolic intermediates within the microbial cell. Such metabolites are potentially capable of stimulating host aryl-hydrocarbon receptor (AHR) pathways which have also been demonstrated to promote tolerizing responses in the gut mucosa.

Gut Conditioning:

Microbiologically, select members of the consortia are known to aid the subsequent colonization, biochemical and further immunoprotective roles of other species. Both *Bacteroides fragilis* and *Bacteroides thetaiotaomicron*, when included in defined flora, assist the growth of more fastidious members of the *Bacteroidetes*, Firmicutes and Actinobacteria. *Clostridium ramosum* has demonstrated comparable effects in defined colonizations of germ-free mice with other commensals. Effects are multi-factorial, and include maturing of gut epithelial responses, altered host secretion of glycoconjugates which can serve as carbon sources for the commensal flora, enhancing gut peristalsis and digestion, reducing lumen gut oxygen tension so more obligately anaerobic species can flourish, and releasing metabolites, and/or extracellular products of microbial digestion which support the growth of additional species by providing carbon and/or nitrogen sources, vitamins, and other essential micronutrients.

Reducing the Biomass of Dysbiotic or Pathogenic Species:

Animal models conducted by our group have also shown that the species in the gut protect communities can reduce the biomass of the Proteobacterial species in the negative control consortium. Without wishing to be bound by theory, mechanistically these biomass reductions also reduce the antigen burden of products from these species that preferentially skew towards allergic responses.

Figure 2:
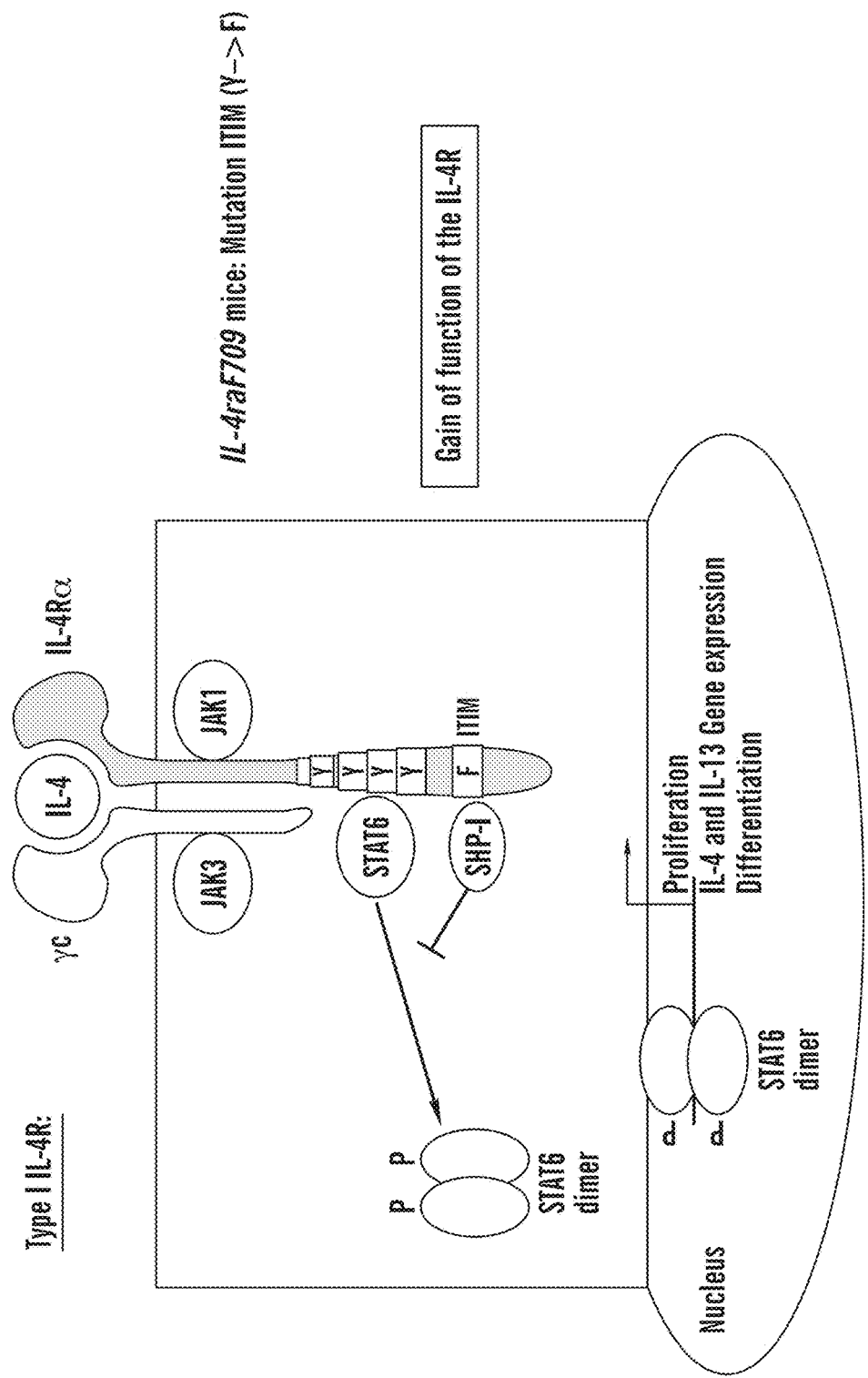
FIG. 2. Experimental model: Il4raF709 mutant mice.
Figure 3:
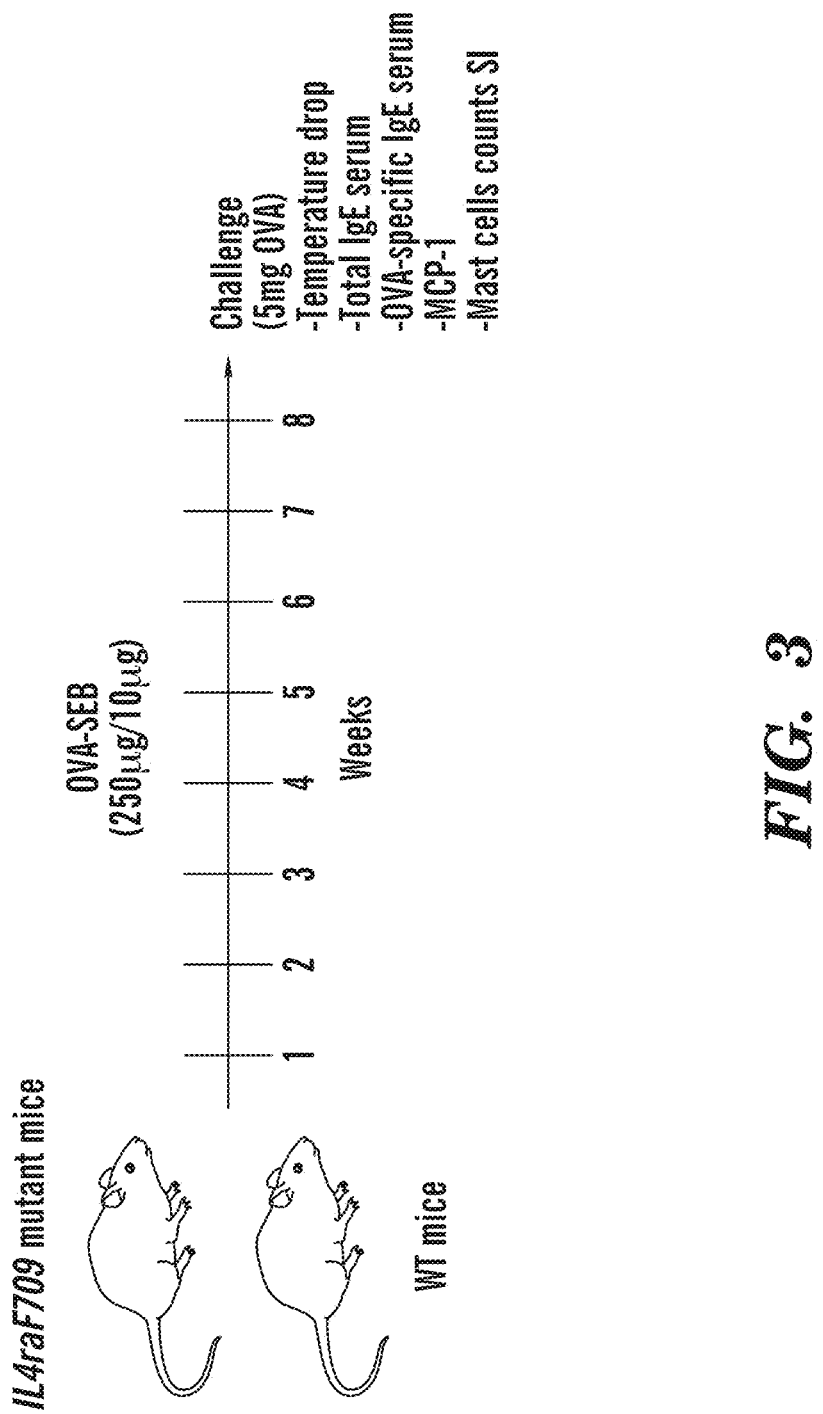
FIG. 3. An exemplary ovalbumin sensitization protocol.
Figure 4:
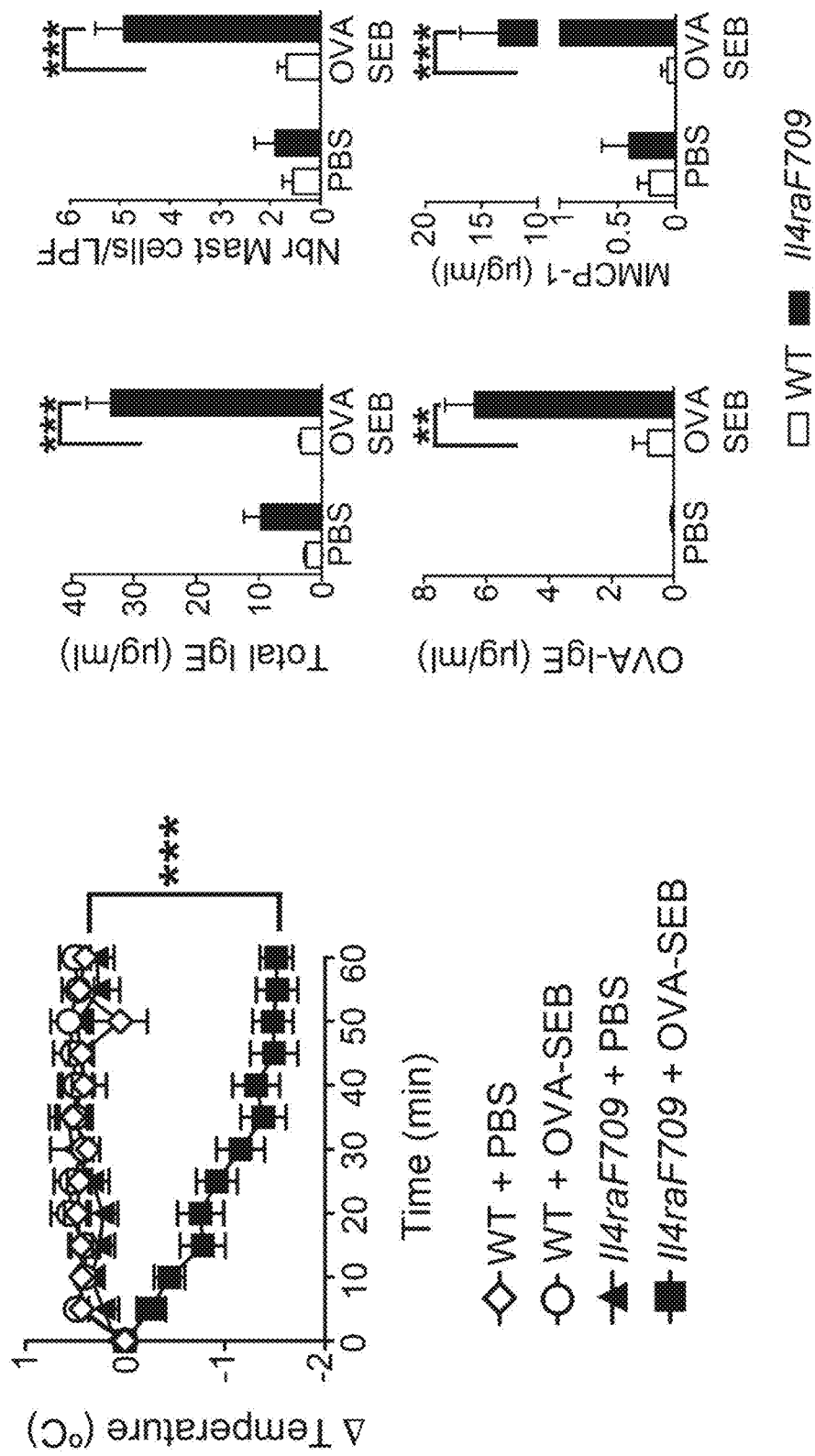
FIG. 4. Ovalbumin (OVA)-induced food allergic reaction in Il4raF709 mice.
Figure 4:
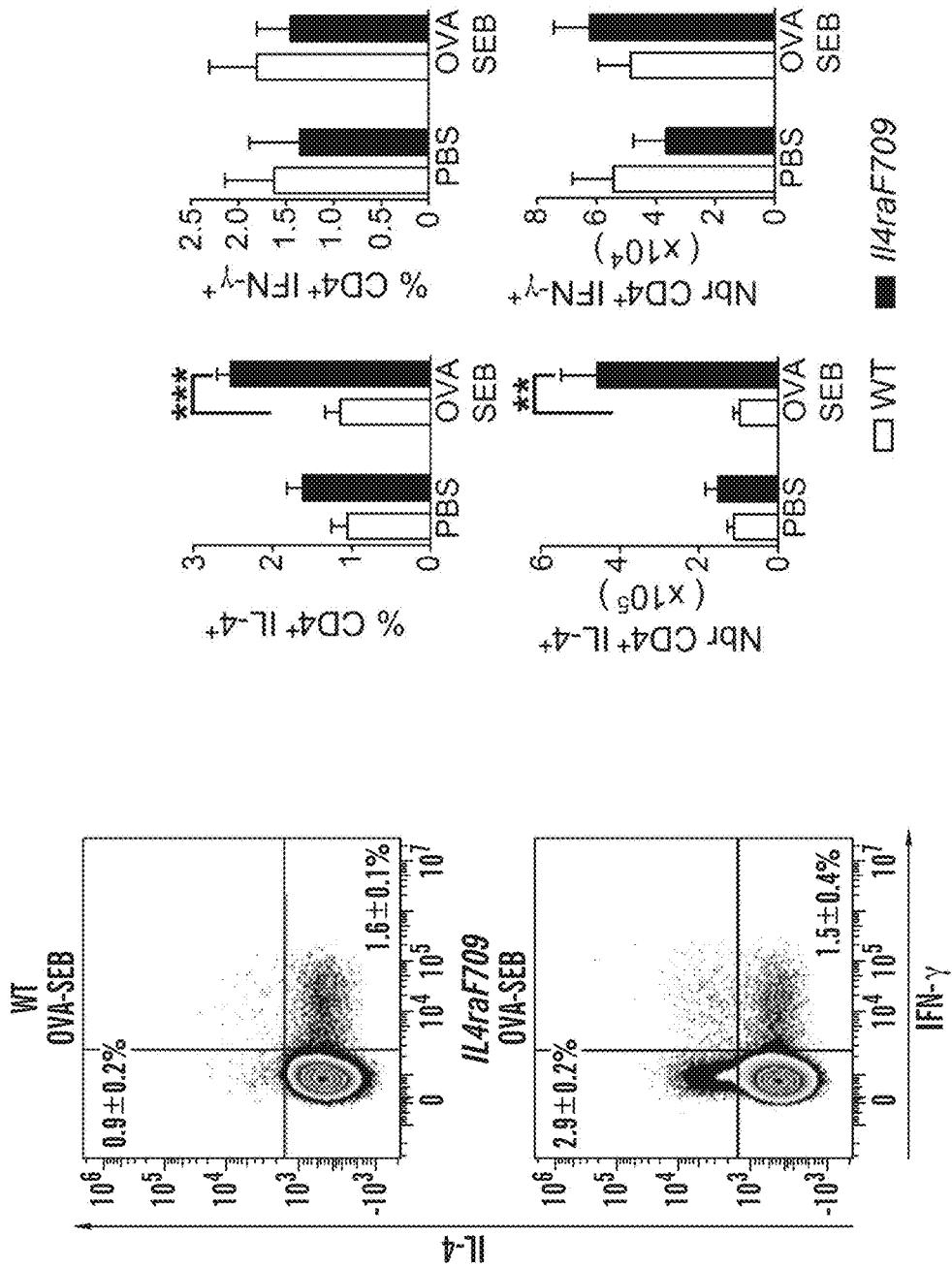
Figure 5:
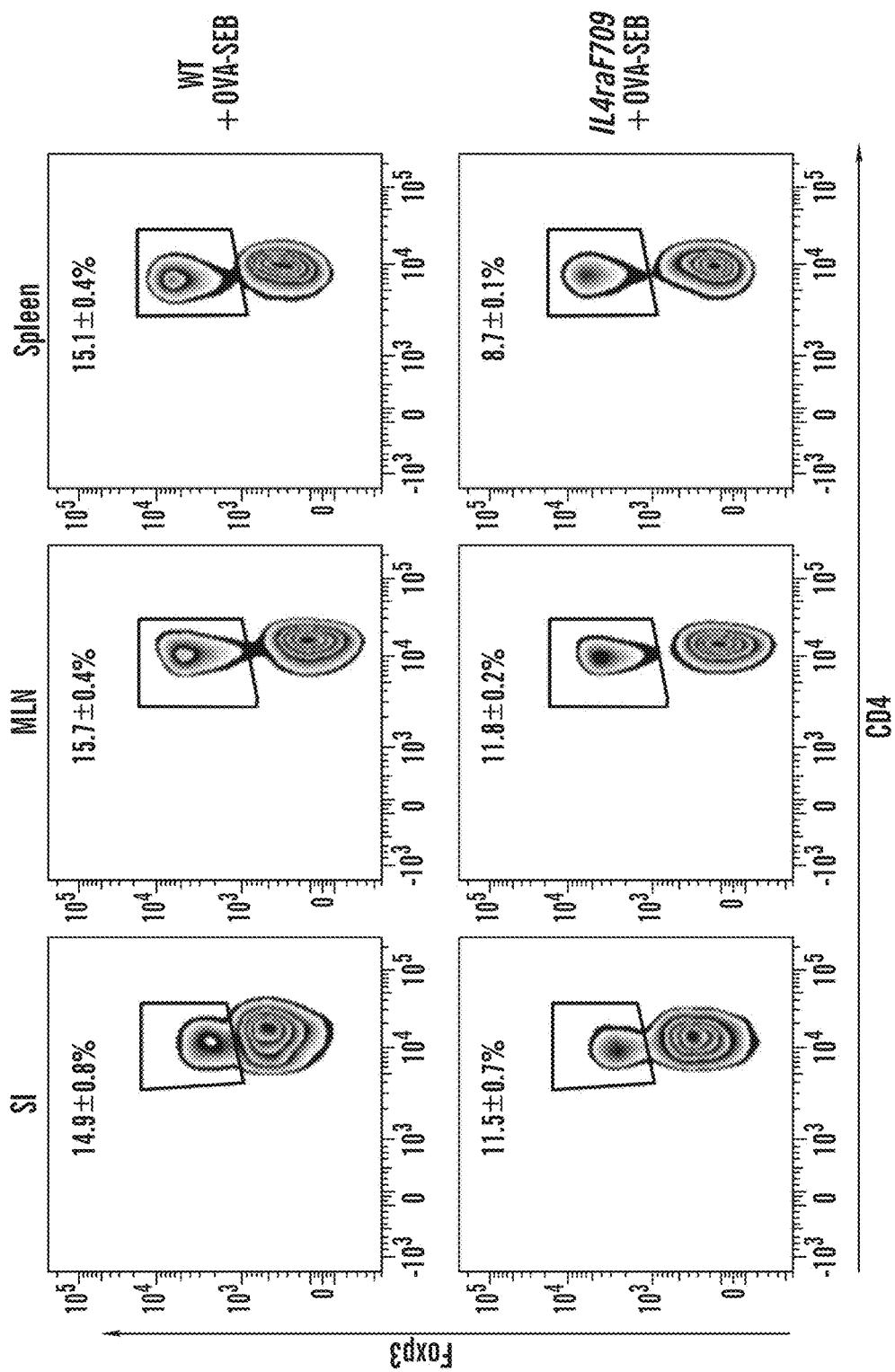
FIG. 5. Allergen-specific $T_R$ cell deficiency in allergic Il4raF709 mice.
Figure 5:
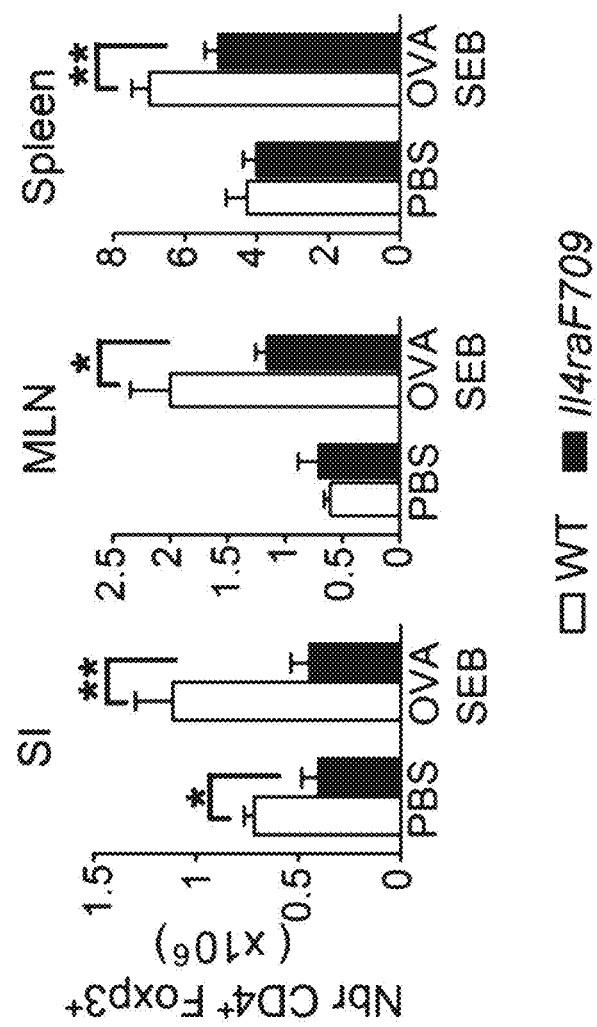
Figure 5:
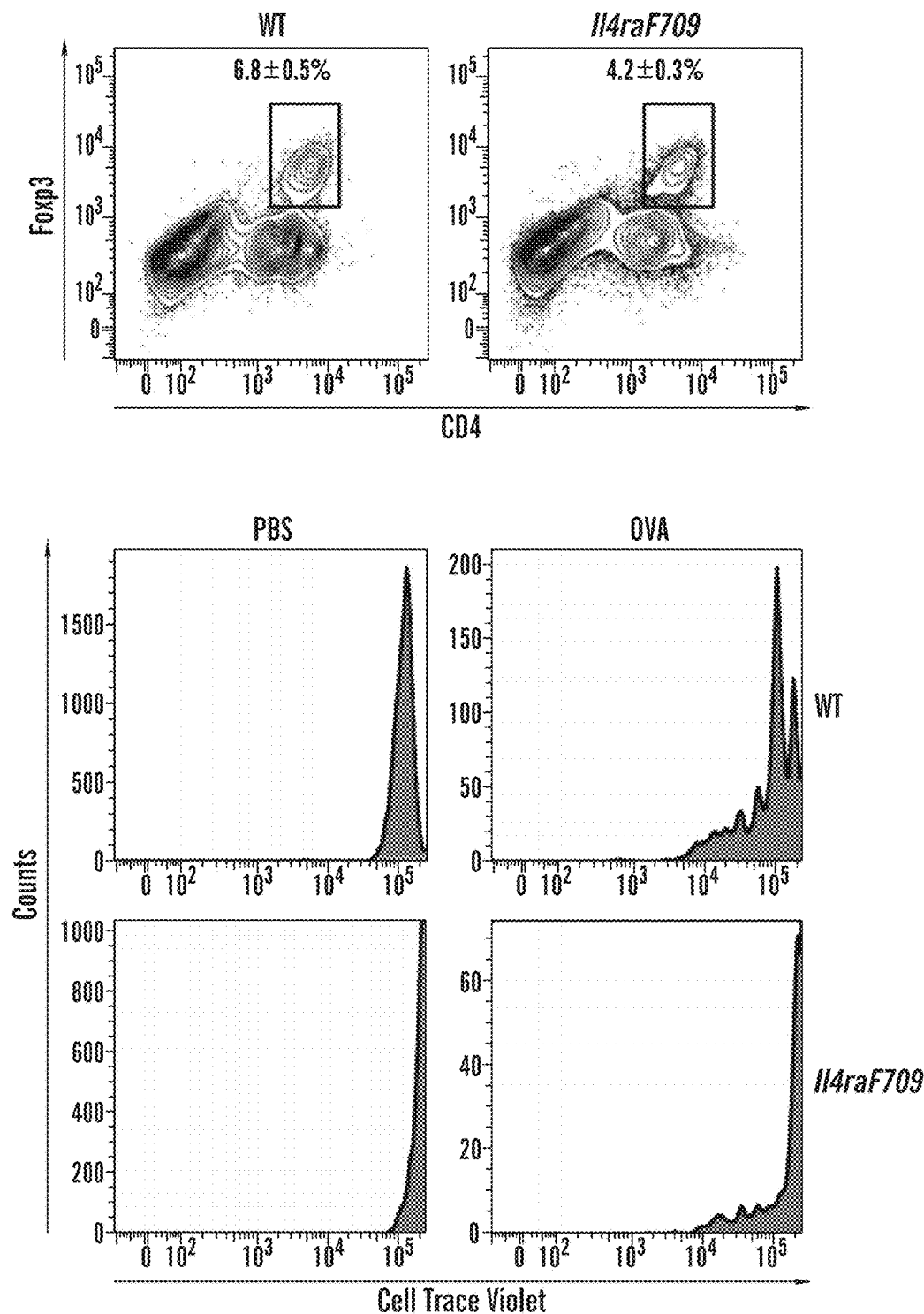
Figure 5:
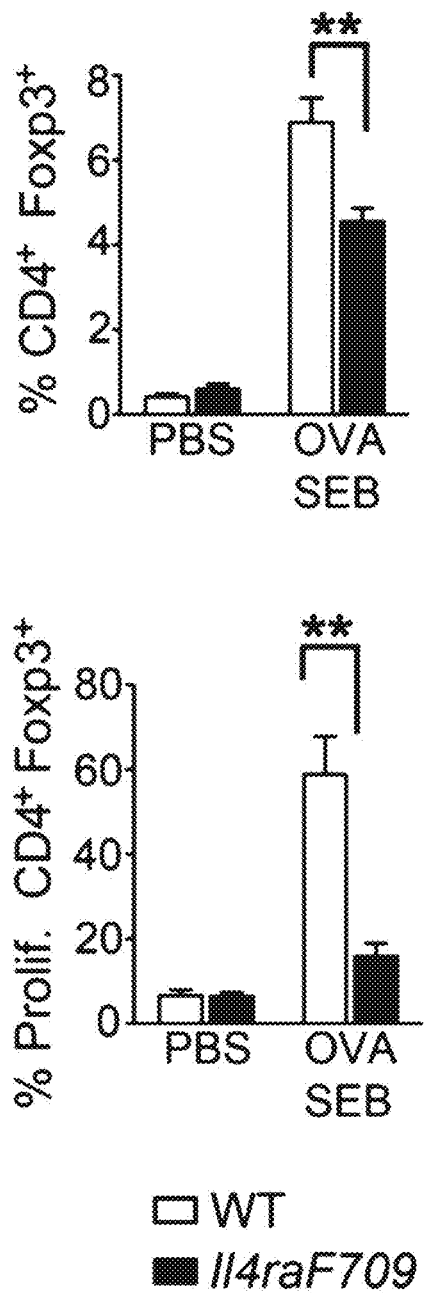
Figure 6:
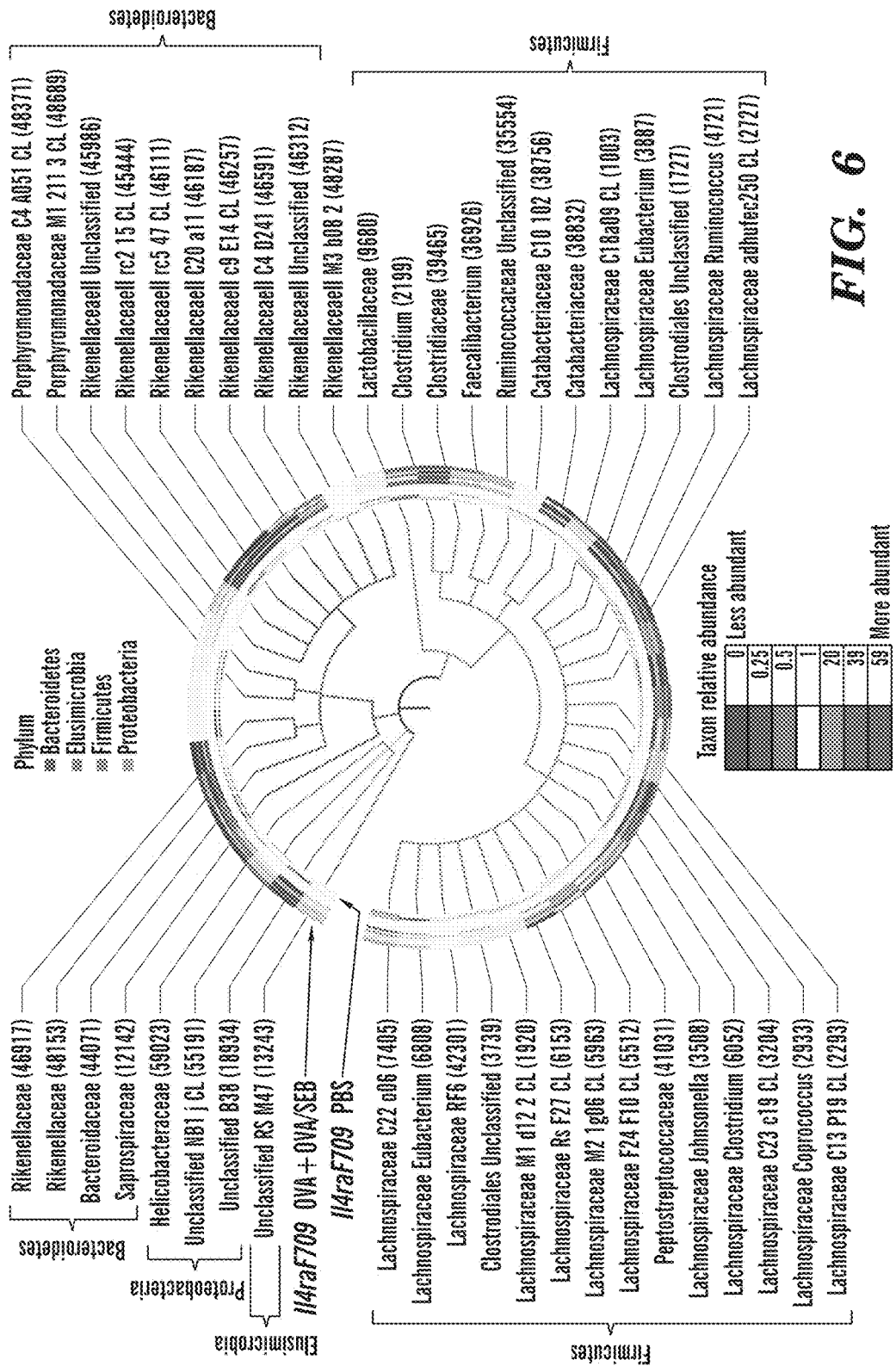
FIG. 6. Oral allergic sensitization in F709 mutant mice is associated with dysbiosis.
Figure 7:
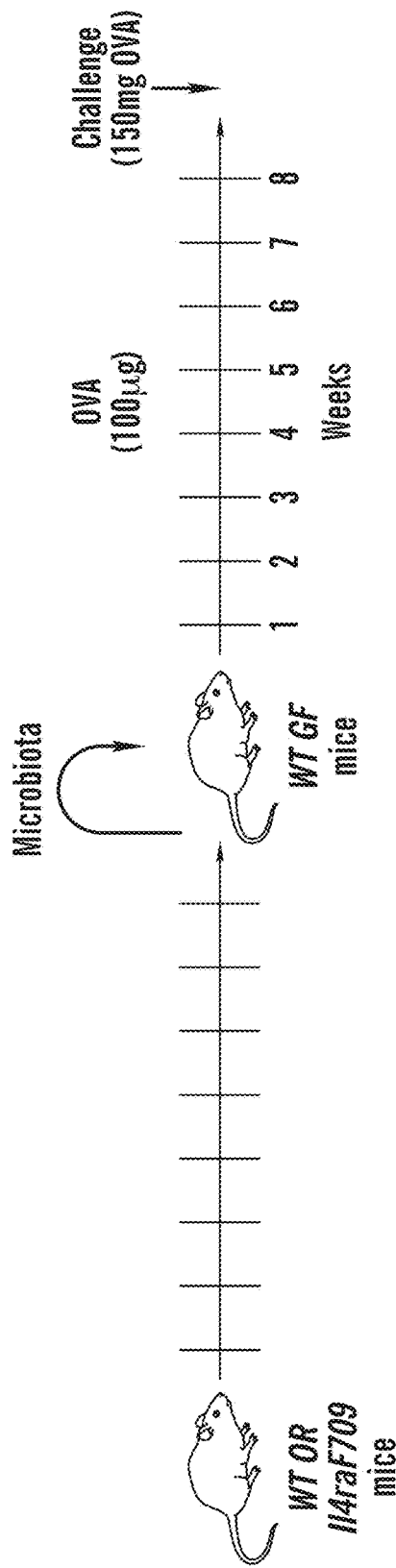
FIG. 7. An exemplary protocol to test if microbiota of sensitized Il4raF709 mice transmit susceptibility to food allergy.
Figure 8:
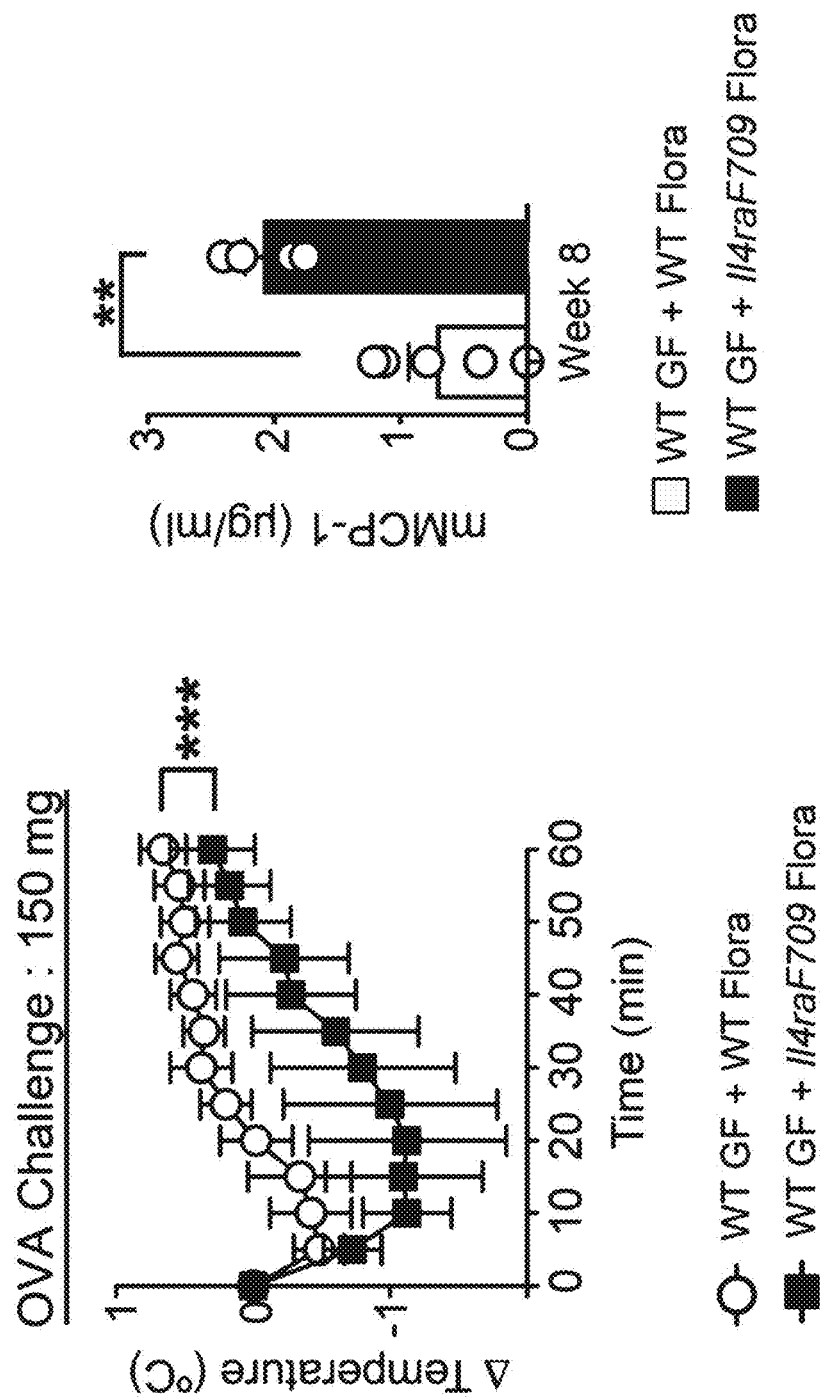
FIG. 8. The microbiota of Il4raF709 mice promotes allergic sensitization and anaphylaxis in germ free mice.
Figure 10:
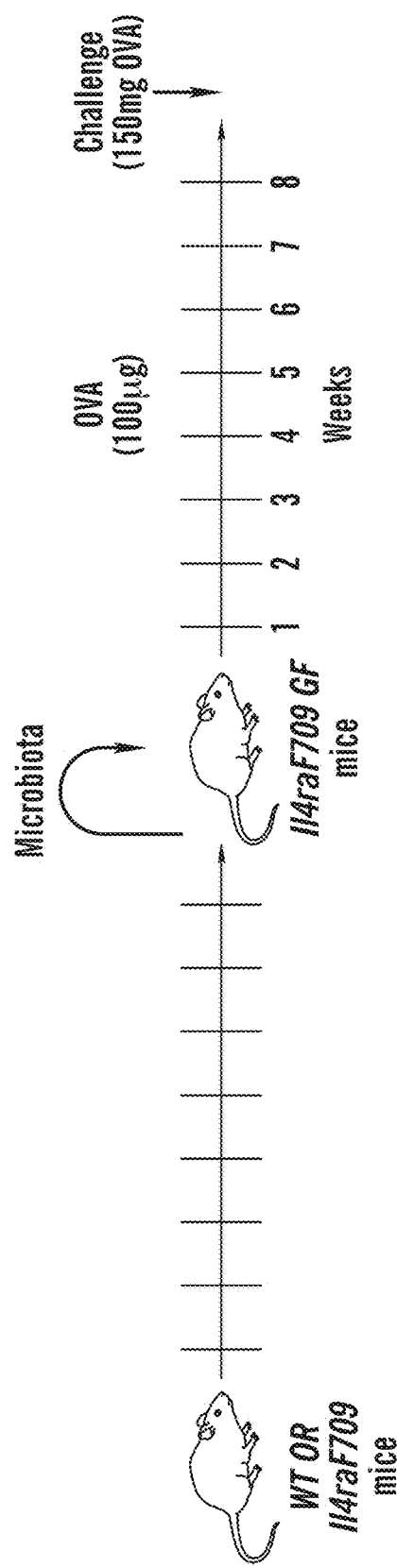
FIG. 10. An exemplary protocol to determine if microbiota of food tolerant mice transmits protection against food allergy.
Figure 11A:
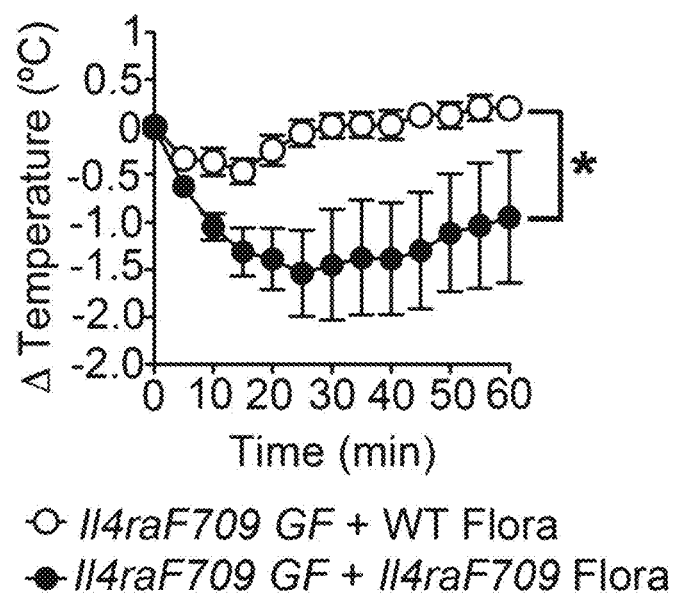
FIG. 11A-FIG. 11D. The microbiota of food tolerant mice protect against allergic sensitization and anaphylaxis in a genetically susceptible host.
Figure 11B:
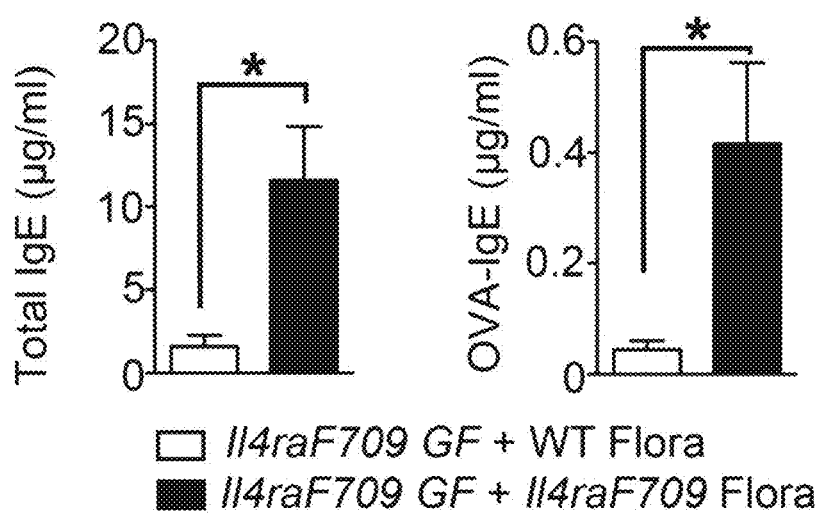
Figure 11C:
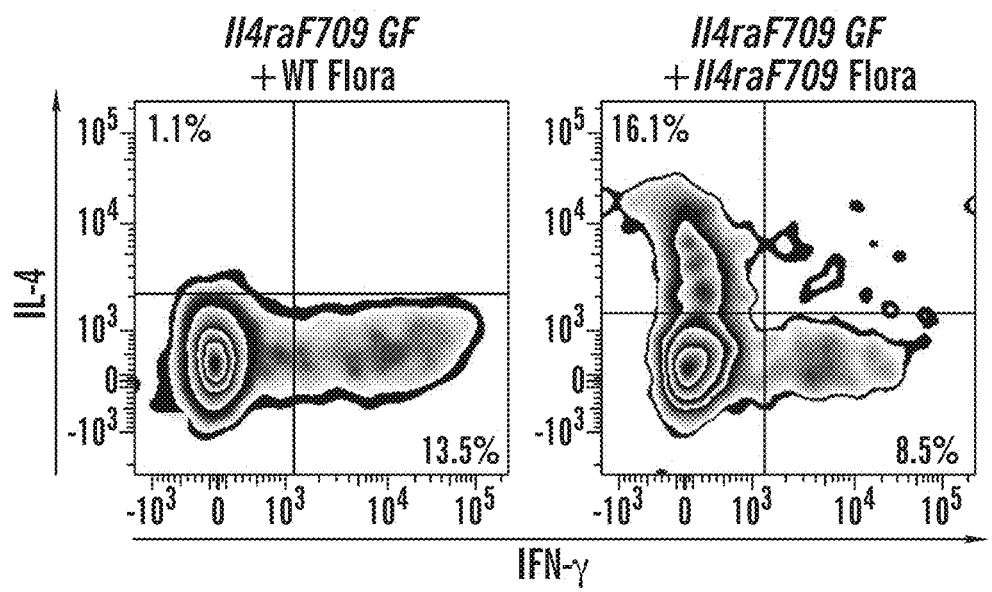
Figure 11D:
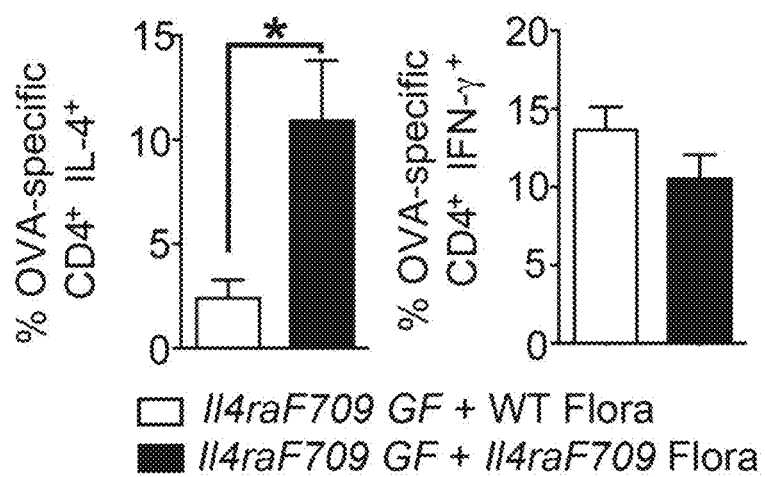
Figure 12A:
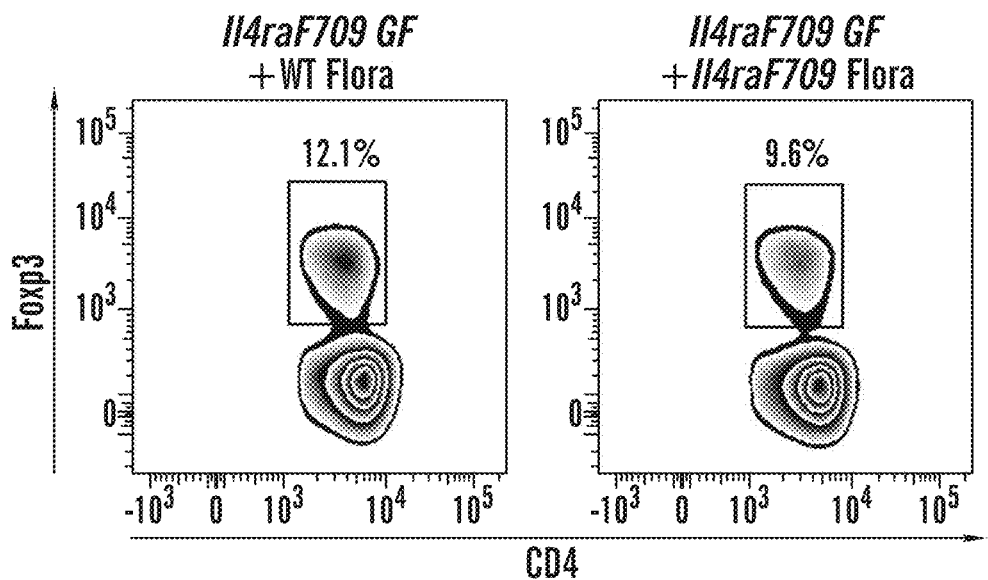
FIG. 12A-FIG. 12D. The microbiota of food tolerant mice promotes the formation of allergen-specific Treg cells.
Figure 12B:
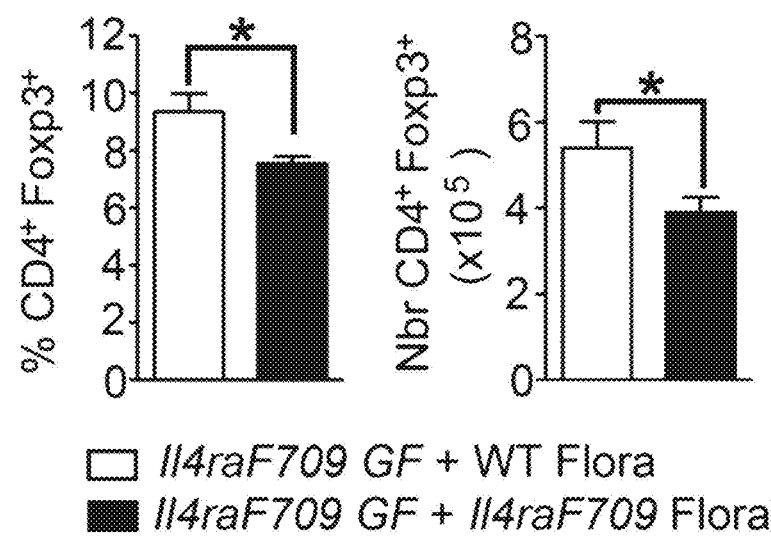
Figure 12C:
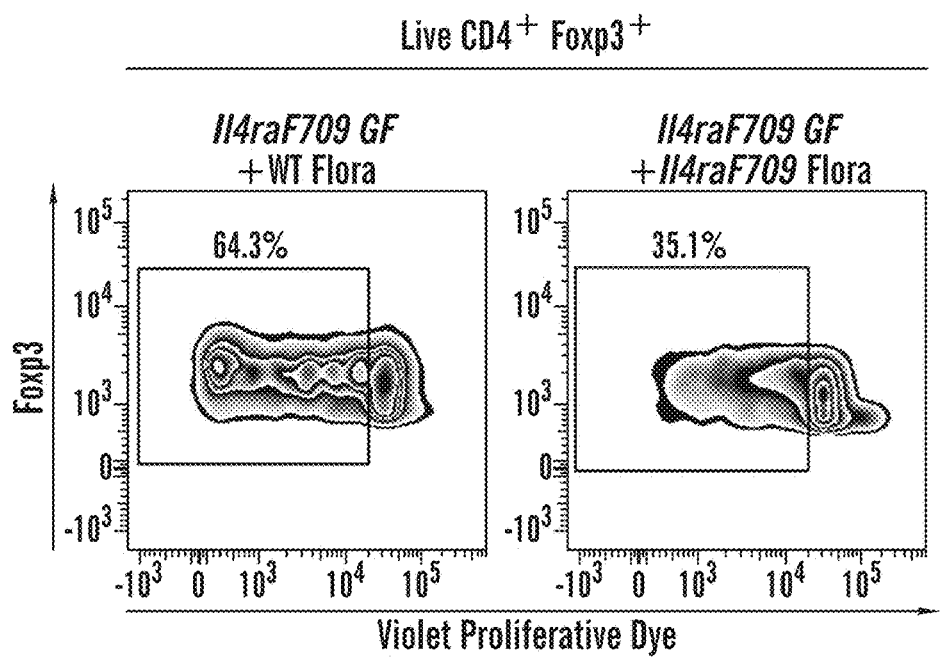
Figure 12D:
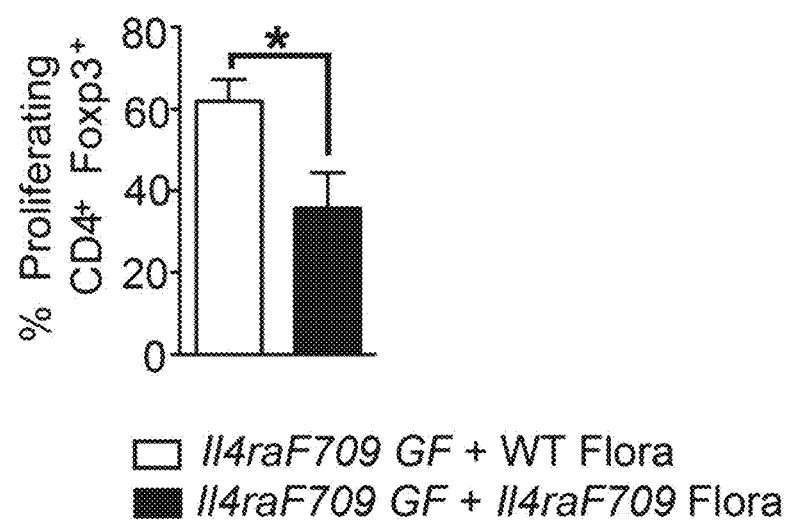
Figure 13:
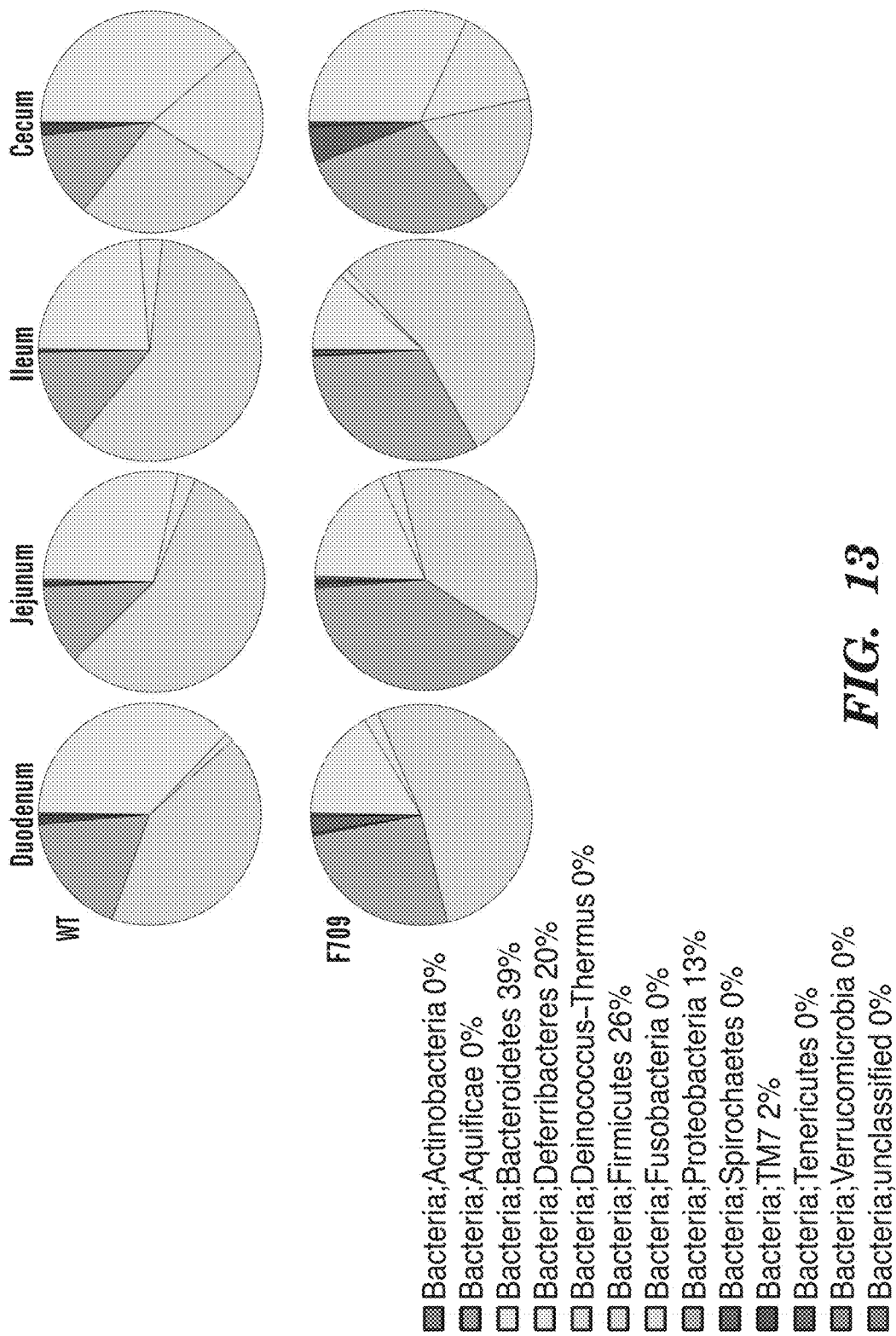
FIG. 13. A graphical visualization of relative abundances of phyla: 8 weeks ovalbumin (OVA) treatment.
Figure 15:
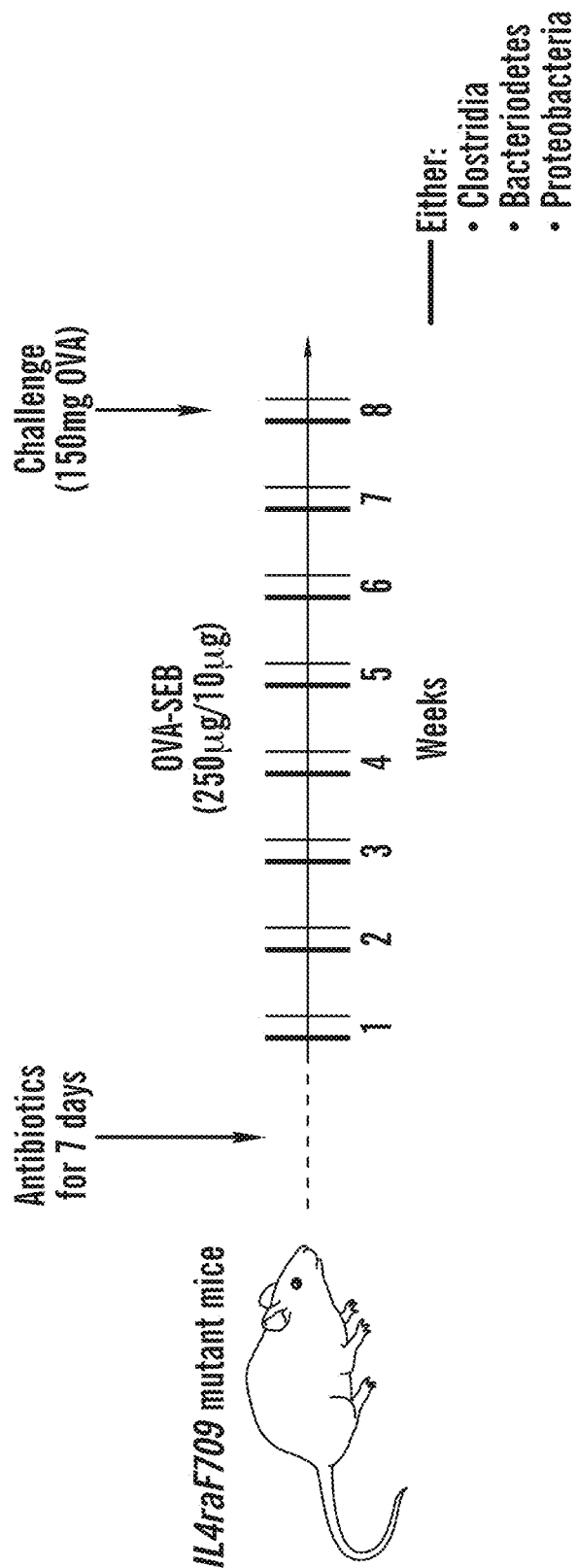
FIG. 15. An exemplary protocol for testing whether treatment with defined bacterial mixes will protect against food allergy.
Figure 16A:
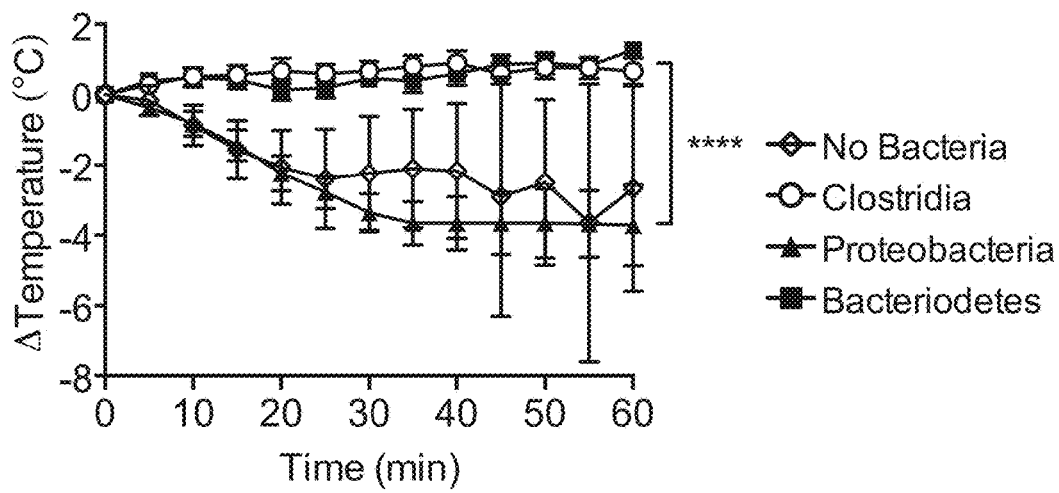
FIG. 16A-FIG. 16D. *Clostridia* and *Bacteriodetes* protect against development of allergen-specific responses and anaphylaxis.
Figure 16B:
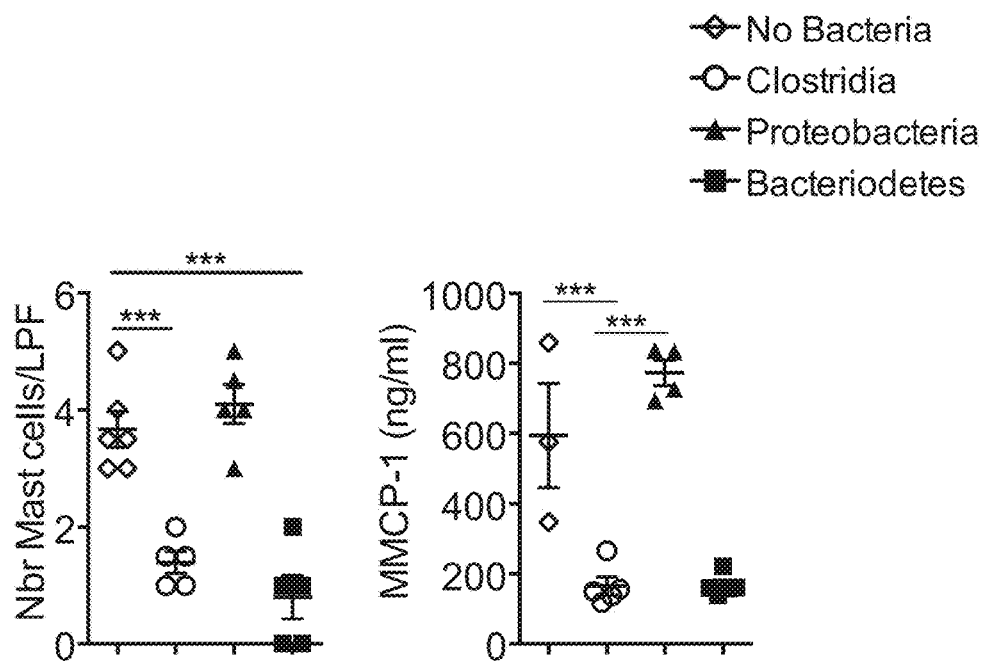
Figure 16C:
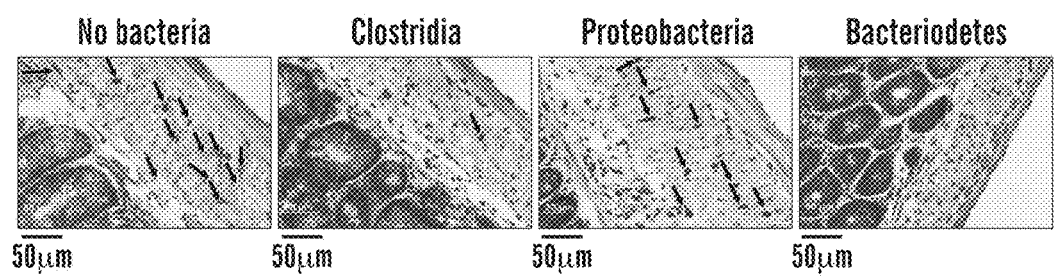
Figure 16D:
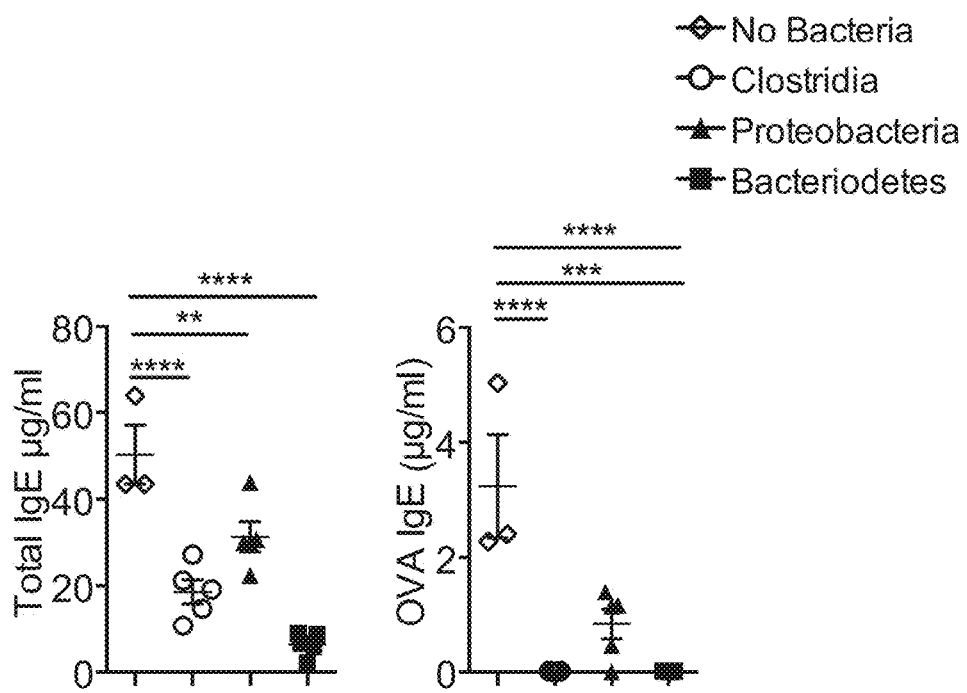
Figure 17:
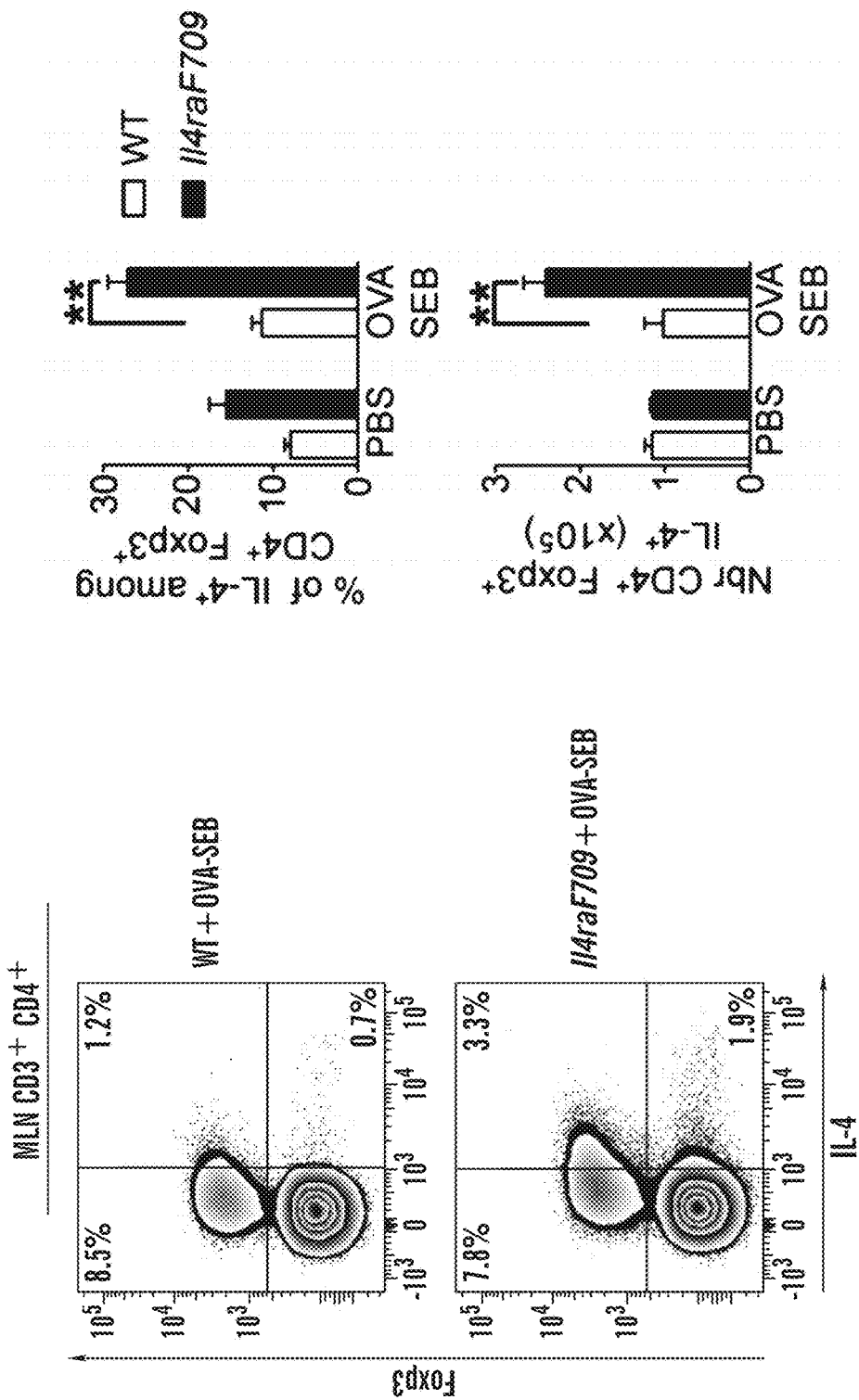
FIG. 17. Oral allergic sensitization is associated with $T_R$ cell TH2 reprogramming.
Figure 17:
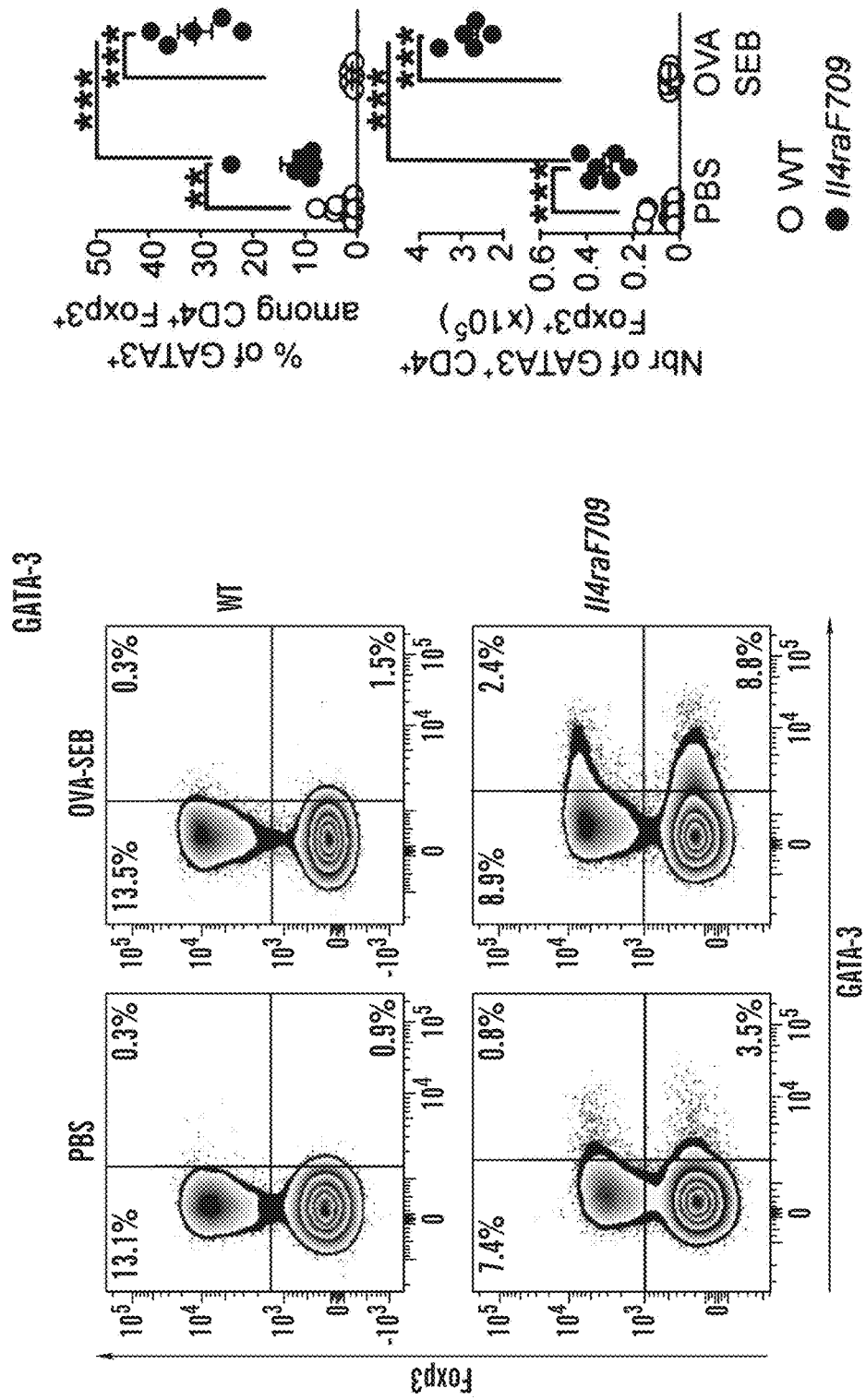
Figure 17:
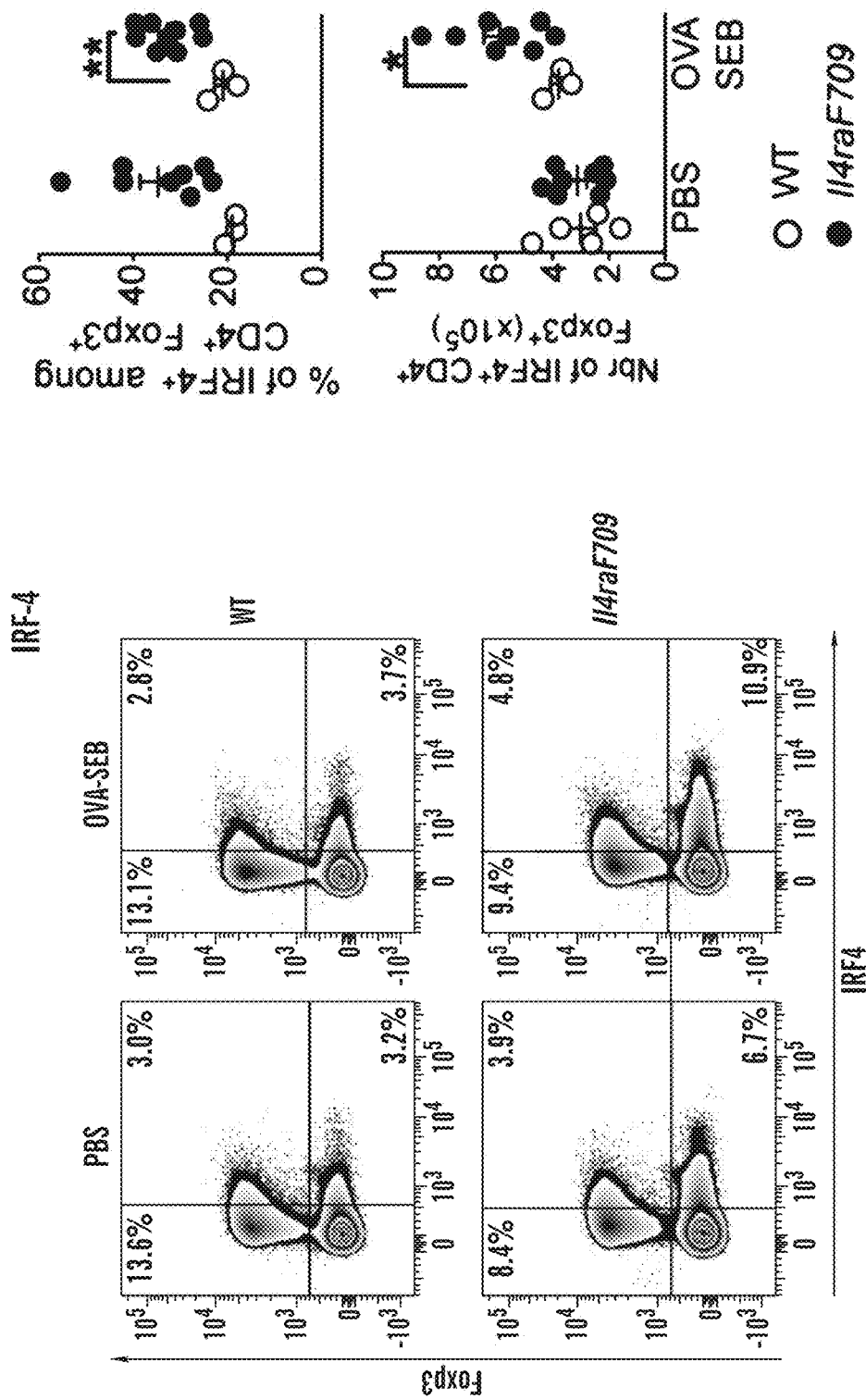
Figures 18D, 18E, 18F:
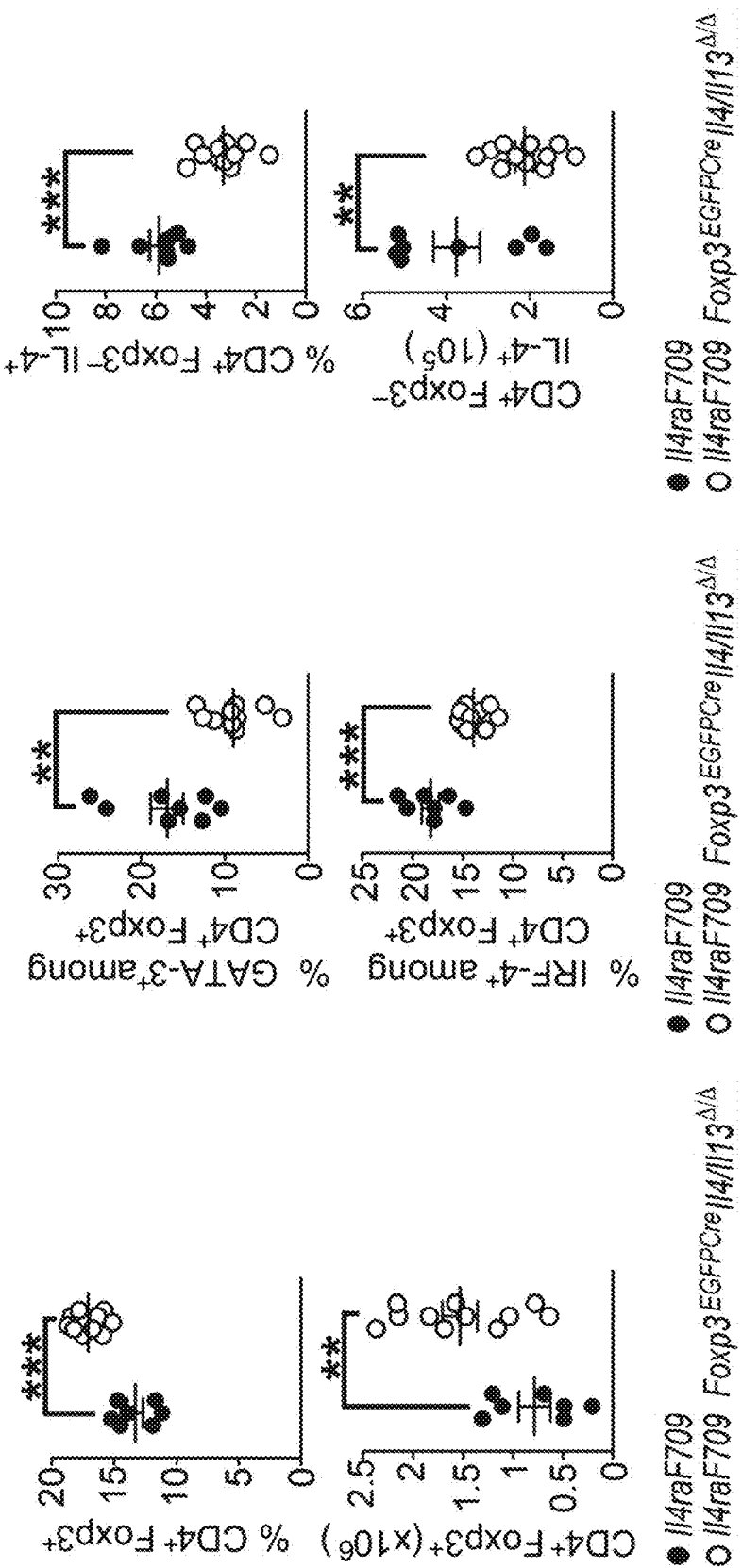
Figure 19:
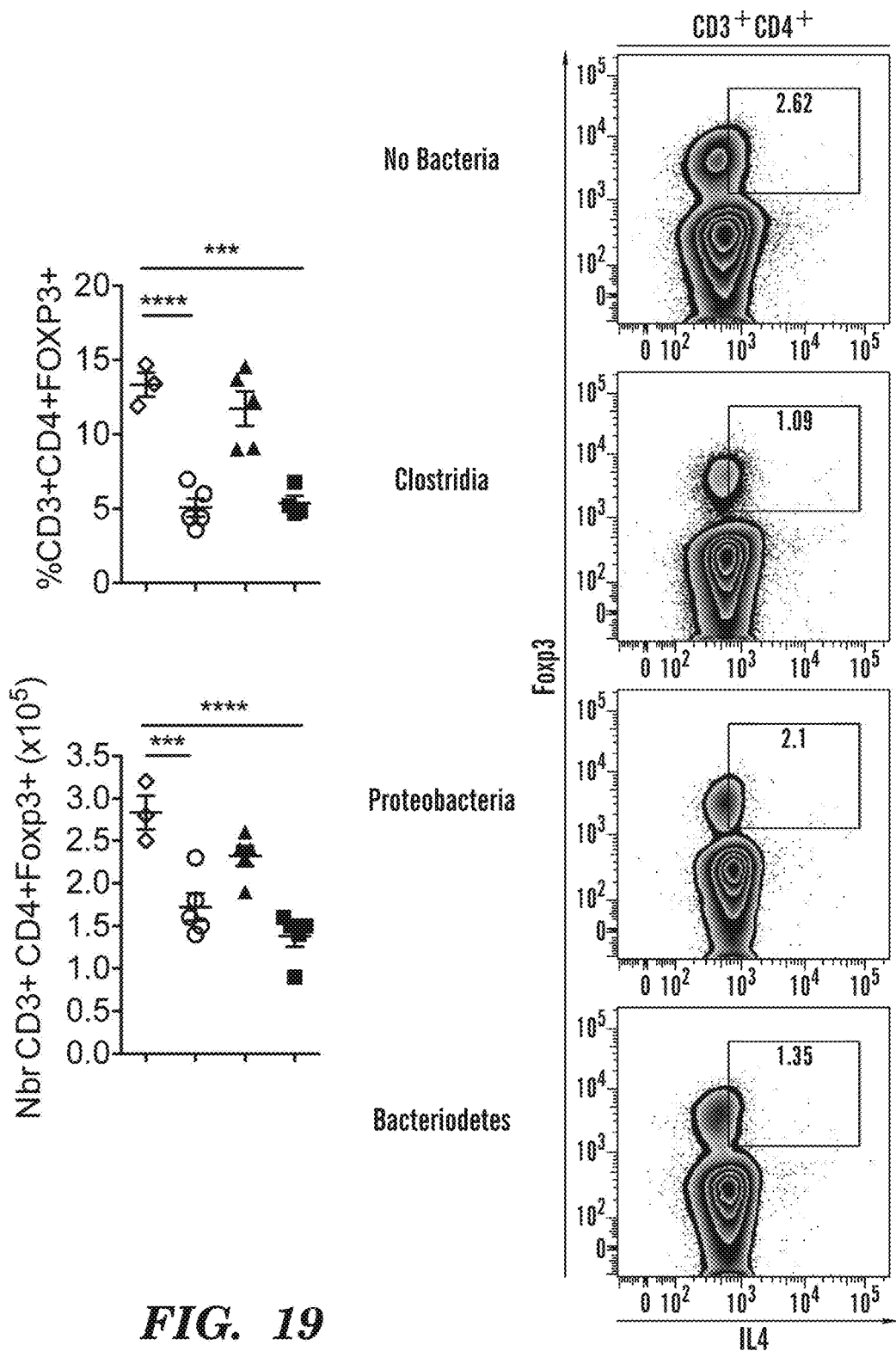
FIG. 19. Reduced TH2-skewed Treg phenotype indicating that *Clostridia* and *Bacteriodetes* have two different molecular mechanisms of action.
Figure 19:
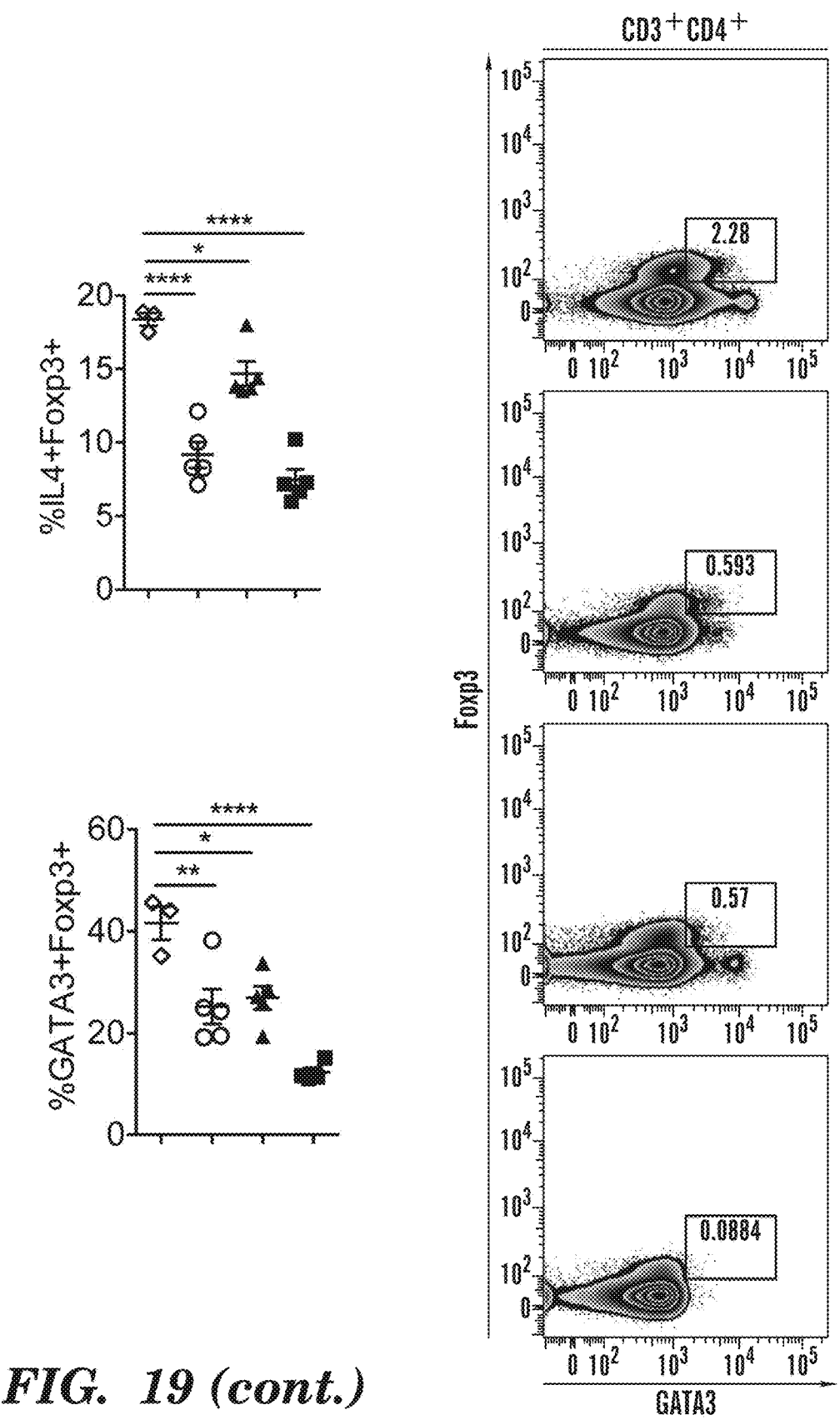
Figure 20A:
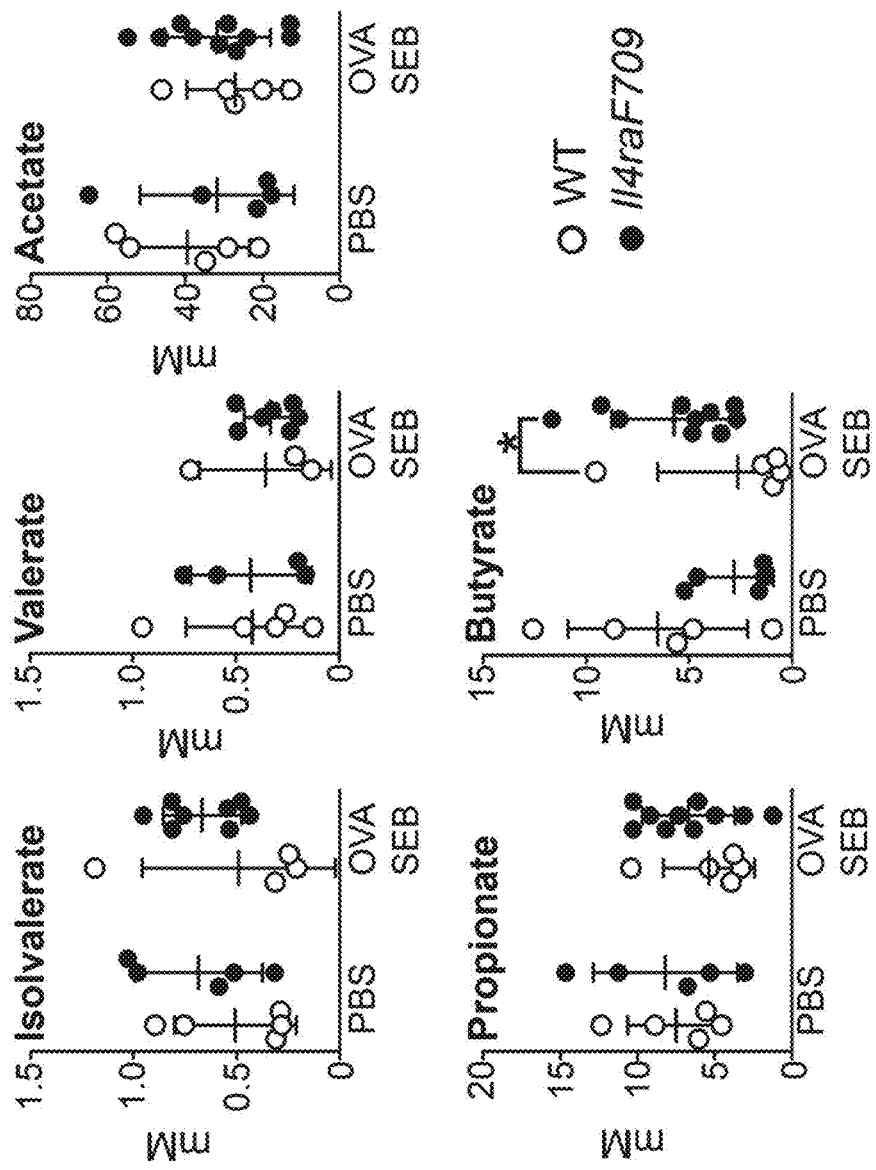
FIG. 20A-FIG. 20C. Short chain fatty acid (SCFA) therapy does not rescue food allergy in Il4raF709 mice.
Figure 20A:
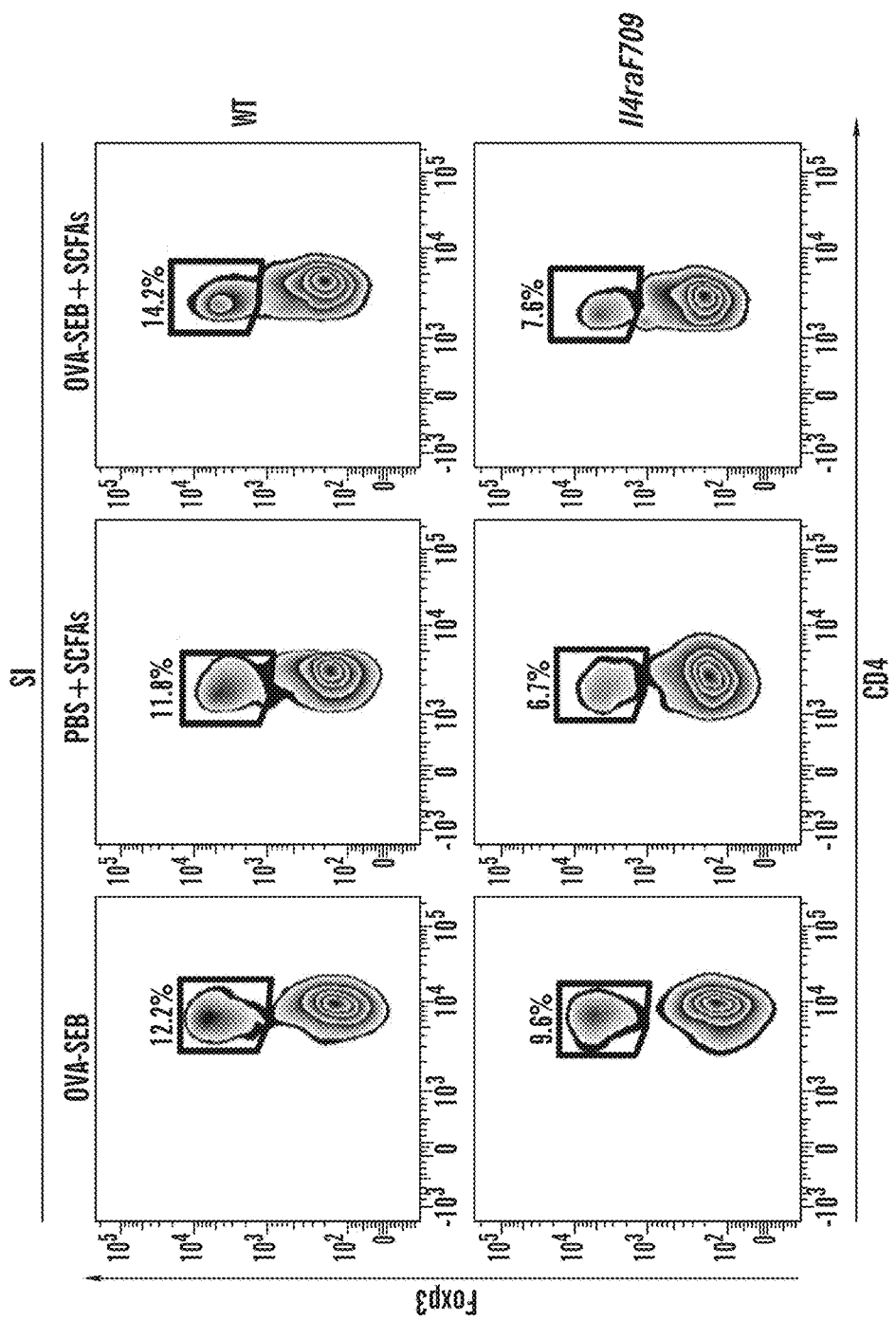
Figure 20B:
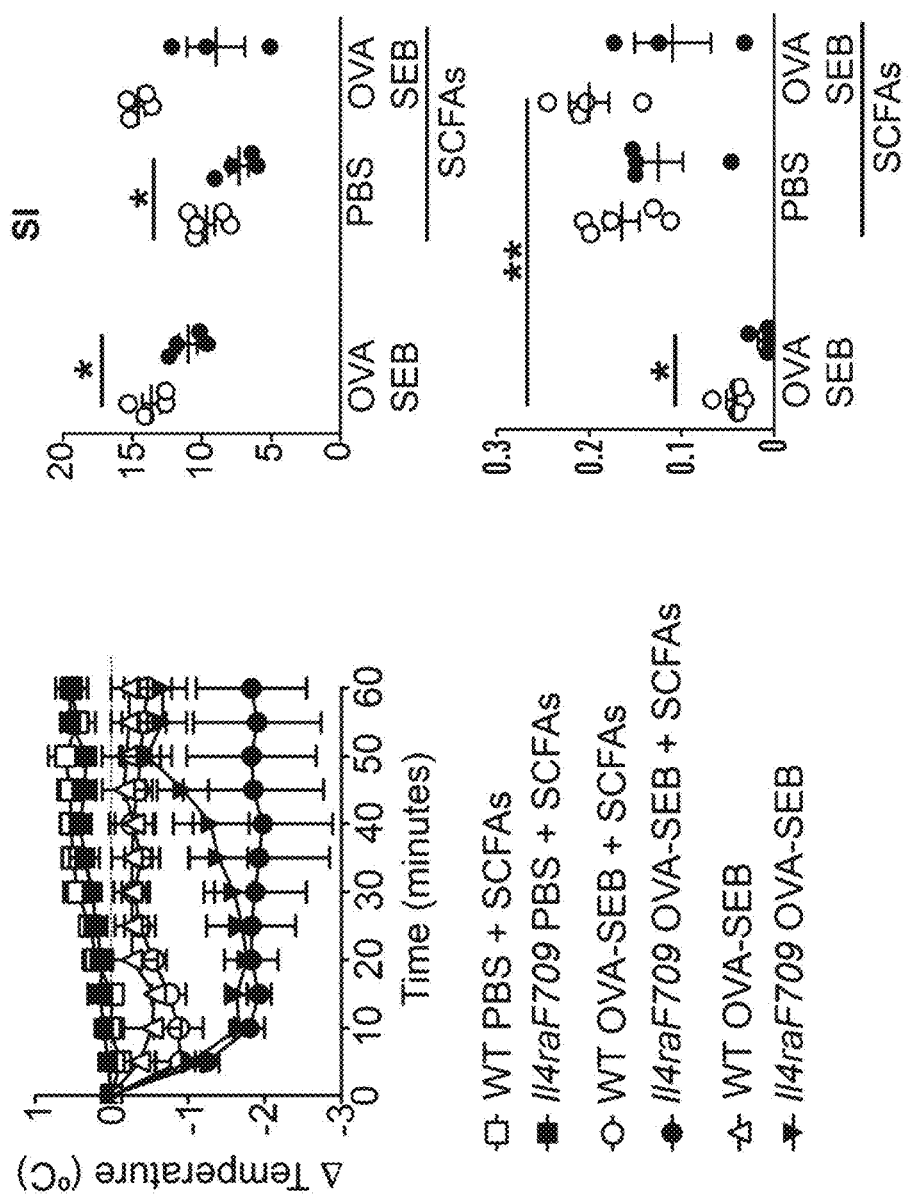
Figure 20C:
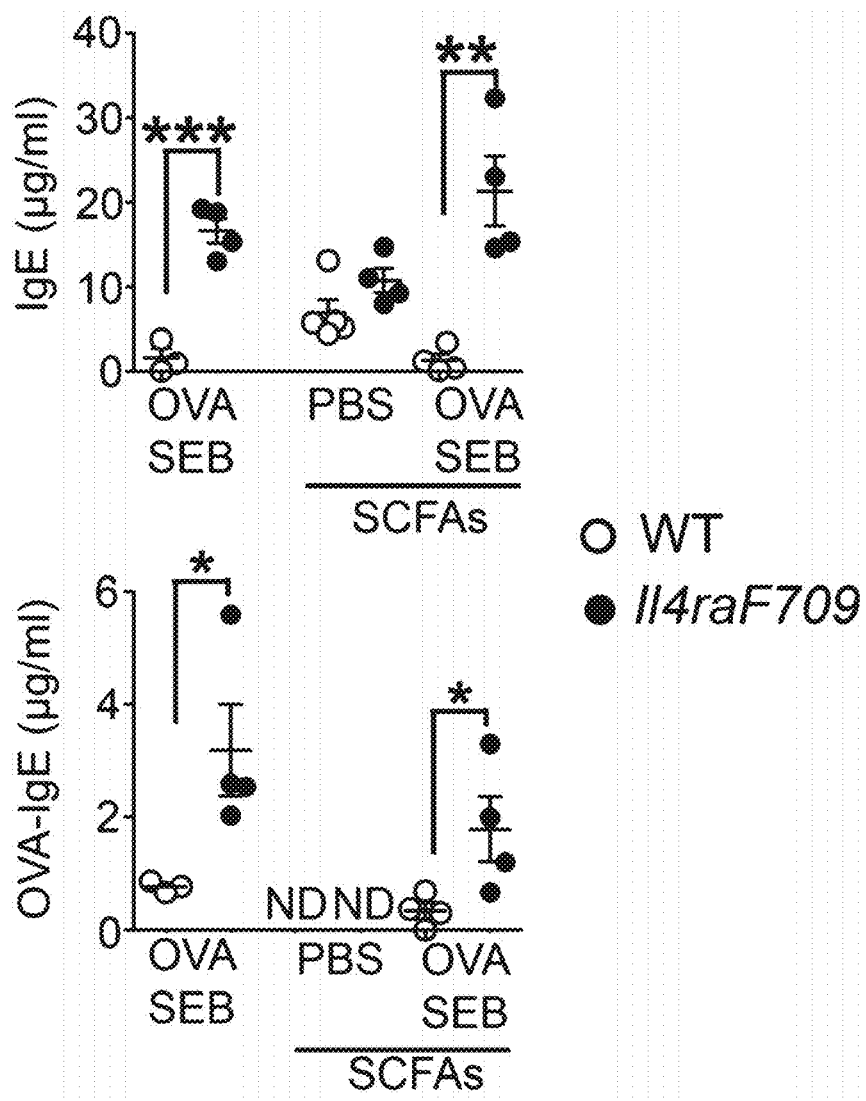
Figure 21A:
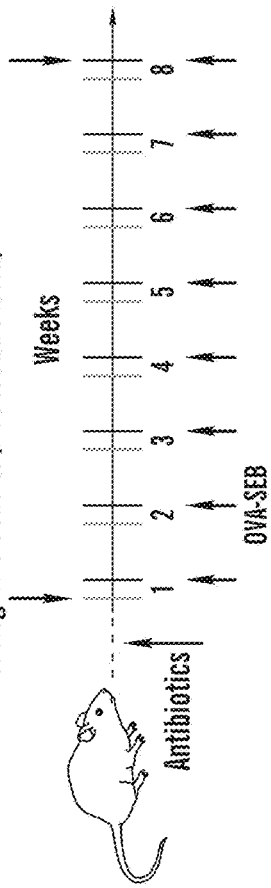
Figure 21B:
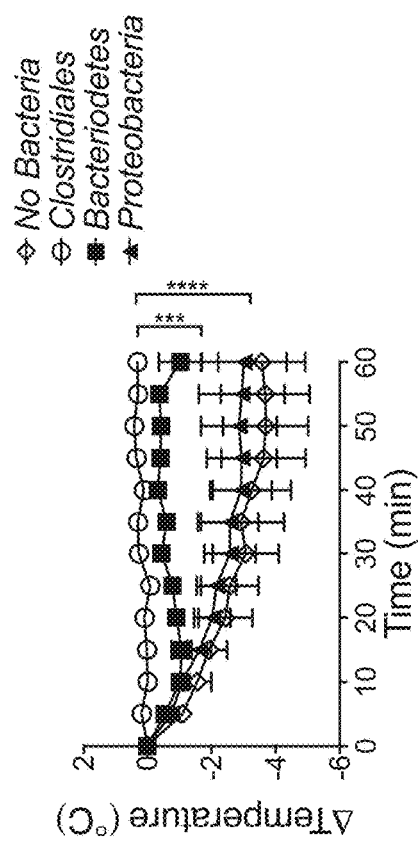
Figure 21F:
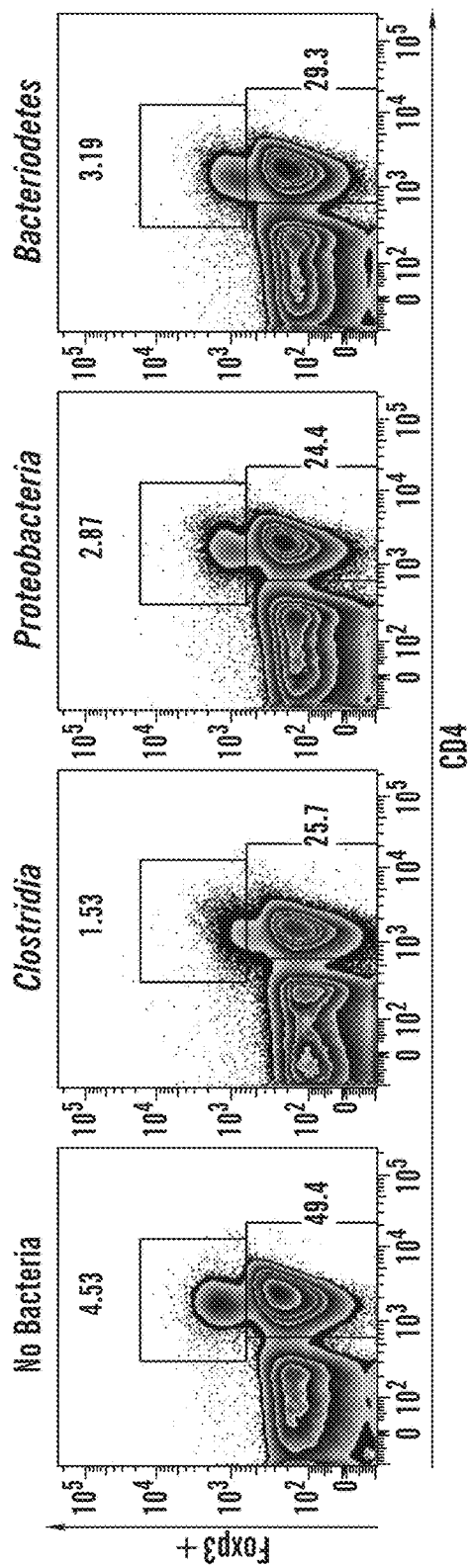
Figure 21G:
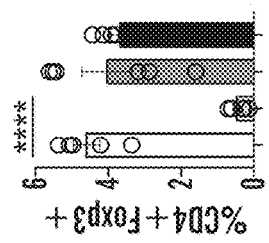
Figure 21H:
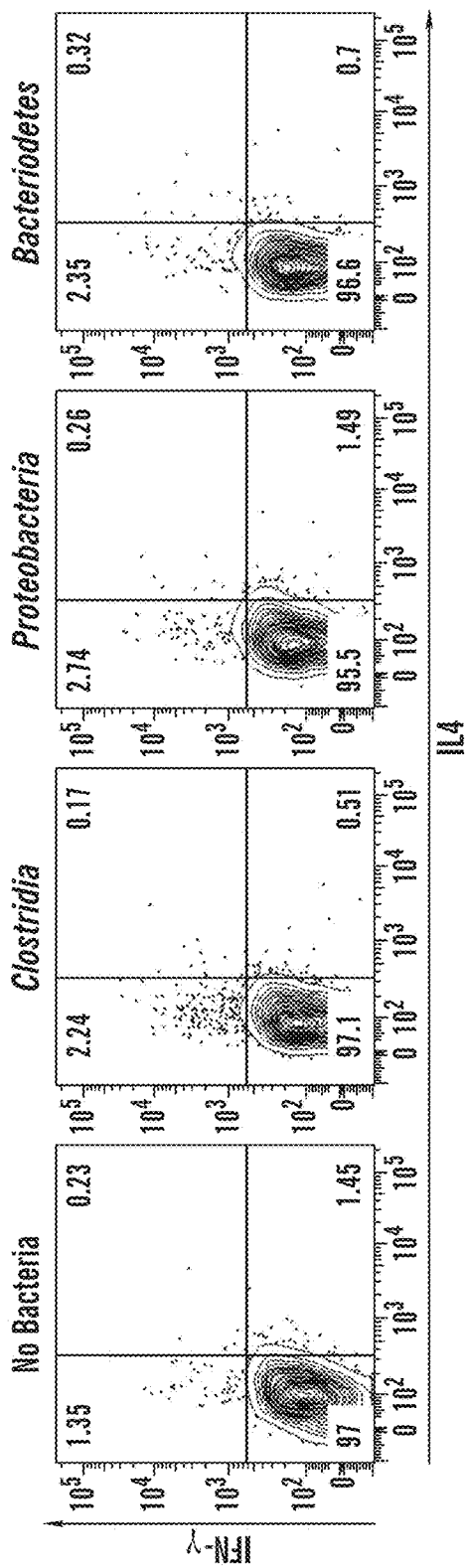
Figure 21I:
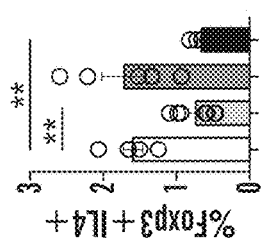

Example 4. GP-I and GP-II Consortia are Effective in Treat-to-Prevent Food Allergy in Conventional Wild-Type and IL4RA F709 Mice The protective effects of consortia GP-I (Clostridial species) and GP-II (*Bacteroidetes* species) were examined in conventional and food allergy-prone IL4RA F709 mice. In this series of experiments, the animals were conventional, i.e., not germ-free. Animals were treated with a course of oral broad-spectrum antibiotics one week prior to initiating sensitization with egg ovalbumin (OVA) and staphylococcal enterotoxin B (SEB). After antibiotic treatment, the mice received weekly doses of the GP-I, GP-II or negative control consortia (NCC), and weekly doses of OVA-SEB before challenge at week 8 with oral ovalbumin. See FIG. 21A. Following challenge, animals were examined for temperature drop (FIG. 21B), total and OVA-specific IgE titers (FIG. 21C), mast cell protease-1 levels (FIG. 21D), mast cell recruitment to the small bowel (FIG. 2E) and the development of FoxP3+ regulatory T cells (FIGS. 21F and G) versus IL-4 producing T cells (FIGS. 21H and I). The data clearly show that the *Clostridiales* and *Bacteroidetes* consortia (GP-I and GP-II, respectively) protected against allergy as measured by these criteria, while animals treated with the negative control consortium (denoted "Proteobacteria") or no bacteria showed a clear allergic response. Thus, GP-1I and GP-II are effective to prevent the development of food allergy.

Figure 22A:
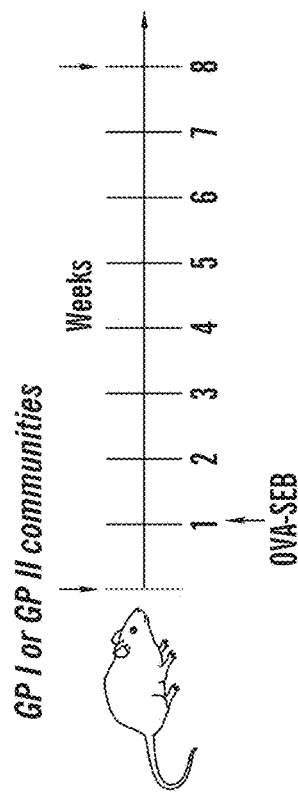
FIG. 22A-FIG. 22H. GP-1 (*Clostridiales*) and GP-II (*Bacteriodetes*) consortia protect germ-free mice in treat-to-prevent regimens. Gnotobiotic mice inoculated with either the GP-I or GP-II consortia (one time) prior to OVA sensitization (left arrow, FIG. 22A) and final challenge (right arrow, FIG. 22A).
Figure 22B:
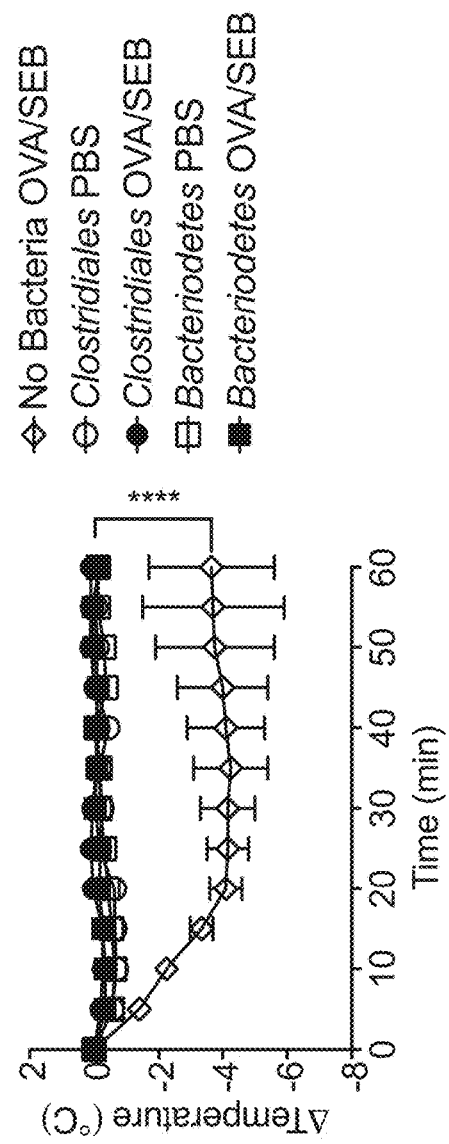
Figure 22C:
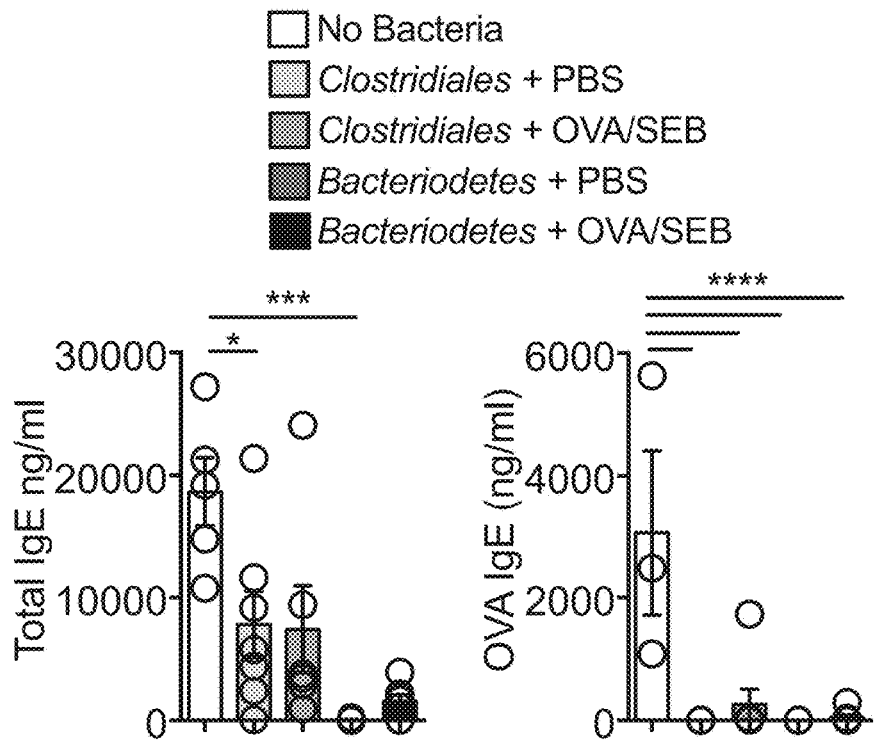
Figure 22D:
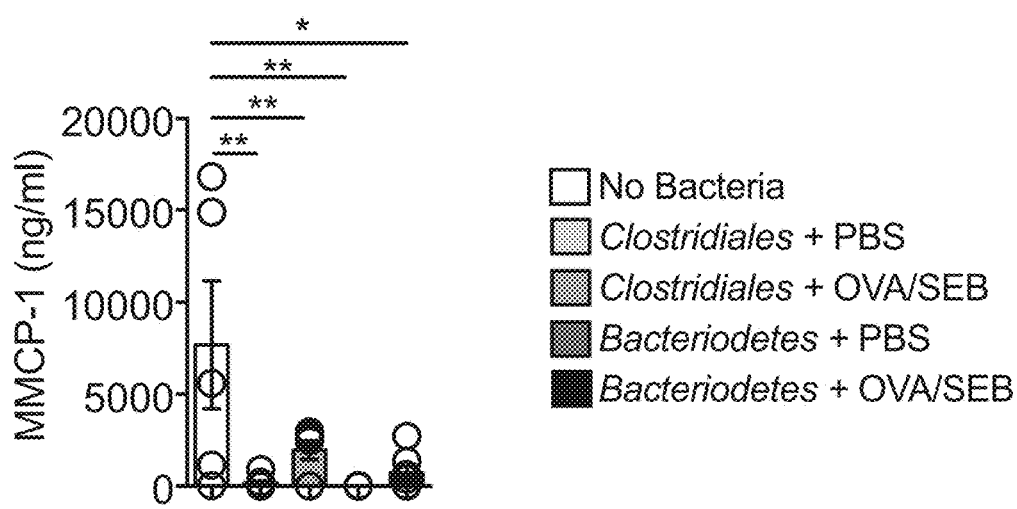
Figures 22E, 22F:
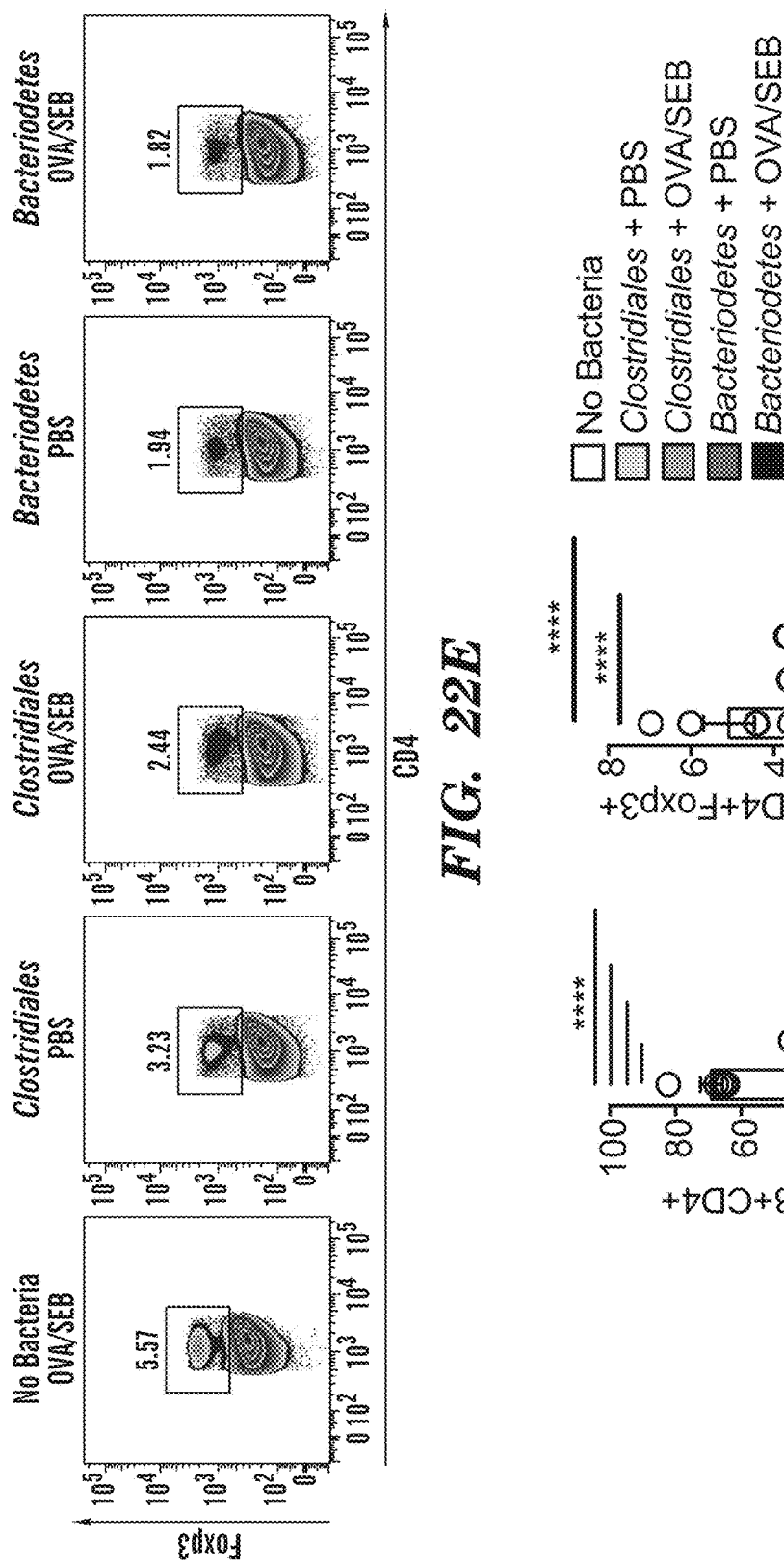
Figure 22G:
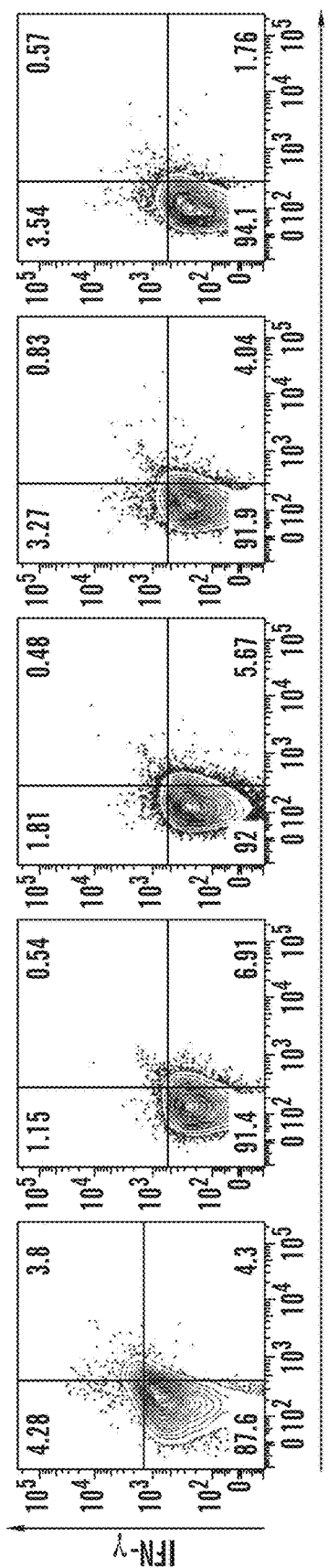
Figure 22H:
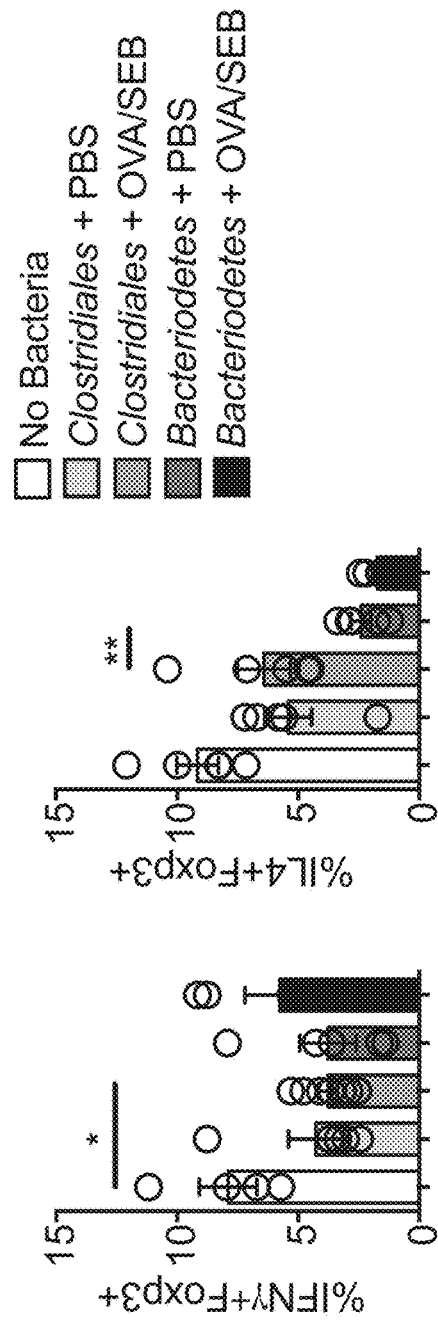

Example 5. GP-I and GP-II Consortia Protect Germ-Free Mice in Treat-to-Prevent Regimens The protective effects of the GP-I and GP-II consortia were examined in germ-free mice treated with saline (PBS) or with OVA-SEB. The germ-free mice received either no bacteria or consortia GP-I or GP-II prior to 7 weekly sensitizing doses of OVA-SEB (see FIG. 22A). Challenged on the $8^{th}$ week with OVA, the mice were examined for evidence of allergic reaction as described in Example 4. The data (see FIGS. 22 B-H) clearly show that unlike animals receiving no bacteria, germ-free animals administered the GP-I and GP-II consortia experienced substantially no allergic reaction upon challenge with the sensitizing food allergen.

Figure 23A:
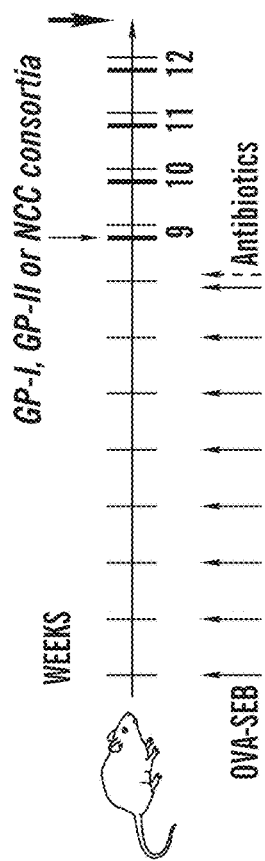
Figure 23B:
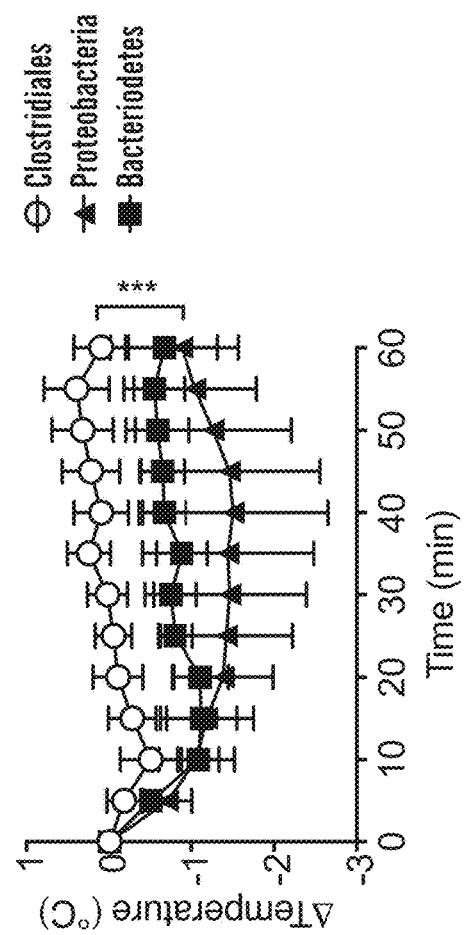
Figure 23H:
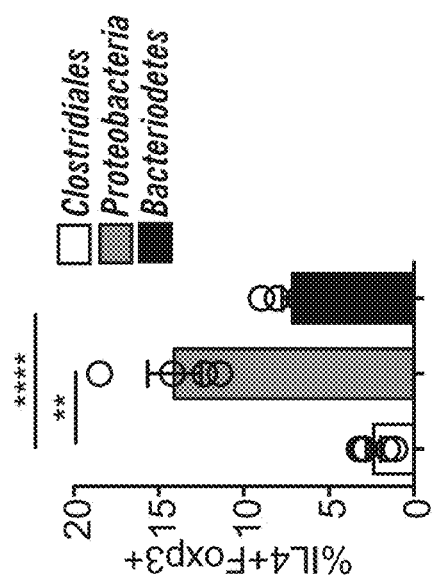
Figure 23G:
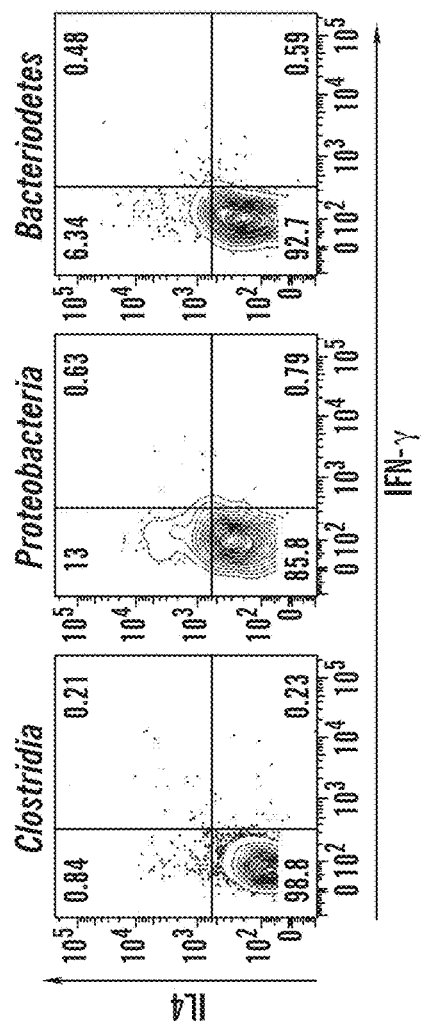

Example 6. GP-I and GP-II Consortia Cure Food Allergy in Conventional IL4RA F709 Mice; Negative Control Consortium does not To test whether animals that had been sensitized to food allergen before treatment with consortia shown herein to be protective against the development of food allergy could be cured of allergic sensitivity, conventional (i.e., non-germ-free) IL4RA F709 mice were sensitized to ovalbumin by 8 weekly treatments with OVA-SEB as performed in the experiments described above (see FIG. 23A for the experimental timeline). The animals were then treated with antibiotics to knock out their natural gut bacteria, before being treated with the GP-I, GP-II or NCC consortia using four weekly doses. After the fourth weekly dose of the test consortia, the animals were challenged with OVA. The data, which examined the same criteria examined in Examples 4 and 5, show that animals treated with the GP-I (*Clostridiales*) and GP-II (*Bacteroidetes*) consortia were substantially protected against allergic reaction, while those receiving the negative control (Proteobacteria) consortium were not (see FIG. 23B-H). These data demonstrate that not only can food allergy be prevented from developing through administration of the microbial consortia described herein, but established food allergy can also be treated by administration of the same protective consortia.

Figure 24K:
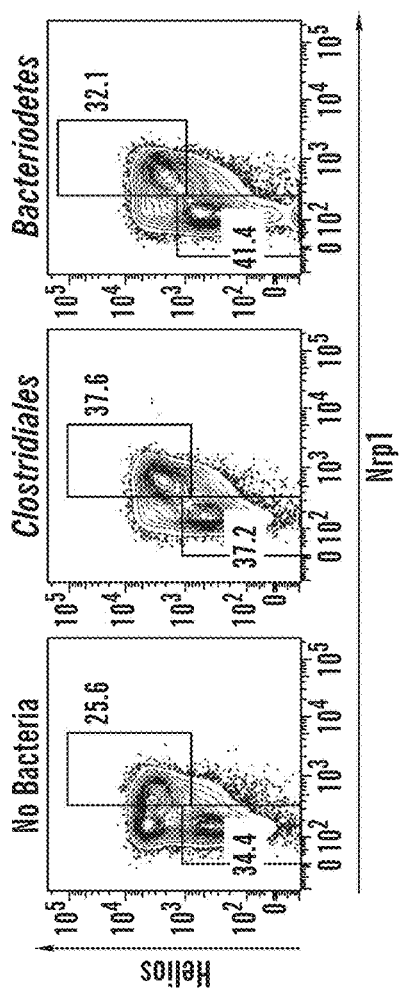
Figure 24L:
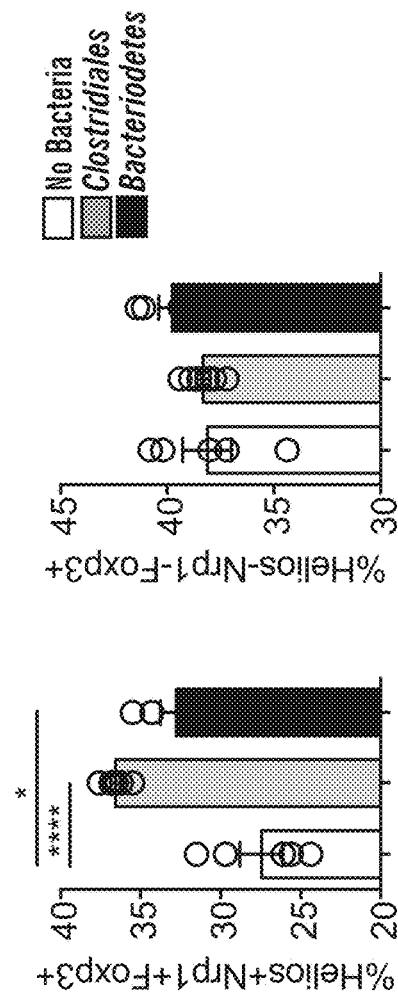

Example 7. GP-II Consortium (*Bacteroidetes*) Protects Against Food Allergy without Prior Antibiotic Knockdown of the Flora To examine whether it is necessary to first knock down the natural gut microbiota via antibiotic treatment in order to obtain protection in conventional mice, such animals were administered 8 weekly doses of GP-I and GP-II consortia or no additional bacterial treatment, while sensitizing mice to OVA with weekly OVA-SEB treatments over the course of 8 weeks (see FIG. 24A for the experimental timeline). Subsequent challenge with OVA demonstrated that, in the absence of natural flora knockdown prior to treatment with GP-I or GP-II, the *Bacteroidetes* consortium, GP-II, provided protection against the development of food allergy (see FIG. 24B-L). It is specifically contemplated that the administration of a combination of GP-II with one or more, or even all of the species of GP-I would provide an improved effect, in terms of initial response or protection and/or in terms of the persistence of such protection.

Figure 25A:
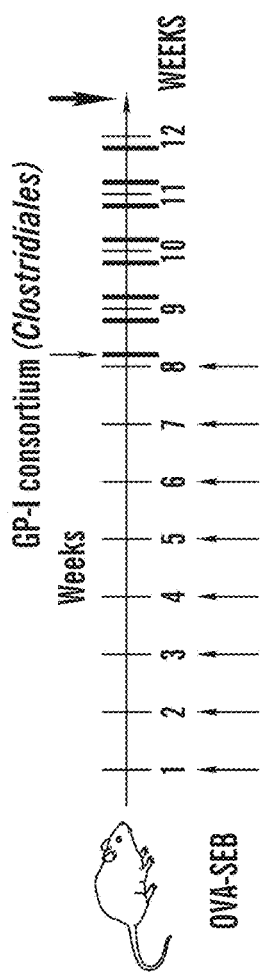
Figure 25B:
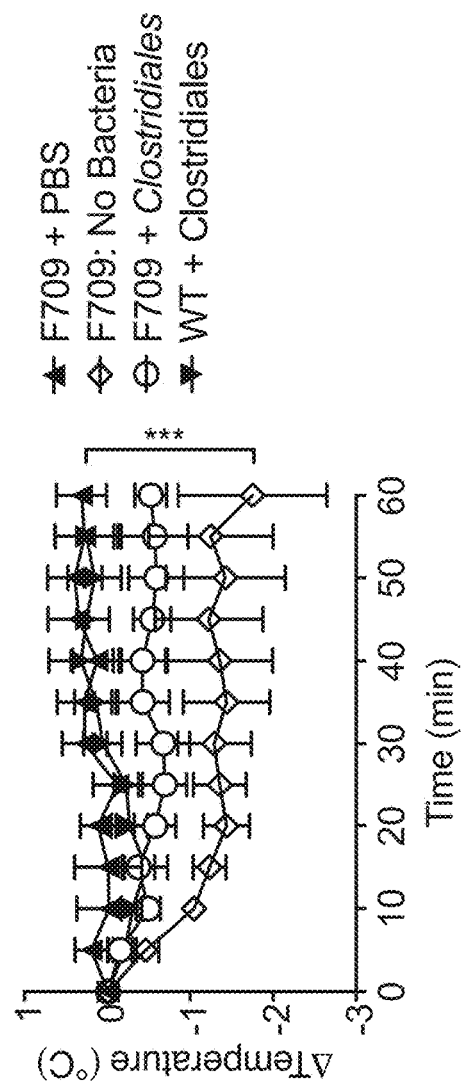

Example 8. The GP-I Consortium (*Clostridiales*) can Cure Food Allergy without the Use of Antibiotics in Conventional Mice To examine whether it is necessary to knock down the natural gut microbiota in order to cure food allergy in conventional mice, conventional wild-type and IL4RA F709 mutant mice were sensitized to ovalbumin via 8 weekly doses of OVA-SEB, followed by twice-weekly administration of the GP-I (*Clostridiales*) consortium for 4 weeks, without prior antibiotic knockdown of the natural gut microbiota (see FIG. 25A for the experimental timeline). When challenged after the four weeks of GP-I administration, the data show that the GP-I consortium was effective to reduce allergic symptoms by all measures examined in both the wild-type and allergy-prone animals (See FIG. 25B-I). The data indicate that the administration of the GP-I consortium is able to cure food allergy in the presence of the natural gut flora—that is, it is not necessary to first knock down the natural gut microbiota to effectively treat food allergy using protective microbial consortia such as the GP-I consortium.

The invention claimed is:

1. A method, comprising administering to a subject having an inflammatory disorder a pharmaceutical composition comprising:
    a purified mixture of live bacteria for treatment of an inflammatory disorder in an individual in need thereof, wherein the live bacteria in the purified mixture consists of up to eleven bacterial species in total and includes the following bacterial species: *Clostridium ramosum, Clostridium scindens, Clostridium hiranonis, Clostridium bifermentans, Clostridium leptum,* and *Clostridium sardiniensis*; and
    (ii) a pharmaceutically acceptable carrier, wherein the pharmaceutical composition is formulated for intestinal delivery.

2. The method of claim 1, wherein the bacterial species are *Clostridium ramosum, Clostridium scindens, Clostridium hiranonis, Clostridium bifermentans, Clostridium leptum,* and *Clostridium sardiniensis.*

3. The method of claim 1, wherein the pharmaceutical composition is formulated for oral administration.

4. The method of claim 3, wherein the pharmaceutical composition is in an oral dosage form of a capsule, a reconstituted lyophilisate, a food item, a liquid, gel, or fluid-gel.

5. The method of claim 1, wherein the inflammatory disorder is a food allergy.

6. The method of claim 5, wherein administration of the pharmaceutical composition is in an amount sufficient to treat or prevent the food allergy.

7. The method of claim 1, wherein the live bacteria in the purified mixture are present in substantially equal biomass.

8. The method of claim 1, wherein the purified mixture of live bacteria comprises species present in a total amount of at least about $1\times10^8$ CFUs/ml.

9. The method of claim 1, wherein the purified mixture of live bacteria does not comprise any of the species *Escherichia coli, Klebsiella pneumoniae, Proteus mirabilis, Enterobacter cloacae, Bilophila wadsworthia, Alistipes onderdonkii, Desulfovibrio* species, *Lactobacillus johnsonii,* or *Parasutterella excrementihominis.*

10. The method of claim 1, wherein the pharmaceutical composition is enteric coated.

* * * * *

UNITED STATES PATENT AND TRADEMARK OFFICE
CERTIFICATE OF CORRECTION

PATENT NO. : 10,391,131 B2
APPLICATION NO. : 16/293046
DATED : August 27, 2019
INVENTOR(S) : Talal A. Chatila et al.

It is certified that error appears in the above-identified patent and that said Letters Patent is hereby corrected as shown below:

In the Specification

At Column 1, Line 20-23, please delete:
"This invention was made with Government Support under Grant Nos. 1R56AI11798-01 and P30 DK056338 awarded by the National Institutes of Health. The Government has certain rights in the invention."

And insert the following:
-- This invention was made with government support under Grant nos. AI117983, AI126915, and DK056338, awarded by The National Institutes of Health. The government has certain rights in the invention. --

Signed and Sealed this
Thirty-first Day of March, 2020

Andrei Iancu
*Director of the United States Patent and Trademark Office*